(12) United States Patent
Matsui et al.

(10) Patent No.: US 7,825,070 B2
(45) Date of Patent: Nov. 2, 2010

(54) METHOD OF TWO-DIMENSIONALLY ARRAYING FERRITIN ON SUBSTRATE

(75) Inventors: Takuro Matsui, Kanagawa (JP); Nozomu Matsukawa, Nara (JP); Kazuaki Nishio, Osaka (JP)

(73) Assignee: Panasonic Corporation, Osaka (JP)

( * ) Notice: Subject to any disclaimer, the term of this patent is extended or adjusted under 35 U.S.C. 154(b) by 219 days.

(21) Appl. No.: 12/270,336

(22) Filed: Nov. 13, 2008

(65) Prior Publication Data

US 2009/0203552 A1 Aug. 13, 2009

(30) Foreign Application Priority Data

Nov. 16, 2007 (JP) ............... 2007-298189

(51) Int. Cl.
*C40B 50/18* (2006.01)
*C07K 17/00* (2006.01)

(52) U.S. Cl. ............... 506/32; 506/30; 530/300; 530/324; 530/327; 530/350

(58) Field of Classification Search ................ 506/32, 506/30; 530/350, 324, 327, 300
See application file for complete search history.

(56) References Cited

U.S. PATENT DOCUMENTS

2007/0112174 A1   5/2007   Shiba et al.

FOREIGN PATENT DOCUMENTS

| JP | 07/109364 | 4/1995 |
| JP | 2004-121154 | 4/2004 |
| JP | 2006-8436 | 1/2006 |
| WO | WO 03/040025 | 5/2003 |
| WO | WO 2005/010031 A1 | 2/2005 |

OTHER PUBLICATIONS

Kase et al "Affinity Selection of Peptide Phage Libraries against Single-Wall Carbon Nanohorns Identifies a Peptide Aptamer with Conformational Variability" pp. 8939-8941 Lagmuir 2004 vol. 20, The American Chemical Society Published on web Aug. 26, 2004.
Sano et al "Endowing a Ferritin-Like Cage Protein with Hight Affinity and Selective for Certain Inorganic Materials" pp. 826-832 Small 2005 No. 8-9 Whiley-VCH Verlag GmbH & Co.
Okuda et al "Self-Organized Inorganic Nanoparticle Arrays on Protein Lattices" pp. 991-993 Nano Letters vol. 5, No. 5, American Chemical Society 2005, published on web Apr. 26, 2005.
Matsui et al "Realizing a Two-Dimensional Ordered Array of Ferritin Molecules Directly on a Solid Surface Utilizing Carbonaceous Material Affinity Peptides" pp. 1615-1618 Langmuir 2007 vol. 23 The American Chemical Society, Published on the web Jan. 11, 2007.
Matsui et al "Direct Production of a Two-Dimensional Ordered Array of Ferritin-Nanoparticles on a Silicon Substrate" pp. L13-L15 Japanese Journal of Applied Physics vol. 46, No. 28 The Japanese Society of Applied Physics 2007.

*Primary Examiner*—T. D. Wessendorf
(74) *Attorney, Agent, or Firm*—McDermott Will & Emery LLP

(57) ABSTRACT

A novel method for two-dimensionally arraying ferritin on a substrate is provided which obviates the need for a metal ion that permits linking between adjacent two ferritin particles. In a method of two-dimensionally arraying ferritin on a substrate, the surface of the substrate is hydrophilic, and the method includes the steps of: developing a solution containing a solvent and the ferritin on the substrate; and removing the solvent from the solution developed on the substrate, while the ferritin has an amino acid sequence set out in SEQ ID NO: 1 modified at its N-terminus.

5 Claims, 88 Drawing Sheets

Example 1
Y6S4DE(In)/PIPES(NaOH)/SiO$_2$

Example 1
Y6S4DE(In)/PIPES(NaOH)/SiO$_2$
(Fourier transform image)

Example 2
Y6S4DE(In)/PIPES(Tris)/SiO$_2$

Example 2
Y6S4DE(In)/PIPES(Tris)/SiO$_2$
(Fourier transform image)

Example 3
Y6S4DE(In)/Ammonium sulfate /SiO$_2$

Example 3
Y6S4DE(In)/Ammonium sulfate /SiO$_2$
(Fourier transform image )

Example 4
Y6S4DE(In)/Ammonium acetate /SiO$_2$

Example 4
Y6S4DE(In)/Ammonium acetate /SiO$_2$
(Fourier transform image )

Comparative example 1
N1-LF(In)/PIPES(NaOH)/SiO$_2$

Comparative example 1
N1-LF(In)/PIPES(NaOH)/SiO$_2$
(Fourier transform image )

Comparative example 2
N1-LF(In)/PIPES(Tris)/SiO$_2$

Comparative example 2
N1-LF(In)/PIPES(Tris)/SiO$_2$
(Fourier transform image)

Comparative example 3
N1-LF(In)/Ammonium sulfate /SiO$_2$

Comparative example 3
N1-LF(In)/Ammonium sulfate /SiO$_2$
(Fourier transform image )

Comparative example 4
N1-LF(In)/Ammonium acetate /SiO$_2$

Comparative example 4
N1-LF(In)/Ammonium acetate /SiO$_2$
(Fourier transform image)

Comparative example 5
D2N(In)/PIPES(NaOH)/SiO$_2$

Comparative example 5
D2N(In)/PIPES(NaOH)/SiO$_2$
( Fourier transform image )

Comparative example 6
D2N(In)/Ammonium sulfate /SiO$_2$

Comparative example 6
D2N(In)/Ammonium sulfate /SiO$_2$
(Fourier transform image )

Comparative example 7
D2N(In)/Ammonium acetate /SiO$_2$

Comparative example 7
D2N(In)/Ammonium acetate /SiO$_2$
(Fourier transform image )

Comparative example 8
E10Q(In)/PIPES(NaOH)/SiO$_2$

Comparative example 8
E10Q(In)/PIPES(NaOH)/SiO$_2$
(Fourier transform image)

Comparative example 9
E10Q(In)/Ammonium sulfate /SiO$_2$

Comparative example 9
E10Q(In)/Ammonium sulfate /SiO$_2$
(Fourier transform image )

Comparative example 10
E10Q(In)/Ammonium acetate /SiO$_2$

Comparative example 10
E10Q(In)/Ammonium acetate /SiO$_2$
(Fourier transform image )

Comparative example 11
E10S(In)/TrisSuspension /SiO$_2$

Comparative example 11
E10S(In)/TrisSuspension /SiO$_2$
(Fourier transform image )

Comparative example 12
P7S(In)/PIPES(NaOH)/SiO$_2$

Comparative example 12
P7S(In)/PIPES(NaOH)/SiO$_2$
(Fourier transform image)

Comparative example 13
P7S(In)/Ammonium sulfate /SiO$_2$

Comparative example 13
P7S(In)/Ammonium sulfate /SiO$_2$
(Fourier transform image )

Comparative example 14
P7S(In)/Ammonium acetate /SiO₂

Comparative example 14
P7S(In)/Ammonium acetate /SiO$_2$
(Fourier transform image )

Comparative example 15
Y8F-Y9F(In)/PIPES(NaOH)/SiO$_2$

Comparative example 15
Y8F-Y9F(In)/PIPES(NaOH)/SiO$_2$
(Fourier transform image )

Comparative example 16
Y8F-Y9F(In)/PIPES(Tris)/SiO$_2$

Comparative example 16
Y8F-Y9F(In)/PIPES(Tris)/SiO$_2$
(Fourier transform image )

Comparative example 17
Y8F-Y9F(In)/Ammonium sulfate /SiO₂

Comparative example 17
Y8F-Y9F(In)/Ammonium sulfate /SiO$_2$
(Fourier transform image )

Comparative example 18
Y8F-Y9F(In)/Ammonium acetate /SiO$_2$

Comparative example 18
Y8F-Y9F(In)/Ammonium acetate /SiO$_2$
(Fourier transform image )

Comparative example 19
S5T-S6T(In)/Ammonium sulfate /SiO$_2$

Comparative example 19
S5T-S6T(In)/Ammonium sulfate /SiO$_2$
(Fourier transform image)

Comparative example 20
S5T-S6T(In)/Ammonium acetate /SiO$_2$

Comparative example 20
S5T-S6T(In)/Ammonium acetate /SiO$_2$
(Fourier transform image )

Comparative example 21
△HY(In)/PIPES(NaOH)/SiO$_2$

Comparative example 21
ΔHY(In)/PIPES(NaOH)/SiO$_2$
(Fourier transform image)

Comparative example 22
△HY(In)/Ammonium sulfate /SiO$_2$

Comparative example 22
ΔHY(In)/Ammonium sulfate /SiO$_2$
(Fourier transform image )

Comparative example 23
△HY(In)/Ammonium acetate /SiO$_2$

Comparative example 23
ΔHY(In)/Ammonium acetate /SiO$_2$
(Fourier transform image )

Comparative example 24
△ AR(In)/PIPES(NaOH)/SiO$_2$

Comparative example 24
ΔAR(In)/PIPES(NaOH)/SiO$_2$
(Fourier transform image)

Comparative example 25
△AR(In)/Ammonium sulfate /SiO$_2$

Comparative example 25
ΔAR(In)/Ammonium sulfate /SiO$_2$
(Fourier transform image )

Comparative example 26
△ AR(In)/Ammonium acetate /SiO$_2$

Comparative example 26
Δ AR(In)/Ammonium acetate /SiO$_2$
(Fourier transform image )

Comparative example 27
Shuffle(In)/Ammonium sulfate /SiO$_2$

Comparative example 27
Shuffle(In)/Ammonium sulfate /SiO$_2$
(Fourier transform image )

Comparative example 28
Shuffle(In)/Ammonium acetate /SiO$_2$

Comparative example 28
Shuffle(In)/Ammonium acetate /SiO$_2$
(Fourier transform image )

Comparative example 29
1st-half(In)/PIPES(NaOH)/SiO$_2$

Comparative example 29
1st-half(In)/PIPES(NaOH)/SiO$_2$
(Fourier transform image )

Comparative example 30
1st-half(In)/Ammonium sulfate /SiO$_2$

Comparative example 30
1st-half(In)/Ammonium sulfate /SiO$_2$
(Fourier transform image )

Comparative example 31
1st-half(In)/Ammonium acetate /SiO$_2$

Comparative example 31
1st-half(In)/Ammonium acetate /SiO$_2$
(Fourier transform image )

Comparative example 32
2nd-half(In)/PIPES(NaOH)/SiO$_2$

Comparative example 32
2nd-half(In)/PIPES(NaOH)/SiO$_2$
(Fourier transform image )

Comparative example 33
2nd-half(In)/Ammonium sulfate /SiO$_2$

Comparative example 33
2nd-half(In)/Ammonium sulfate /SiO$_2$
(Fourier transform image )

Comparative example 34
2nd-half(In)/Ammonium acetate /SiO$_2$

Comparative example 34
2nd-half(In)/Ammonium acetate /$SiO_2$
(Fourier transform image )

Comparative example 35
5AA(In)/PIPES(NaOH)/SiO$_2$

Comparative example 35
5AA(In)/PIPES(NaOH)/SiO$_2$
(Fourier transform image )

Comparative example 36
5AA(In)/Ammonium sulfate /SiO$_2$

Comparative example 36
5AA(In)/Ammonium sulfate /SiO$_2$
(Fourier transform image )

Comparative example 37
5AA(In)/Ammonium acetate /SiO$_2$

Comparative example 37
5AA(In)/Ammonium acetate /SiO$_2$
(Fourier transform image )

SEQUENCE LISTING

<160> NUMBER OF SEQ ID NOS: 31

<210> SEQ ID NO 1
<211> LENGTH: 12
<212> TYPE: PRT
<213> ORGANISM: Artificial

<220> FEATURE:
<223> OTHER INFORMATION: Twelve amino acids for alignment of ferritin on substrate.
<220> FEATURE:
<221> NAME/KEY: MISC_FEATURE
<222> LOCATION: (1)..(12)
<223> OTHER INFORMATION: of SEQ ID NO: 1: amino acid sequence including 12 residues for arraying ferritin of the present invention on a substrate

<400> SEQUENCE: 1

Asp Tyr Tyr Ser Ser Ser Tyr Tyr Glu Tyr Tyr Ser
1               5                   10

<210> SEQ ID NO 2
<211> LENGTH: 187
<212> TYPE: PRT
<213> ORGANISM: Artificial
<220> FEATURE:
<223> OTHER INFORMATION: A modified horse ferritin having amino-terminal methionine and twelve amino acids at amino-terminal.
<220> FEATURE:
<221> NAME/KEY: MISC_FEATURE
<222> LOCATION: (1)..(12)
<223> OTHER INFORMATION: of SEQ ID NO: 2: modified ferritin derived from horse prepared by adding amino terminal methionine and an amino acid including 12 residues to the amino terminal of the amino acid sequence of ferritin of the present invention

<400> SEQUENCE: 2

Met Asp Tyr Tyr Ser Ser Ser Tyr Tyr Glu Tyr Tyr Ser Ser Ser Gln
1               5                   10                  15

Ile Arg Gln Asn Tyr Ser Thr Glu Val Glu Ala Ala Val Asn Arg Leu
                20                  25                  30

Val Asn Leu Tyr Leu Arg Ala Ser Tyr Thr Tyr Leu Ser Leu Gly Phe
            35                  40                  45

Tyr Phe Asp Arg Asp Asp Val Ala Leu Glu Gly Val Cys His Phe Phe
        50                  55                  60

Arg Glu Leu Ala Glu Glu Lys Arg Glu Gly Ala Glu Arg Leu Leu Lys
65                  70                  75                  80

Met Gln Asn Gln Arg Gly Gly Arg Ala Leu Phe Gln Asp Leu Gln Lys
                85                  90                  95

Pro Ser Gln Asp Glu Trp Gly Thr Thr Pro Asp Ala Met Lys Ala Ala
            100                 105                 110

Ile Val Leu Glu Lys Ser Leu Asn Gln Ala Leu Leu Asp Leu His Ala
        115                 120                 125

Leu Gly Ser Ala Gln Ala Asp Pro His Leu Cys Asp Phe Leu Glu Ser
    130                 135                 140

His Phe Leu Asp Glu Glu Val Lys Leu Ile Lys Lys Met Gly Asp His
145                 150                 155                 160

Leu Thr Asn Ile Gln Arg Leu Val Gly Ser Gln Ala Gly Leu Gly Glu
                165                 170                 175

Tyr Leu Phe Glu Arg Leu Thr Leu Lys His Asp
            180                 185

<210> SEQ ID NO 3
<211> LENGTH: 3848
<212> TYPE: DNA
<213> ORGANISM: Artificial
<220> FEATURE:
<223> OTHER INFORMATION: Plasmid vector for Y6S4DE-Fer0 protein expression.
<220> FEATURE:
<221> NAME/KEY: misc_feature
<222> LOCATION: (1)..(3848)
<223> OTHER INFORMATION: of SEQ ID NO: 3: plasmid vector for ferritin
      protein expression of the present invention

<400> SEQUENCE: 3

| | | | | | |
|---|---|---|---|---|---|
| ctgttttggc | ggatgagaga | agattttcag | cctgatacag | attaaatcag | aacgcagaag | 60 |
| cggtctgata | aaacagaatt | tgcctggcgg | cagtagcgcg | gtggtcccac | ctgaccccat | 120 |
| gccgaactca | gaagtgaaac | gccgtagcgc | cgatggtagt | gtggggtctc | cccatgcgag | 180 |
| agtagggaac | tgccaggcat | caaataaaac | gaaaggctca | gtcgaaagac | tgggcctttc | 240 |
| gttttatctg | ttgtttgtcg | gtgaacgctc | tcctgagtag | gacaaatccg | ccgggagcgg | 300 |
| atttgaacgt | tgcgaagcaa | cggcccggag | ggtggcgggc | aggacgcccg | ccataaactg | 360 |
| ccaggcatca | aattaagcag | aaggccatcc | tgacggatgg | ccttttttgcg | tttctacaaa | 420 |
| ctcttttgtt | tattttttcta | aatacattca | aatatgtatc | cgctcatgag | acaataaccc | 480 |
| tgataaatgc | ttcaataata | ttgaaaaagg | aagagtatga | gtattcaaca | tttccgtgtc | 540 |
| gcccttattc | ccttttttgc | ggcattttgc | cttcctgttt | ttgctcaccc | agaaacgctg | 600 |
| gtgaaagtaa | aagatgctga | agatcagttg | ggtgcacgag | tgggttacat | cgaactggat | 660 |
| ctcaacagcg | gtaagatcct | tgagagtttt | cgccccgaag | aacgttttcc | aatgatgagc | 720 |
| acttttaaag | ttctgctatg | tggcgcggta | ttatcccgtg | ttgacgccgg | gcaagagcaa | 780 |
| ctcggtcgcc | gcatacacta | ttctcagaat | gacttggttg | agtactcacc | agtcacagaa | 840 |
| aagcatctta | cggatggcat | gacagtaaga | gaattatgca | gtgctgccat | aaccatgagt | 900 |
| gataacactg | cggccaactt | acttctgaca | acgatcggag | gaccgaagga | gctaaccgct | 960 |
| tttttgcaca | acatggggga | tcatgtaact | cgccttgatc | gttgggaacc | ggagctgaat | 1020 |
| gaagccatac | caaacgacga | gcgtgacacc | acgatgcctg | tagcaatggc | aacaacgttg | 1080 |
| cgcaaactat | taactggcga | actacttact | ctagcttccc | ggcaacaatt | aatagactgg | 1140 |
| atggaggcgg | ataaagttgc | aggaccactt | ctgcgctcgg | cccttccggc | tggctggttt | 1200 |
| attgctgata | aatctggagc | cggtgagcgt | gggtctcgcg | gtatcattgc | agcactgggg | 1260 |
| ccagatggta | agccctcccg | tatcgtagtt | atctacacga | cggggagtca | ggcaactatg | 1320 |
| gatgaacgaa | atagacagat | cgctgagata | ggtgcctcac | tgattaagca | ttggtaactg | 1380 |
| tcagaccaag | tttactcata | tatactttag | attgatttaa | aacttcattt | ttaatttaaa | 1440 |
| aggatctagg | tgaagatcct | ttttgataat | ctcatgacca | aaatccctta | acgtgagttt | 1500 |
| tcgttccact | gagcgtcaga | ccccgtagaa | aagatcaaag | gatcttcttg | agatcctttt | 1560 |
| tttctgcgcg | taatctgctg | cttgcaaaca | aaaaaaccac | cgctaccagc | ggtggtttgt | 1620 |
| ttgccggatc | aagagctacc | aactcttttt | ccgaaggtaa | ctggcttcag | cagagcgcag | 1680 |
| ataccaaata | ctgtccttct | agtgtagccg | tagttaggcc | accacttcaa | gaactctgta | 1740 |
| gcaccgccta | catacctcgc | tctgctaatc | ctgttaccag | tggctgctgc | cagtggcgat | 1800 |
| aagtcgtgtc | ttaccgggtt | ggactcaaga | cgatagttac | cggataaggc | gcagcggtcg | 1860 |
| ggctgaacgg | ggggttcgtg | cacacagccc | agcttggagc | gaacgaccta | caccgaactg | 1920 |
| agatacctac | agcgtgagct | atgagaaagc | gccacgcttc | ccgaagggag | aaaggcggac | 1980 |
| aggtatccgg | taagcggcag | ggtcggaaca | ggagagcgca | cgagggagct | tccaggggga | 2040 |
| aacgcctggt | atctttatag | tcctgtcggg | tttcgccacc | tctgacttga | gcgtcgattt | 2100 |
| ttgtgatgct | cgtcaggggg | gcggagccta | tggaaaaacg | ccagcaacgc | ggcctttttta | 2160 |
| cggttcctgg | ccttttgctg | gccttttgct | cacatgttct | ttcctgcgtt | atcccctgat | 2220 |

-continued

```
tctgtggata accgtattac cgcctttgag tgagctgata ccgctcgccg cagccgaacg    2280
accgagcgca gcgagtcagt gagcgaggaa gcggaagagc gcccaatacg caaaccgcct    2340
ctccccgcgc gttggccgat tcattaatgc agcgaacgcc agcaagacgt agcccagcgc    2400
gtcggccgcc atgccggcga taatggcctg cttctcgccg aaacgtttgg tggcgggacc    2460
agtgacgaag gcttgagcga gggcgtgcaa gattccgaat accgcaagcg acaggccgat    2520
catcgtcgcg ctccagcgaa agcggtcctc gccgaaaatg acccagagcg ctgccggcac    2580
ctgtcctacg agttgcatga taaagaagac agtcataagt gcggcgacga tagtcatgcc    2640
ccgcgcccac cggaaggagc tgactgggtt gaaggctctc aagggcatcg gtcgacgctc    2700
tcccttatgc gactcctgca ttaggaagca gcccagtagt aggttgaggc cgttgagcac    2760
cgccgccgca aggaatggtg catgcaagga gatggcgccc aacagtcccc cggccacggg    2820
gcctgccacc atacccacgc cgaaacaagc gctcatgagc ccgaagtggc gagcccgatc    2880
ttccccatcg gtgatgtcgg cgatataggc gccagcaacc gcacctgtgg cgccggtgat    2940
gccggccacg atgcgtccgg cgtagaggat ccggagctta tcgactgcac ggtgcaccaa    3000
tgcttctggc gtcaggcagc catcggaagc tgtggtatgg ctgtgcaggt cgtaaatcac    3060
tgcataattc gtgtcgctca aggcgcactc ccgttctgga taatgttttt tgcgccgaca    3120
tcataacggt tctggcaaat attctgaaat gagctgttga caattaatca tcggctcgta    3180
taatgtgtgg aattgtgagc ggataacaat ttcacacagg aaacagaatt caaattctat    3240
ttcaaggaga caggatccat atggattatt attcgagctc gtattatgaa tattattcta    3300
gctcccagat tcgtcagaat tattctactg aagtggaggc cgccgtcaac cgcctggtca    3360
acctgtacct gcgggcctcc tacacctacc tctctctggg cttctatttc gaccgcgacg    3420
atgtggctct ggagggcgta tgccacttct tccgcgagtt ggcggaggag aagcgcgagg    3480
gtgccgagcg tctcttgaag atgcaaaacc agcgcggcgg ccgcgccctc ttccaggact    3540
tgcagaagcc gtcccaggat gaatgggta caaccccgga tgccatgaaa gccgccattg    3600
tcctggagaa gagcctgaac caggcccttt tggatctgca tgccctgggt ctgcccagg    3660 cagaccccca tctctgtgac ttcttggaga gccacttcct agacgaggag gtgaaactca    3720 tcaagagat gggcgaccat ctgaccaaca tccagaggct cgttggctcc caagctgggc    3780
tgggcgagta tctctttgaa aggctcactc tcaagcacga ctaagtcgac ctgcaggcat    3840
gcaagctt                                                            3848
```

<210> SEQ ID NO 4
<211> LENGTH: 3830
<212> TYPE: DNA
<213> ORGANISM: Artificial
<220> FEATURE:
<223> OTHER INFORMATION: pKIS9 plasmid vector for protein expression.
<220> FEATURE:
<221> NAME/KEY: misc_feature
<222> LOCATION: (1)..(3830)
<223> OTHER INFORMATION: of SEQ ID NO: 4: plasmid vector for protein
      expression

<400> SEQUENCE: 4

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtgggtctc cccatgcgag      180 agtagggaac tgccaggcat caaataaaac gaaaggctca gtcgaaagac tgggcctttc     240
```

-continued

```
gttttatctg ttgtttgtcg gtgaacgctc tcctgagtag gacaaatccg ccgggagcgg      300
atttgaacgt tgcgaagcaa cggcccggag ggtggcgggc aggacgcccg ccataaactg      360
ccaggcatca aattaagcag aaggccatcc tgacggatgg cctttttgcg tttctacaaa      420
ctcttttgtt tattttttcta aatacattca aatatgtatc cgctcatgag acaataaccc    480
tgataaatgc ttcaataata ttgaaaaagg aagagtatga gtattcaaca tttccgtgtc     540
gcccttattc ccttttttgc ggcatttgc cttcctgttt ttgctcaccc agaaacgctg       600
gtgaaagtaa aagatgctga agatcagttg ggtgcacgag tgggttacat cgaactggat     660
ctcaacagcg gtaagatcct tgagagtttt cgccccgaag aacgttttcc aatgatgagc     720
acttttaaag ttctgctatg tggcgcggta ttatcccgtg ttgacgccgg caagagcaa      780
ctcggtcgcc gcatacacta ttctcagaat gacttggttg agtactcacc agtcacagaa    840
aagcatctta cggatggcat gacagtaaga gaattatgca gtgctgccat aaccatgagt     900
gataacactg cggccaactt acttctgaca acgatcggag gaccgaagga gctaaccgct    960
tttttgcaca acatgggga tcatgtaact cgccttgatc gttgggaacc ggagctgaat      1020
gaagccatac caaacgacga gcgtgacacc acgatgcctg tagcaatggc aacaacgttg     1080
cgcaaactat taactggcga actacttact ctagcttccc ggcaacaatt aatagactgg    1140
atggaggcgg ataaagttgc aggaccactt ctgcgctcgg cccttccggc tggctggttt    1200
attgctgata atctggagc cggtgagcgt gggtctcgcg gtatcattgc agcactgggg     1260
ccagatggta agccctcccg tatcgtagtt atctacacga cggggagtca ggcaactatg     1320
gatgaacgaa atagacagat cgctgagata ggtgcctcac tgattaagca ttggtaactg    1380
tcagaccaag tttactcata tatactttag attgatttaa aacttcattt ttaatttaaa    1440
aggatctagg tgaagatcct ttttgataat ctcatgacca aaatccctta acgtgagttt    1500
tcgttccact gagcgtcaga ccccgtagaa aagatcaaag gatcttcttg agatcctttt   1560
tttctgcgcg taatctgctg cttgcaaaca aaaaaaccac cgctaccagc ggtggtttgt    1620
ttgccggatc aagagctacc aactcttttt ccgaaggtaa ctggcttcag cagagcgcag    1680
ataccaaata ctgtccttct agtgtagccg tagttaggcc accacttcaa gaactctgta   1740
gcaccgccta catacctcgc tctgctaatc ctgttaccag tggctgctgc cagtggcgat    1800
aagtcgtgtc ttaccgggtt ggactcaaga cgatagttac cggataaggc gcagcggtcg    1860
ggctgaacgg ggggttcgtg cacacagccc agcttggagc gaacgaccta caccgaactg    1920
agatacctac agcgtgagct atgagaaagc gccacgcttc ccgaagggag aaaggcggac    1980
aggtatccgg taagcggcag ggtcggaaca ggagagcgca cgagggagct tccaggggga    2040
aacgcctggt atctttatag tcctgtcggg tttcgccacc tctgacttga gcgtcgattt    2100
ttgtgatgct cgtcaggggg gcggagccta tggaaaaacg ccagcaacgc ggcctttta    2160
cggttcctgg ccttttgctg ccttttgct cacatgttct ttcctgcgtt atccctgat     2220
tctgtggata accgtattac cgcctttgag tgagctgata ccgctcgccg cagccgaacg    2280
accgagcgca gcgagtcagt gagcgaggaa gcggaagagc gcccaatacg caaaccgcct    2340
ctccccgcgc gttggccgat tcattaatgc agcgaacgcc agcaagacgt agcccagcgc    2400
gtcggccgcc atgccggcga taatggcctg cttctcgccg aaacgtttgg tggcgggacc    2460
agtgacgaag gcttgagcga gggcgtgcaa gattccgaat accgcaagcg acaggccgat    2520
catcgtcgcg ctccagcgaa agcggtcctc gccgaaaatg acccagagcg ctgccggcac    2580
```

-continued

```
ctgtcctacg agttgcatga taaagaagac agtcataagt gcggcgacga tagtcatgcc    2640
ccgcgcccac cggaaggagc tgactgggtt gaaggctctc aagggcatcg tcgacgctc     2700 tcccttatgc gactcctgca ttaggaagca gcccagtagt aggttgaggc cgttgagcac    2760
cgccgccgca aggaatggtg catgcaagga gatggcgccc aacagtcccc cggccacggg    2820
gcctgccacc atacccacgc cgaaacaagc gctcatgagc ccgaagtggc gagcccgatc    2880
ttccccatcg gtgatgtcgg cgatataggc gccagcaacc gcacctgtgg cgccggtgat    2940 gccggcacg atgcgtccgg cgtagaggat ccggagctta tcgactgcac ggtgcaccaa     3000
tgcttctggc gtcaggcagc catcggaagc tgtggtatgg ctgtgcaggt cgtaaatcac    3060
tgcataattc gtgtcgctca aggcgcactc ccgttctgga taatgttttt tgcgccgaca    3120
tcataacggt tctggcaaat attctgaaat gagctgttga caattaatca tcggctcgta    3180
taatgtgtgg aattgtgagc ggataacaat ttcacacagg aaacagaatt caaattctat    3240
ttcaaggaga caggatccat atggcgaaac ttccggatgc gagctcccag attcgtcaga    3300
attattctac tgaagtggag gccgccgtca accgcctggt caacctgtac ctgcgggcct    3360
cctacaccta cctctctctg gcttctattt cgaccgcga cgatgtggct ctggagggcg     3420
tatgccactt cttccgcgag ttggcggagg agaagcgcga gggtgccgag cgtctcttga    3480
agatgcaaaa ccagcgcggc ggccgcgccc tcttccagga cttgcagaag ccgtcccagg    3540
atgaatgggg tacaaccccg gatgccatga agccgccat tgtcctggag aagagcctga     3600
accaggccct tttggatctg catgcccctgg gttctgccca ggcagacccc catctctgtg   3660
acttcttgga gagccacttc ctagacgagg aggtgaaact catcaagaag atgggcgacc    3720
atctgaccaa catccagagg ctcgttggct cccaagctgg gctgggcgag tatctctttg    3780
aaaggctcac tctcaagcac gactaagtcg acctgcaggc atgcaagctt              3830
```

<210> SEQ ID NO 5
<211> LENGTH: 12
<212> TYPE: PRT
<213> ORGANISM: Artificial
<220> FEATURE:
<223> OTHER INFORMATION: Twelve amino acids for alignment of ferritin
    on substrate (Prior Art).
<220> FEATURE:
<221> NAME/KEY: MISC_FEATURE
<222> LOCATION: (1)..(12)
<223> OTHER INFORMATION: of SEQ ID NO: 5: amino acid sequence including
    12 residues for arraying ferritin described in Langmuir, Vol. 23,
    pp. 1615-1618, (2007) on a substrate

<400> SEQUENCE: 5

Asp Tyr Phe Ser Ser Pro Tyr Tyr Glu Gln Leu Phe
1               5                   10

<210> SEQ ID NO 6
<211> LENGTH: 174
<212> TYPE: PRT
<213> ORGANISM: horse

<400> SEQUENCE: 6

Ser Ser Gln Ile Arg Gln Asn Tyr Ser Thr Glu Val Glu Ala Ala Val
1               5                   10                  15

Asn Arg Leu Val Asn Leu Tyr Leu Arg Ala Ser Tyr Thr Tyr Leu Ser
            20                  25                  30

Leu Gly Phe Tyr Phe Asp Arg Asp Asp Val Ala Leu Glu Gly Val Cys
        35                  40                  45

```
His Phe Phe Arg Glu Leu Ala Glu Glu Lys Arg Gly Ala Glu Arg
        50                  55                  60

Leu Leu Lys Met Gln Asn Gln Arg Gly Gly Arg Ala Leu Phe Gln Asp
 65                  70                  75                  80

Leu Gln Lys Pro Ser Gln Asp Glu Trp Gly Thr Thr Pro Asp Ala Met
                 85                  90                  95

Lys Ala Ala Ile Val Leu Glu Lys Ser Leu Asn Gln Ala Leu Leu Asp
            100                 105                 110

Leu His Ala Leu Gly Ser Ala Gln Ala Asp Pro His Leu Cys Asp Phe
        115                 120                 125

Leu Glu Ser His Phe Leu Asp Glu Val Lys Leu Ile Lys Lys Met
    130                 135                 140

Gly Asp His Leu Thr Asn Ile Gln Arg Leu Val Gly Ser Gln Ala Gly
145                 150                 155                 160

Leu Gly Glu Tyr Leu Phe Glu Arg Leu Thr Leu Lys His Asp
                165                 170

<210> SEQ ID NO 7
<211> LENGTH: 12
<212> TYPE: PRT
<213> ORGANISM: Artificial
<220> FEATURE:
<223> OTHER INFORMATION: Twelve amino acids for E10S-Fer0
<220> FEATURE:
<221> NAME/KEY: MISC_FEATURE
<222> LOCATION: (1)..(12)
<223> OTHER INFORMATION: of SEQ ID NO: 7: amino acid sequence including
      12 residues for producing E10S-Fer0

<400> SEQUENCE: 7

Asp Tyr Phe Ser Ser Pro Tyr Tyr Ser Gln Leu Phe
 1               5                  10

<210> SEQ ID NO 8
<211> LENGTH: 12
<212> TYPE: PRT
<213> ORGANISM: Artificial
<220> FEATURE:
<223> OTHER INFORMATION: Twelve amino acids for D2N-Fer0
<220> FEATURE:
<221> NAME/KEY: MISC_FEATURE
<222> LOCATION: (1)..(12)
<223> OTHER INFORMATION: of SEQ ID NO: 8: amino acid sequence including
      12 residues for producing D2N-Fer0

<400> SEQUENCE: 8

Asn Tyr Phe Ser Ser Pro Tyr Tyr Glu Gln Leu Phe
 1               5                  10

<210> SEQ ID NO 9
<211> LENGTH: 12
<212> TYPE: PRT
<213> ORGANISM: Artificial
<220> FEATURE:
<223> OTHER INFORMATION: Twelve amino acids for E10Q-Fer0
<220> FEATURE:
<221> NAME/KEY: MISC_FEATURE
<222> LOCATION: (1)..(12)
<223> OTHER INFORMATION: of SEQ ID NO: 9: amino acid sequence including
      12 residues for producing E10Q-Fer0

<400> SEQUENCE: 9

Asp Tyr Phe Ser Ser Pro Tyr Tyr Glu Gln Leu Phe
 1               5                  10
```

```
<210> SEQ ID NO 10
<211> LENGTH: 12
<212> TYPE: PRT
<213> ORGANISM: Artificial
<220> FEATURE:
<223> OTHER INFORMATION: Twelve amino acids for P7S-Fer0
<220> FEATURE:
<221> NAME/KEY: MISC_FEATURE
<222> LOCATION: (1)..(12)
<223> OTHER INFORMATION: of SEQ ID NO: 10: amino acid sequence including
      12 residues for producing P7S-Fer0

<400> SEQUENCE: 10

Asp Tyr Phe Ser Ser Ser Tyr Tyr Glu Gln Leu Phe
1               5                   10

<210> SEQ ID NO 11
<211> LENGTH: 12
<212> TYPE: PRT
<213> ORGANISM: Artificial
<220> FEATURE:
<223> OTHER INFORMATION: Twelve amino acids for Shuffle-Fer0.
<220> FEATURE:
<221> NAME/KEY: MISC_FEATURE
<222> LOCATION: (1)..(12)
<223> OTHER INFORMATION: of SEQ ID NO: 11: amino acid sequence including
      12 residues for producing Shuffle-Fer0

<400> SEQUENCE: 11

Phe Gln Tyr Leu Tyr Ser Tyr Pro Phe Glu Ser Asp
1               5                   10

<210> SEQ ID NO 12
<211> LENGTH: 12
<212> TYPE: PRT
<213> ORGANISM: Artificial
<220> FEATURE:
<223> OTHER INFORMATION: Twelve amino acids for S5T-S6T-Fer0.
<220> FEATURE:
<221> NAME/KEY: MISC_FEATURE
<222> LOCATION: (1)..(12)
<223> OTHER INFORMATION: of SEQ ID NO: 12: amino acid sequence including
      12 residues for producing S5T-S6T-Fer0

<400> SEQUENCE: 12

Asp Tyr Phe Thr Thr Pro Tyr Tyr Glu Gln Leu Phe
1               5                   10

<210> SEQ ID NO 13
<211> LENGTH: 12
<212> TYPE: PRT
<213> ORGANISM: Artificial
<220> FEATURE:
<223> OTHER INFORMATION: Twelve amino acids for DeltaAR-Fer0.
<220> FEATURE:
<221> NAME/KEY: MISC_FEATURE
<222> LOCATION: (1)..(12)
<223> OTHER INFORMATION: of SEQ ID NO: 13: amino acid sequence including
      12 residues for producing Delta AR-Fer0

<400> SEQUENCE: 13

Asp Ser Ala Ser Ser Pro Ser Ser Glu Gln Leu Ala
1               5                   10

<210> SEQ ID NO 14
<211> LENGTH: 12
<212> TYPE: PRT
<213> ORGANISM: Artificial
<220> FEATURE:
<223> OTHER INFORMATION: Twelve amino acids for Y8F-Y9F-Fer0.
<220> FEATURE:
```

```
<221> NAME/KEY: MISC_FEATURE
<222> LOCATION: (1)..(12)
<223> OTHER INFORMATION: of SEQ ID NO: 14: amino acid sequence including
      12 residues for producing Y8F-Y9F-Fer0

<400> SEQUENCE: 14

Asp Tyr Phe Ser Ser Pro Phe Phe Glu Gln Leu Phe
1               5                   10

<210> SEQ ID NO 15
<211> LENGTH: 12
<212> TYPE: PRT
<213> ORGANISM: Artificial
<220> FEATURE:
<223> OTHER INFORMATION: Twelve amino acids for DeltaHY-Fer0.
<220> FEATURE:
<221> NAME/KEY: MISC_FEATURE
<222> LOCATION: (1)..(12)
<223> OTHER INFORMATION: of SEQ ID NO: 15: amino acid sequence including
      12 residues for producing DeltaHY-Fer0

<400> SEQUENCE: 15

Asp Phe Phe Ala Ala Pro Phe Phe Glu Gln Leu Phe
1               5                   10

<210> SEQ ID NO 16
<211> LENGTH: 6
<212> TYPE: PRT
<213> ORGANISM: Artificial
<220> FEATURE:
<223> OTHER INFORMATION: Six amino acids for 1st half-Fer0.
<220> FEATURE:
<221> NAME/KEY: MISC_FEATURE
<222> LOCATION: (1)..(6)
<223> OTHER INFORMATION: of SEQ ID NO: 16: amino acid sequence including
      6 residues for producing 1st half-Fer0

<400> SEQUENCE: 16

Asp Tyr Phe Ser Ser Pro
1               5

<210> SEQ ID NO 17
<211> LENGTH: 6
<212> TYPE: PRT
<213> ORGANISM: Artificial
<220> FEATURE:
<223> OTHER INFORMATION: Six amino acids for 2nd half-Fer0.
<220> FEATURE:
<221> NAME/KEY: MISC_FEATURE
<222> LOCATION: (1)..(6)
<223> OTHER INFORMATION: of SEQ ID NO: 17: amino acid sequence including
      6 residues for producing 2nd half-Fer0

<400> SEQUENCE: 17

Tyr Tyr Glu Gln Leu Phe
1               5

<210> SEQ ID NO 18
<211> LENGTH: 5
<212> TYPE: PRT
<213> ORGANISM: Artificial
<220> FEATURE:
<223> OTHER INFORMATION: Five amino acids for 5AA-Fer0.
<220> FEATURE:
<221> NAME/KEY: MISC_FEATURE
<222> LOCATION: (1)..(5)
<223> OTHER INFORMATION: of SEQ ID NO: 18: amino acid sequence including
      5 residues for producing 5AA-Fer0

<400> SEQUENCE: 18
```

Asp Tyr Ser Ser Tyr
1               5

<210> SEQ ID NO 19
<211> LENGTH: 36
<212> TYPE: DNA
<213> ORGANISM: Artificial
<220> FEATURE:
<223> OTHER INFORMATION: DNA sequence for Y6S4DE.
<220> FEATURE:
<221> NAME/KEY: misc_feature
<222> LOCATION: (1)..(36)
<223> OTHER INFORMATION: of SEQ ID NO: 19: DNA corresponding to peptide
      Y6S4DE

<400> SEQUENCE: 19
gattattatt cgagctcgta ttatgaatat tattct                                36

<210> SEQ ID NO 20
<211> LENGTH: 36
<212> TYPE: DNA
<213> ORGANISM: Artificial
<220> FEATURE:
<223> OTHER INFORMATION: DNA sequence for E10S.
<220> FEATURE:
<221> NAME/KEY: misc_feature
<222> LOCATION: (1)..(36)
<223> OTHER INFORMATION: of SEQ ID NO: 20: DNA corresponding to peptide
      E10S

<400> SEQUENCE: 20
gattatttct cgagcccgta ttattcacag ctgttt                                36

<210> SEQ ID NO 21
<211> LENGTH: 36
<212> TYPE: DNA
<213> ORGANISM: Artificial
<220> FEATURE:
<223> OTHER INFORMATION: DNA sequence for D2N.
<220> FEATURE:
<221> NAME/KEY: misc_feature
<222> LOCATION: (1)..(36)
<223> OTHER INFORMATION: of SEQ ID NO: 21: DNA corresponding to peptide
      D2N

<400> SEQUENCE: 21
aattatttct cgagcccgta ttatgaacag ctgttt                                36

<210> SEQ ID NO 22
<211> LENGTH: 36
<212> TYPE: DNA
<213> ORGANISM: Artificial
<220> FEATURE:
<223> OTHER INFORMATION: DNA sequence for E10Q.
<220> FEATURE:
<221> NAME/KEY: misc_feature
<222> LOCATION: (1)..(22)
<223> OTHER INFORMATION: of SEQ ID NO: 22: DNA corresponding to peptide
      E10Q

<400> SEQUENCE: 22
gattatttct cgagcccgta ttatcagcag ctgttt                                36

<210> SEQ ID NO 23
<211> LENGTH: 36
<212> TYPE: DNA
<213> ORGANISM: Artificial
<220> FEATURE:
<223> OTHER INFORMATION: DNA sequence for P7S.
<220> FEATURE:

```
<221> NAME/KEY: misc_feature
<222> LOCATION: (1)..(36)
<223> OTHER INFORMATION: of SEQ ID NO: 23: DNA corresponding to peptide
      P7S

<400> SEQUENCE: 23
gattatttct cgagctcgta ttatgaacag ctgttt                              36

<210> SEQ ID NO 24
<211> LENGTH: 36
<212> TYPE: DNA
<213> ORGANISM: Artificial
<220> FEATURE:
<223> OTHER INFORMATION: DNA sequence for Shuffle.
<220> FEATURE:
<221> NAME/KEY: misc_feature
<222> LOCATION: (1)..(36)
<223> OTHER INFORMATION: of SEQ ID NO: 24: DNA corresponding to peptide
      Shuffle

<400> SEQUENCE: 24
ttccagtatc tgtattcgta tccgtttgaa agcgat                              36

<210> SEQ ID NO 25
<211> LENGTH: 36
<212> TYPE: DNA
<213> ORGANISM: Artificial
<220> FEATURE:
<223> OTHER INFORMATION: DNA sequence for S5T-S6T.
<220> FEATURE:
<221> NAME/KEY: misc_feature
<222> LOCATION: (1)..(36)
<223> OTHER INFORMATION: of SEQ ID NO: 25: DNA corresponding to peptide
      S5T-S6T

<400> SEQUENCE: 25
gattatttca ctactccgta ttatgaacag ctgttt                              36

<210> SEQ ID NO 26
<211> LENGTH: 36
<212> TYPE: DNA
<213> ORGANISM: Artificial
<220> FEATURE:
<223> OTHER INFORMATION: DNA sequence for DeltaAR.
<220> FEATURE:
<221> NAME/KEY: misc_feature
<222> LOCATION: (1)..(36)
<223> OTHER INFORMATION: of SEQ ID NO: 26: DNA corresponding to peptide
      DeltaAR

<400> SEQUENCE: 26
gattcggctt cgagcccgtc gtcggaacag ctggct                              36

<210> SEQ ID NO 27
<211> LENGTH: 36
<212> TYPE: DNA
<213> ORGANISM: Artificial
<220> FEATURE:
<223> OTHER INFORMATION: DNA sequence for Y8F-Y9F.
<220> FEATURE:
<221> NAME/KEY: misc_feature
<222> LOCATION: (1)..(36)
<223> OTHER INFORMATION: of SEQ ID NO: 27: DNA corresponding to peptide
      Y8F-Y9F

<400> SEQUENCE: 27
gattatttct cgagcccgtt ttttgaacag ctgttt                              36

<210> SEQ ID NO 28
```

```
<211> LENGTH: 36
<212> TYPE: DNA
<213> ORGANISM: Artificial
<220> FEATURE:
<223> OTHER INFORMATION: DNA sequence for DeltaHY.
<220> FEATURE:
<221> NAME/KEY: misc_feature
<222> LOCATION: (1)..(36)
<223> OTHER INFORMATION: of SEQ ID NO: 28: DNA corresponding to peptide
      DeltaHY

<400> SEQUENCE: 28
gattttttcg ccgccccgtt ttttgaacag ctgttt                              36

<210> SEQ ID NO 29
<211> LENGTH: 18
<212> TYPE: DNA
<213> ORGANISM: Artificial
<220> FEATURE:
<223> OTHER INFORMATION: DNA sequence for 1st half.
<220> FEATURE:
<221> NAME/KEY: misc_feature
<222> LOCATION: (1)..(18)
<223> OTHER INFORMATION: of SEQ ID NO: 29: DNA corresponding to peptide
      1st half

<400> SEQUENCE: 29
gattatttct cgagcccg                                                  18

<210> SEQ ID NO 30
<211> LENGTH: 18
<212> TYPE: DNA
<213> ORGANISM: Artificial
<220> FEATURE:
<223> OTHER INFORMATION: DNA sequence for 2nd half.
<220> FEATURE:
<221> NAME/KEY: misc_feature
<222> LOCATION: (1)..(18)
<223> OTHER INFORMATION: of SEQ ID NO: 30: DNA corresponding to peptide
      2nd half

<400> SEQUENCE: 30
tattatgaac agctgttt                                                  18

<210> SEQ ID NO 31
<211> LENGTH: 15
<212> TYPE: DNA
<213> ORGANISM: Artificial
<220> FEATURE:
<223> OTHER INFORMATION: DNA sequence for 5AA.
<220> FEATURE:
<221> NAME/KEY: misc_feature
<222> LOCATION: (1)..(15)
<223> OTHER INFORMATION: of SEQ ID NO: 31: DNA corresponding to peptide
      5AA

<400> SEQUENCE: 31
gattattcga gctat                                                     15
```

METHOD OF TWO-DIMENSIONALLY ARRAYING FERRITIN ON SUBSTRATE

BACKGROUND OF THE INVENTION

1. Field of the Invention

The present invention relates to a method of two-dimensionally arraying ferritin on a substrate.

2. Description of Related Art

Ferritin is a spherical protein that includes a metal compound therein which is typified by iron oxide. When any metal compound is not included therein but has a hollow space inside, ferritin is referred to as "apoferritin".

Quantum dots of a metal that is two-dimensionally arrayed on a substrate can be readily obtained by two-dimensionally arraying ferritin on the substrate followed by removing the ferritin by heating, and reducing metal oxide if necessary. Therefore, two-dimensionally arraying ferritin on a substrate was reported as shown in FIG. 1 (for example, see Pamphlet of International Publication No. 03/040025 and Langmuir, Vol. 23, pp. 1615-1618, (2007)).

SUMMARY OF THE INVENTION

According to the method disclosed in Pamphlet of International Publication No. 03/040025, as shown in FIG. 87, a bivalent metal ion (in FIG. 87, cadmium ion) serves in crosslinkage between adjacent two particles of ferritin 15. After ferritin is removed by heating, this bivalent metal ion remains on the substrate as an impurity. The impurity is supposed to migrate on the substrate in the form of an ion, therefore, an unexpected interface state may be generated due to such an impurity in the quantum dots composed of a two-dimensional array of a metal on a substrate. As a consequence, the impurity adversely affects the quantum dots.

According to the method of Pamphlet of International Publication No. 03/040025, a two-dimensional crystal is formed without using a bivalent metal ion; however, it is necessary to allow a particular peptide (carbon nano material-recognizing peptide, SEQ ID NO: 5) to be presented to the external surface of ferritin, as shown in FIG. 88.

The present invention provides a method of two-dimensionally arraying ferritin on a substrate without such adverse influences.

DETAILED DESCRIPTION OF PREFERRED EMBODIMENTS

Figure 1:
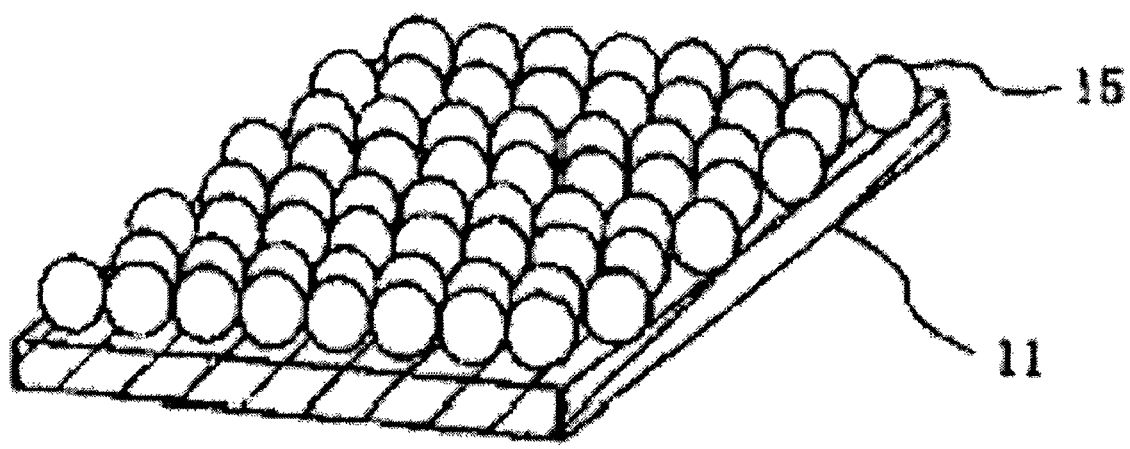
FIG. 1 shows a schematic view illustrating a state which multiple particles of ferritin form a two-dimensional array on a substrate (FIG. 8 in Pamphlet of International Publication No. 03/040025).

In order to solve the aforementioned problems, the present invention provides a method of two-dimensionally arraying ferritin on a substrate, wherein the surface of the substrate is hydrophilic, the method comprising the steps of:

developing a solution containing a solvent and the ferritin on the substrate, and removing the solvent from the solution developed on the substrate, wherein the ferritin has an amino acid sequence set out in SEQ ID NO: 1 modified at its N-terminus.

The surface of the substrate is preferably covered by $SiO_2$.

The solution preferably includes at least one of PIPES (piperazine-1,4-bis(2-ethanesulfonic acid)), ammonium sulfate, and ammonium acetate.

When the solution includes PIPES, the concentration is preferably not lower than 5 mM and not higher than 50 mM.

In addition, when the solution includes ammonium sulfate, the concentration is preferably not lower than 6.5 mM and not higher than 52 mM.

Moreover, when the solution includes ammonium acetate, the concentration is preferably not lower than 2 mM and not higher than 100 mM.

The solution is preferably adjusted to have a pH falling within the range of not lower than 6.0 and not higher than 8.0.

According to the present invention, there exists no metal ion for binding between adjacent two ferritin particles. Therefore, adverse influences typified by appearance of unexpected interface state on the quantum dot provided by two-dimensionally arraying a metal on a substrate can be suppressed.

Hereinafter, the present invention is described in more detail.

The ferritin which may be used in the present invention has an amino acid sequence represented by: DYYSSSYYEYYS (hereinafter, SEQ ID NO: 1) on the outer peripheral surface. As one example, ferritin used in the present invention is a protein set out in SEQ ID NO: 2. This protein has 187 residues, in which an amino acid sequence of 13 residues that include methionine corresponding to an initiation codon and the amino acid sequence of SEQ ID NO: 1 was added to an amino acid sequence (SEQ ID NO: 6) of ferritin derived from horse having 174 residues at its amino terminal.

In Experimental Examples described later, ferritin used in the present invention is designated as "Y6S4DE-Fer0". In the case of apoferritin, the designation is made as "apoY6S4DE-Fer0". In Experimental Examples described later, other apoferritin is also designated with the name of ferritin preceded by a representation "apo".

Conventional ferritin does not have the amino acid sequence set out in SEQ ID NO: 1. In a conventional example of the ferritin (see, Langmuir, Vol. 23, pp. 1615-1618, (2007)), an amino acid sequence of 13 residues that include methionine corresponding to an initiation codon and a peptide sequence: DYFSSPYYEQLF (SEQ ID NO: 5) is added to an amino acid sequence (SEQ ID NO: 6) of ferritin derived from horse having 174 residues at its amino terminal. As will be also comprehended from Comparative Example described later, the two-dimensional array on a substrate cannot be effected even though conventional ferritin modified at random in the amino acid sequence corresponding to SEQ ID NO: 5 is used. In Experimental Example described later, the conventional ferritin is designated as "N1-LF".

The term "two-dimensional array" as used herein means an array as shown in the schematic view of FIG. 1, in which multiple particles of ferritin 15 are arranged regularly on substrate 11 viewed in a plane, and a single-layered ferritin film is formed by the multiple particles of ferritin 15 viewed in a cross section.

Figure 2:
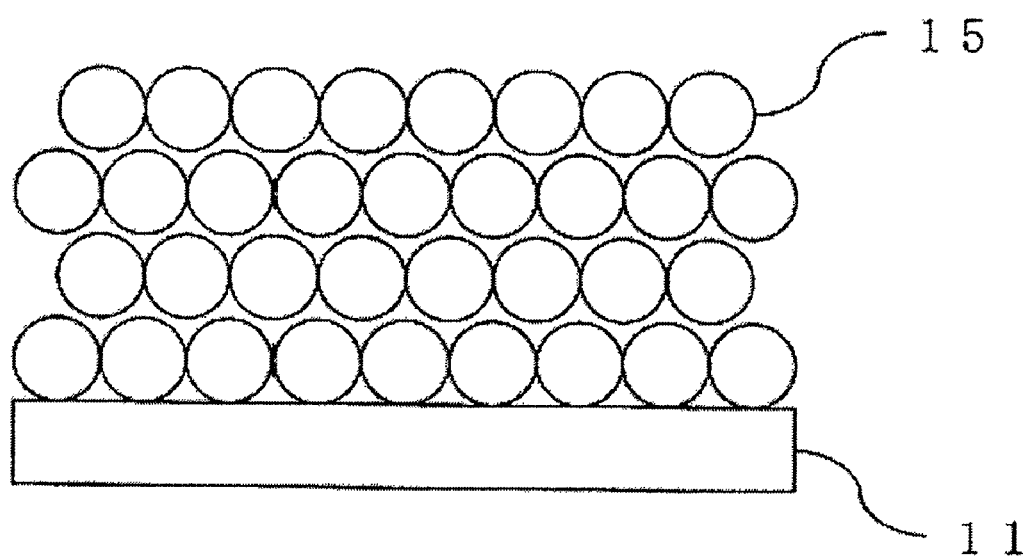
FIG. 2 shows a cross-sectional view of a three-dimensional array.

The array in which a ferritin film including two or more layers as shown in the cross-sectional view of FIG. 2 is not involved in the term "two-dimensional array". Such an array is referred to as "three-dimensional array" as needed, which is herein distinguished from the term "two-dimensional array". However, to exclude also the case of the single layered ferritin film that includes a three-dimensional array just in part (i.e., locally) from the term "two-dimensional array" is not intended.

Figure 3:
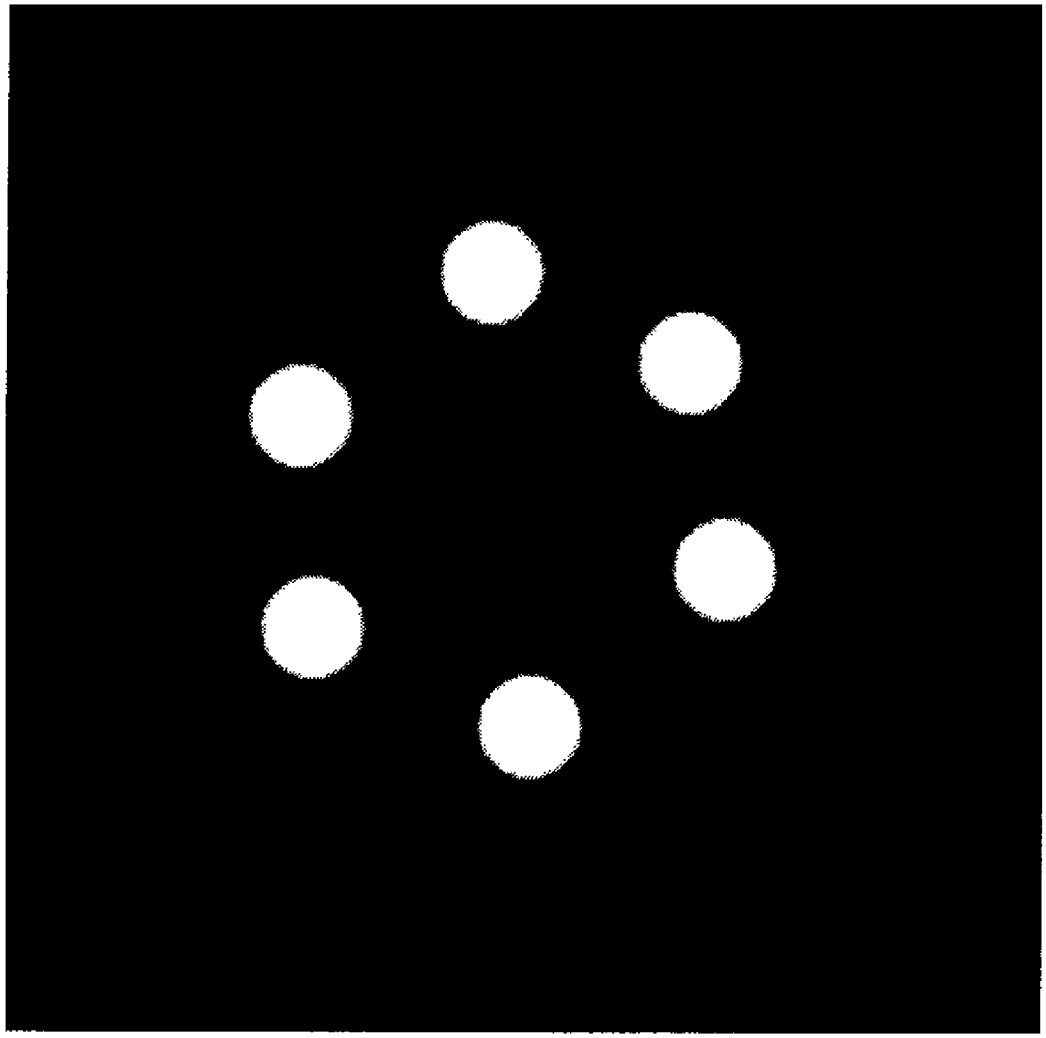
FIG. 3 shows a schematic view illustrating a Fourier transformation image obtained by two-dimensional Fourier transformation.

In the method of evaluating "two-dimensional array" herein, an SEM observation image (300 nm×300 nm) including ferritin is subjected to two-dimensional Fourier transformation, and the resulting Fourier transformation image is used. The two-dimensional array in the state of hexagonal closest packing as shown in the schematic view of FIG. 1 has been known to be capable of approximating to overlapping three sinusoidal waves oriented differently by 60 degrees, respectively. In the Fourier transformation image of the two-dimensional array described above, six points corresponding to the three sinusoidal waves appear as shown in FIG. 3. Each point is located at a position provided in rotating 60 degrees each around the point at which the wave number is zero. When the aforementioned approximation is not established (i.e., no two-dimensional array being present), the six points do not appear in the Fourier transformation image.

Figure 4:
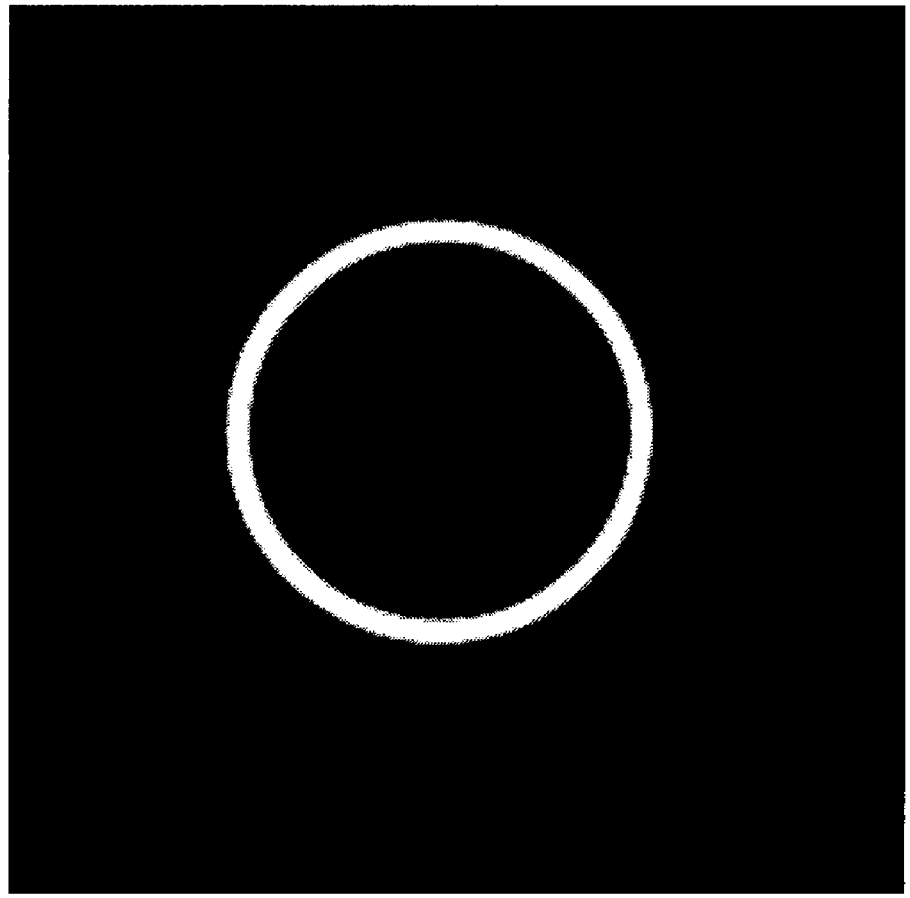
FIG. 4 shows a schematic view illustrating a Fourier transformation image obtained by two-dimensional Fourier transformation.

In the case in which the periodicity of the two-dimensional array shown in the schematic view of FIG. 1 was disorganized (i.e., the case in which the two-dimensional array was deteriorated), or in the case of polycrystalline in which the two-dimensional array was constituted with not monocrystals composed of single crystal alone but multiple crystal grain aggregates, the distinct six points would not appear in the Fourier transformation image, but the points corresponding just to the number of differently oriented polycrystallines appear along the concentric circle, or otherwise a circular pattern may appear as shown in FIG. 4 in an extreme case. Therefore, the case in which distinct six points appear as shown in the schematic view of FIG. 3 is evaluated as "favorable two-dimensional array"; the case in which a "two-dimensional array" is involved in an original SEM observation image but distinct six points do not appear therein as shown in the schematic view of FIG. 4 is evaluated as "inferior two-dimensional array"; and other cases are evaluated as "two-dimensional array not formed".

The surface of the substrate is hydrophilic. An Si substrate can be used as the substrate.

The hydrophilicity can be imparted to the surface by oxidizing the surface of the Si substrate to give $SiO_2$. In this case, the surface of the substrate has a slightly negative potential.

The method of two-dimensionally arraying ferritin on a substrate according to the present invention has a development step and a removal step. The development step is explained first.

(1) Development Step

In the development step, a solution that contains a solvent, the ferritin, and 12.5 mM PIPES-NaOH (pH 7.0), 12.5 mM PIPES-Tris (pH 7.0), 13 mM ammonium sulfate (($NH_4)_2SO_4$), or 20 mM ammonium acetate ($CH_3CO_2NH_4$) is developed on the substrate. When PIPES (weakly acidic) is to be used as the buffer, the pH is adjusted with NaOH (thus prepared buffer is referred to as "PIPES-NaOH"). Since a metal ion can be an impurity in the present invention, to employ a weakly alkaline buffer, the pH of which is adjusted with an acid such as HCl is more desired.

Specific examples of the process for the development also include the following processes in addition to the process of dropwise addition of the solution on the substrate. More specifically, the solution is added dropwise on a thin film typified by Parafilm, and then the substrate is calmly placed on the solution with the hydrophilic face down. In other words, the solution is sandwiched between the thin film typified by Parafilm, and the substrate with the hydrophilic face down.

(2) Removal Step

Next, the removal step is explained. In the removal step, the solvent is removed from the solution developed on the substrate. Because the solution is typically a buffer, the solvent will be almost water accounting for a major portion of the buffer. Hence, the process for removing water from the substrate is explained in this section.

Specific examples of the process for removing the solvent include a process in which the substrate is subjected to centrifugal separation, as well as a process in which the solvent is evaporated from the substrate, and the like. In light of rapid removal of the solvent, the process in which the substrate is subjected to centrifugal separation is preferred. In any case, the process is acceptable as long as water is removed from the substrate in the removal step, which may include drying and concentration, irrespective of the procedure.

In the manner described above, ferritin can be two-dimensionally arrayed on the substrate. When a quantum dot is to be obtained, in general, thus two-dimensionally arrayed ferritin is heated to eliminate the protein on the external side, and the metal oxide is further reduced as needed, whereby the quantum dot formed by two-dimensionally arraying the metal on the substrate can be readily obtained.

Also, it should be noted that the metal can be substituted with a compound semiconductor (see, pamphlet of International Publication No. 03/099008).

EXAMPLES

Hereinafter, the present invention will be explained in more detail with reference to Experimental Examples.

In the present Experimental Example, the reagents presented in Table 1 below were used.

TABLE 1

| Abbreviated name | Trade name | Cat. No. | Lot No. | |
| --- | --- | --- | --- | --- |
| Nde I | Nde I | R0111L | | New England Biolabs |
| Sac I | Sac I | R0156L | | New England Biolabs |
| x 10 NEB 4 buffer | x 10 NEB 4 buffer | | | New England Biolabs |
| Tris | Trizma base | 76066-500G | 025K5432 | SIGMA-ALDRICH |
| HEPES | HEPES | 342-01375 | SF076 | Dojindo Laboratories |
| AIS | Ammonium iron (II) sulfate hexahydrate | 091-00855 | CEK7339 | Wako Pure Chemical Industries, Ltd. |
| Indium sulfate | Indium (III) sulfate | 20020-32 | 408C2100 | Wako Pure Chemical Industries, Ltd. |

TABLE 1-continued

| Abbreviated name | Trade name | Cat. No. | Lot No. | |
|---|---|---|---|---|
| $NaH_2PO_4$ | Disodium hydrogenphosphate (anhydride) | 197-09705 | CEJ1855 | Wako Pure Chemical Industries, Ltd. |
| $NH_3$ | 1 mol/L Aqueous ammonia (1N) | 01793-08 | | KANTO CHEMICAL CO., INC. |
| Ammonium sulfate | Ammonium Sulfate 99.999% | 204501-50G | 06810PB | SIGMA-ALDRICH |
| Ammonium acetate | Ammonium acetate | 019-02835 | | Wako Pure Chemical Industries, Ltd. |
| PIPES | PIPES BioUltra, for molecular biology, ≧99.5% (T) | 80635-250G | | Fluka |

In the present Experimental Example, ferritin having an amino acid sequence including a peptide sequence consisting of the amino acid sequence shown in Table 2 below and methionine corresponding to an initiation codon introduced to an amino acid sequence (SEQ ID NO: 6) of ferritin derived from horse having residues at its amino terminal was used. The DNA sequence corresponding to each amino acid sequence is as listed in Table 2. In the present Experimental Example, each ferritin is designated as "peptide name-Fer0".

TABLE 2

| Peptide name | Amino acid sequence | DNA sequence (5' → 3') |
|---|---|---|
| Y6S4DE | DYYSSSYYEYYS (SEQ ID NO: 1) | GAT TAT TAT TCG AGC TCG TAT TAT GAA TAT TAT TCT (SEQ ID NO: 19) |
| E10S | DYFSSPYYSQLF (SEQ ID NO: 7) | GAT TAT TTC TCG AGC CCG TAT TAT TCA CAG CTG TTT (SEQ ID NO: 20) |
| D2N | NYFSSPYYEQLF (SEQ ID NO: 8) | AAT TAT TTC TCG AGC CCG TAT TAT GAA CAG CTG TTT (SEQ ID NO: 21) |
| E10Q | DYFSSPYYQQLF (SEQ ID NO: 9) | GAT TAT TTC TCG AGC CCG TAT TAT CAG CAG CTG TTT (SEQ ID NO: 22) |
| P7S | DYFSSSYYEQLF (SEQ ID NO: 10) | GAT TAT TTC TCG AGC TCG TAT TAT GAA CAG CTG TTT (SEQ ID NO: 23) |
| Shuffle | FQYLYSYPFESD (SEQ ID NO: 11) | TTC CAG TAT CTG TAT TCG TAT CCG TTT GAA AGC GAT (SEQ ID NO: 24) |
| S5T-S6T | DYFTTPYYEQLF (SEQ ID NO: 12) | GAT TAT TTC ACT ACT CCG TAT TAT GAA CAG CTG TTT (SEQ ID NO: 25) |
| ΔAR | DSASSPSSEQLA (SEQ ID NO: 13) | GAT TCG GCT TCG AGC CCG TCG TCG GAA CAG CTG GCT (SEQ ID NO: 26) |
| Y8F-Y9F | DYFSSPFFEQLF (SEQ ID NO: 14) | GAT TAT TTC TCG AGC CCG TTT TTT GAA CAG CTG TTT (SEQ ID NO: 27) |
| ΔHY | DFFAAPFFEQLF (SEQ ID NO: 15) | GAT TTT TTC GCC GCC CCG TTT TTT GAA CAG CTG TTT (SEQ ID NO: 28) |
| 1st half | DYFSSP (SEQ ID NO: 16) | GAT TAT TTC TCG AGC CCG (SEQ ID NO: 29) |
| 2nd half | YYEQLF (SEQ ID NO: 17) | TAT TAT GAA CAG CTG TTT (SEQ ID NO: 30) |
| 5AA | DYSSY (SEQ ID NO: 18) | GAT TAT TCG AGC TAT (SEQ ID NO: 31) |

Preparation 1

Construction of Protein Expression Vector

First, a procedure for constructing a protein expression vector is illustrated in the following.

1. A solution of a plasmid vector pKIS9 (SEQ ID NO: 4) for protein expression was prepared. If necessary, the plasmid vector was isolated and purified from *Escherichia coli* carrying the plasmid vector (see, also QIAprep_Miniprep Protocol and Trouble Shooting available from QIAGEN).

2. An absorbance of the plasmid solution at a wavelength involving 260 nm was measured with a UV/VIS spectrometer (ND-1000, NanoDrop Technologies, LLC) to determine the concentration of DNA.

3. To 1.5 ml Eppendorf tube which had been subjected to autoclave sterilization were added 2 μL of ×10 NEB 4 buffer, 15 μL of a 148 ng/μL pKIS9 plasmid DNA solution (TE Buffer (10 mM Tris-HCl (pH 8.0), 1 mM EDTA), 1 μL of a Sac I solution, and 1 μL of a Nde I solution. Thus resulting solution was mixed by pipetting, and allowed to react at 37° C. for 1 hour.

4. The reaction mixture was electrophoresed on 2% (w/v) agarose gel, and the target plasmid DNA fragment was separated and extracted from the agarose gel (see, also MinElute Gel Extraction Kit Protocol and Trouble Shooting available from QIAGEN).

5. An absorbance of the DNA fragment solution at a wavelength involving 260 nm was measured with a UV/VIS spectrometer (ND-1000, NanoDrop Technologies, LLC) to determine the concentration of DNA.

6. A single strand oligo DNA was synthesized in by adding an Nde I restriction enzyme cleavage site the 5' end and a SaI restriction enzyme cleavage site was the 3' end of a DNA sequence encoding a desired amino acid sequence. Concomitantly, an oligo DNA complementary to the aforementioned single strand oligo DNA was synthesized. The single strand oligo DNA was obtained from Sigma Genosys or Takara Bio Inc.

7. Each same volume of 10 μL of 5 μM single strand oligo DNA solution to be inserted and 5 μM complementary DNA chain solution were mixed, and annealed at 95° C. for 3 min. Thereafter, the mixture was cooled at room temperature to produce a double strand oligo DNA having an Nde I/Sac I site at the end.

8. A pKIS9 plasmid DNA fragment and a double strand oligo DNA were joined to produce a plasmid vector for protein expression (each for expression of ferritin) (see, Manual of DNA Ligation System DNA Ligation Kit Ver. 2.1, available from TaKaRa).

Preparation 2-1

Large Scale Expression and Purification of Y6S4DE-Fer0

First, synthesis and purification procedures of apo Y6S4DE-Fer0 are shown below. The synthesis and purification procedures of Shuffle-Fer0, D2N-Fer0, E10Q-Fer0, E10S-Fer0, P7S-Fer0, HY-Fer0, $2^{nd}$ half-Fer0, Y8F-Y9F-Fer0, S5T-S6T-Fer0, and NF-LF are also similar except that the N-terminal region of the used plasmid vectors for protein expression has each base sequence shown in Table 2.

1. A plasmid vector for protein expression (SEQ ID NO: 3) was introduced into *Escherichia coli* XL1-blue (NOVAGENE) to perfect the transformation (see, also ECOS TM Competent *E. coli* DH5α, JM109, XL1-Blue, BL21 (DE3) Manual (ver. 6) available from NIPPON GENE CO., LTD.).

2. A colony of the transformed *Escherichia coli* was subjected to shaking culture (apparatus: TAITEC Bio Shaker BR-40LF, preset temperature: 37° C., culture period: 5 to 7 hrs, shaking speed: 120 rpm) in 1 ml of an LB medium (containing 50 μg/ml ampicillin) charged in a 15-ml sterilized Corning tube.

3. The aforementioned culture solution (0.1 to 0.5 ml) was subjected to shaking culture in 50 ml of an LB medium (containing 50 μg/ml ampicillin) in a 500-ml Erlenmeyer flask at 37° C. for 16 to 20 hrs.

4. The turbidity of the medium was measured with a spectrophotometer (Ultrospec 3100 pro, GE Healthcare Bioscience). At a time point when it reached to OD600: 0.1 to 0.5, 50 ml of the aforementioned culture solution was subjected to a spinner culture (apparatus: ABLE BMS-10/05, preset temperature: 37° C., shaking speed: 200 rpm, air flow rate: 4 L/min, culture period: 18 to 20 hrs) in 6 L of an LB medium (containing 100 μg/ml ampicillin).

5. The turbidity of the medium was measured, and after OD600 of 4.0 to 5.0 was ascertained, the bacterial body was harvested with a low-speed centrifuge (Model: Avanti HP-25, rotorModel: JA-10, BECKMAN, preset temperature: 4° C., preset number of revolutions: 8,000 rpm, time: 10 min) in a centrifuge tube for JA-10.

6. Thus harvested bacterial body was suspended in 50 mM Tris-HCl (200 ml to 300 ml), and collected in a centrifuge tube for JA-10 low-speed centrifuge (similarly to the above section 5).

7. The harvested bacterial body was suspended in 50 mM Tris-HCl (120 ml), placed in ice, and the cells were disrupted with an ultrasonic disintegrator (apparatus: Branson Digital Sonifier 450, preset output value: 140 W, pulse setting: on/off 1 sec, disintegration time: 2 min×3).

8. The mixture was centrifuged with a low-speed centrifuge (Model: Avanti HP-25, rotor Model: JA-20, BECKMAN, preset temperature: 4° C., preset centrifugal force: 6,000×g, time: 10 min), and the supernatant was collected.

9. The collected supernatant was subjected to a heat treatment (75° C., 20 min), and was left to stand at room temperature following the heat treatment until the temperature dropped to an ordinary temperature (approximately for 1 hour).

10. The supernatant was centrifuged with a low-speed centrifuge (similar to the above section 8), and the supernatant was collected.

11. To thus collected supernatant was added 5 M NaCl to give a final concentration of 0.5 M NaCl, and then suspended.

12. The suspension was centrifuged with a low-speed centrifuge (similar to the above section 8), and the precipitate was collected.

13. The collected precipitate was suspended in 50 mM Tris-HCl (120 ml), and thereto was added 10.54 ml of 5 M NaCl to give a final concentration of 0.4 M NaCl. Thus resulting mixture was suspended.

14. The suspension was centrifuged with a low-speed centrifuge (similar to the above section 8), and the precipitate was collected.

15. After the precipitate was collected, the operations of 13 to 14 were repeated again.

16. The precipitate was suspended in 50 mM Tris-HCl (60 ml), and passed through a 0.22-μm syringe filter to complete the purification.

Preparation 2-2

Large Scale Expression and Purification of apoΔAR-Fer0

First, synthesis and purification procedures of apoΔAR-Fer0 are shown below. The synthesis and purification procedures of $1^{st}$ half-Fer0, and 5AA-Fer0 are also similar except that the N-terminal region of the used plasmid vectors for protein expression has each base sequence shown in Table 2.

1. A plasmid vector for protein expression was introduced into *Escherichia coli* XL1-blue (NOVAGENE) to perfect the transformation (see, also ECOS TM Competent *E. coli* DH5α, JM109, XL1-Blue, BL21 (DE3) Manual (ver. 6) available from NIPPON GENE CO., LTD.).

2. A colony of the transformed *Escherichia coli* was subjected to shaking culture (apparatus: TAITEC Bio Shaker BR-40LF, preset temperature: 37° C., culture period: 5 to 7 hrs, shaking speed: 120 rpm) in 1 ml of an LB medium (containing 50 μg/ml ampicillin) charged in a 15-ml sterilized Corning tube.

3. The aforementioned culture solution (0.1 to 0.5 ml) was subjected to shaking culture in 50 ml of an LB medium (containing 50 μg/ml ampicillin) in a 500-ml Erlenmeyer flask at 37° C. for 16 to 20 hrs.

4. The turbidity of the medium was measured with a spectrophotometer (Ultrospec 3100 pro, GE Healthcare Bioscience). At a time point when it reached to OD600: 0.1 to 0.5, 50 ml of the aforementioned culture solution was subjected to a spinner culture (apparatus: ABLE BMS-10/05, preset temperature: 37° C., shaking speed: 200 rpm, air flow rate: 4 L/min, culture period: 18 to 20 hrs) in 6 L of an LB medium (containing 100 µg/ml ampicillin).

5. The turbidity of the medium was measured, and after OD600 of 4.0 to 5.0 was ascertained, the bacterial body was harvested with a low-speed centrifuge (Model: Avanti HP-25, rotorModel: JA-10, BECKMAN, preset temperature: 4° C., preset number of revolutions: 8,000 rpm, time: 10 min) in a centrifuge tube for JA-10.

6. Thus harvested bacterial body was suspended in 50 mM Tris-HCl (200 ml to 300 ml), and collected in a centrifuge tube for JA-10 low-speed centrifuge (similarly to the above section 5).

7. The harvested bacterial body was suspended in 50 mM Tris-HCl (120 ml), placed in ice, and the cells were disrupted with an ultrasonic disintegrator (apparatus: Branson Digital Sonifier 450, preset output value: 140 W, pulse setting: on/off 1 sec, disintegration time: 2 min×3).

8. The mixture was centrifuged with a low-speed centrifuge (Model: Avanti HP-25, rotor Model: JA-20, BECKMAN, preset temperature: 4° C., preset centrifugal force: 6,000×g, time: 10 min), and the supernatant was collected.

9. The collected supernatant was subjected to a heat treatment (75° C., 20 min), and was left to stand at room temperature following the heat treatment until the temperature dropped to an ordinary temperature (approximately for 1 hour).

10. The supernatant was centrifuged with a low-speed centrifuge (similar to the above section 8), and the supernatant was collected.

11. However, when the disrupted product does not precipitate sufficiently, it was centrifuged with a low-speed centrifuge (Model: Avanti HP-25, rotorModel: JA-20, BECKMAN, preset temperature: 4° C., preset centrifugal force: 15,000×g, time: 10 min), and the supernatant was collected.

12. The disruption supernatant was filtrated with a 0.22 µm filter (MilieX-GV Cat. No. SLGV033RS, Millipore) to give a filtrate 1.

13. An anion exchange column HiLoad-26/10 Q Sepharose-HP (GE Healthcare) was connected to an HPLC system for protein purification (AKTA explorer 10S, GE Healthcare).

14. Using 50 mM Tris-HCl buffer, pH 8.0 as a starting mobile phase (buffer A), 400 ml or more of the buffer was fed at a flow rate of 7.0 ml per min beforehand.

15. The aforementioned filtrate 1 was charged in a sample loop, and injected into the column at a flow rate of 7 ml per min.

16. Using 50 mM Tris-HCl buffer, pH 8.0 as a starting mobile phase (buffer A), 400 ml or more of the buffer was fed at a flow rate of 7.0 ml per min to remove the unabsorbed fraction.

17. Using 50 mM Tris-HCl buffer, pH 8.0 containing 1 M NaCl as a gradient mobile phase (buffer B), elution of the protein fraction was performed with gradient from 10 to 60% of the mixing ratio with the buffer A with ten times volume (530.93 ml) of the column bed volume (53.093 ml).

18. The target protein was eluted at around a mixing ratio of approximately 30%.

19. From each fraction involving the mixing ratio of 30%, 10 µL of an aliquot was taken, and SDS-PAGE was performed using an SDS-PAGE gel at an acrylamide concentration of 12.5%.

20. The target protein fraction was determined by SDS-PAGE, and the fraction was transferred to a ultrafiltration apparatus (Centriprep YM30, Millipore).

21. The Centriprep YM30 was placed into a swing rotor of a centrifuge (LC-200 TOMY, preset temperature: 4° C.).

22. The fraction was concentrated by repeating the centrifugal separation at 3,000 rpm until the volume of the solution left in the collection tube was reduced to no greater than 3 ml.

23. The concentrated solution was taken from the collection tube.

24. When the purity of the target protein was more inferior as compared with the purification procedure shown in Preparation 2-1, gel filtration was performed by the following procedure.

25. A Tricorn 10/600 column (GE Healthcare) packed with a TSK-GEL BIOASSIST G4SWXL resin (Tosoh Corporation) was connected to a general-purpose HPLC system (8020 series Tosoh Corporation).

26. Using 50 mM Tris-HCl buffer, pH 8.0 containing 150 mM NaCl as a mobile phase, 100 ml or more of the buffer was fed at a flow rate of 0.5 ml per min beforehand.

27. The concentrated solution 1 of not more than 3 ml was charged in a sample loop, and injected into the column at a flow rate of 0.5 ml per min.

28. Monitoring was carried out with a UV/VIS detector (UV-8020 Tosoh Corporation) at a wavelength of 280 nm, and the results were recorded using a software (LC-8020 Model IITosoh Corporation) installed in PC for regulation.

29. The eluate was collected each 1.0 ml with a fraction collector (FC-8020 Tosoh Corporation), and the fraction including the target protein was collected.

30. The concentration of thus resulting protein solution was unknown.

Preparation 3

Determination of Protein Concentration

The concentration of the protein solution obtained by the aforementioned large-scale expression and purification (for example, solution containing apoY6S4DE0-Fer0) was unknown. Thus, the concentration of the protein solution having an unknown concentration was measured according to the following method.

The determination of the protein concentration was carried out according to a Lowry method using a DC protein assay kit (Cat. No. 500-0112JA, BioRad).

1. As a standard protein, a solution of BSA (Bovine Albumin Serum, Cat. No. 23209 PIERCE) having a known concentration diluted with ultrapure water to give certain concentrations (0.2, 0.4, 0.6, 1.0, 2.0 mg/ml) was used.

2. The reaction mixture was produced by the following procedure. The protein solution (or ultrapure water as a control) in a volume of 25 µl and 125 µl of the reagent A were charged in a microtube and mixed.

3. Subsequently, 1 ml of the reagent B was charged in the same microtube and mixed, and then the reaction was allowed at room temperature, 25 (±1)° C. for not shorter than 15 min.

4. After completing the reaction, the absorbance was measured within one hour at a wavelength of 750 nm with a spectrophotometer (Ultrospec 3100 pro, GE Healthcare Bioscience).

5. The absorbance at 750 nm of the BSA solutions was plotted with respect to the protein concentration, and a formula of:

(Protein concentration of unknown sample)=$A$ (Absorbance of unknown sample at 750 nm)+$C$ was derived by a least square method.

6. The protein concentration of an arbitrarily diluted sample solutions was determined according to the aforementioned procedure, and the determined protein concentration was multiplied by the dilution ratio to derive the concentration of the sample stock solution. Thus derived protein concentration (concentration of apoY6S4DE-Fer0 included in the solution) was 2.5 mg/ml.

Preparation 4

Purity Test of Apoferritin

With respect to the purity of the resulting apoferritin (for example, apoY6S4DE-Fer0) whether or not it is suited for core synthesis, a test was carried out by the following procedure.

The purity was determined by the gel filtration as in the following.

1. A general-purpose HPLC system (8020 series Tosoh Corporation) to which a TSK-GEL BIOASSIST G4SWXL column was connected (Tosoh Corporation) was used.

2. Using a 50 mM Tris-HCl buffer, pH 8.0 as a mobile phase, 50 ml or more of the buffer was fed at a flow rate of 1.0 ml per min beforehand.

3. The purified solution having a concentration of 1 mg/ml of 0.1 ml was charged in a sample loop, and injected into the column at a flow rate of 1.0 ml per min.

4. Monitoring was carried out with a UV/VIS detector (UV-8020 Tosoh Corporation) at a wavelength of 280 nm, and the results were recorded using a software (LC-8020 Model IITosoh Corporation) installed in PC for regulation.

5. It was ascertained that the peak corresponding to the ferritin subunit included in the sample (elution time: 13 to 14 min) was not beyond the detection level, and was only the peak derived from apoferritin (monomer: 8.6 min, dimer: 7.8 min).

Preparation 5

Synthesis of Ferritin Including Indium

Indium oxide used for producing a two-dimensional array was synthesized in side apoferritin (for example, apoY6S4DE-Fer0) as follows.

In this Example, 80 ml of a reaction mixture was prepared according to the following procedure to give the final composition of the solution of: 0.2 M disodium hydrogenphosphate, 12 mM ammonia, 40 mM HCl, 0.1 mg/ml apoY6S4DE-Fer0, and 1 mM indium sulfate.

1. To a 125-ml square medium bottle (Nalge Nunc 2019-0125) were added 16 ml of 1 M disodium hydrogenphosphate, 0.96 ml of 1 M ammonia, 3.2 ml of 1 N HCl and 56.64 ml of ultrapure water in this order, and the mixture was stirred with a stirrer.

2. The pH was measured with a pH meter and ascertained that the mixture had a pH of 2.88 (within ±0.02).

3. 3.2 ml of a 2 mM Tris (pH 8.0) solution containing 2.5 mg/ml apoY6S4DE-Fer0 was added thereto, and the mixture was stirred with a stirrer.

4. Thereto was added 41.4 mg of indium sulfate powder, and the powder was dissolved in the reaction mixture.

5. The square medium bottle charged with the reaction mixture was sealed with a cap, and the reaction was allowed while stirring at 25° C. (±1° C.) for 3 hours.

6. After completing the reaction, each 40 ml of the reaction mixture was dispensed in a 50-ml Falcon tube.

7. The Falcon tube was placed in a swing rotor for a centrifuge LC-200 (TOMY), and centrifuged at 3,000 rpm for 10 min. Thus, supernatant 1 was eliminated to collect precipitate 1.

8. To the precipitate 1 was added 5 ml of a 50 mM Tris-HCl buffer (pH 8.0), and suspended with a vortex mixer.

9. The Falcon tube including the precipitate 1 was placed in a swing rotor for the centrifuge LC-200, and centrifuged at 3,000 rpm for 10 min to obtain supernatant 2 and precipitate 2. The supernatant 2 was dispensed in a new Falcon tube.

10. To the precipitate 2 was added 5 ml of the 50 mM Tris-HCl buffer (pH 8.0), and suspended with a vortex mixer.

11. The Falcon tube including the precipitate 2 was placed in a swing rotor for the centrifuge LC-200, and centrifuged at 3,000 rpm for 10 min to obtain supernatant 2 and precipitate 2. The supernatant 2 was dispensed in a new Falcon tube.

12. To the precipitate 2' was added 5 ml of a 50 mM Tris-HCl buffer (pH 8.0), and suspended with a vortex mixer.

13. The Falcon tube including the precipitate 2' was placed in a swing rotor for the centrifuge LC-200, and centrifuged at 3,000 rpm for 10 min to obtain supernatant 2" and precipitate 2". The supernatant 2" was dispensed in a new Falcon tube.

14. To each of the supernatant 2 (about 5 ml), the supernatant 2' (about 5 ml), and the supernatant 2" (about 5 ml) was added 0.5 ml of 5M NaCl, and the Falcon tube was inverted to allow for stirring.

15. The Falcon tube was placed in a swing rotor for the centrifuge LC-200, and centrifuged at 3,000 rpm for 10 min. Thus, supernatant 3, supernatant 3' and supernatant 3" were eliminated to collect precipitate 3, precipitate 3' and precipitate 3".

16. To the precipitate 3 was added 10 ml of a 50 mM Tris-HCl buffer (pH 8.0), and suspended with a vortex mixer to obtain suspension 3.

17. To the precipitate 3' was added the suspension 3, and suspended with a vortex mixer to obtain suspension 3'.

18. To the precipitate 3" was added 10 ml of the suspension 3', and suspended with a vortex mixer to obtain suspension 3".

19. To the suspension 3" (about 10 ml) was added 0.9 ml of 5 M NaCl, and the Falcon tube was inverted to allow for stirring.

20. The Falcon tube was placed in a swing rotor for the centrifuge LC-200, and centrifuged at 3,000 rpm for 10 min. Thus, supernatant 4 was eliminated to collect precipitate 4.

21. To the precipitate 4 was added 10 ml of the 50 mM Tris-HCl buffer (pH 8.0), and suspended with a vortex mixer to obtain suspension 4.

22. Suspension 5 was transferred to a collection tube of an Apollo 20-ml (QMWL 150 kDa) centrifugal concentrator.

23. The Apollo 20-ml centrifugal concentrator was placed in a swing rotor of the centrifuge LC-200, and the centrifugal separation was repeated at 3,000 rpm to concentrate until the volume of the solution left in the collection tube was reduced to not more than 1 ml.

24. Concentrated solution 1 was taken from the collection tube.

25. In the procedure shown in "Preparation 3: Determination of Protein Concentration" described above, the concentration of Y6S4DE-Fer0 (hereinafter, designated as Y6S4DE-Fer0 (In)) having indium oxide as a core was determined. In the description hereinbelow, ferritin having indium oxide as a core is represented by adding a denotation of (In) to the end of the name of the ferritin.

Preparation 6

High Level of Purification of X-Fer0 (In)

For the two-dimensional regular arraying, highly pure ferritin (monomer purity: not less than 99.5%) having an indium oxide core inside (hereinafter, designated as X-Fer0 (In), wherein X represents a peptide name such as Y6S4DE) is desired.

Accordingly, X-Fer0 (In) for use in the two-dimensional regular arraying was highly purified in this Example as shown below.

1. Tricorn 10/600 column (GE Healthcare) packed with TSK-GEL BIOASSIST G4SWXL resin (Tosoh Corporation) was connected to a general-purpose HPLC system (8020 series Tosoh Corporation).
2. Using a 50 mM Tris-HCl buffer, pH 8.0 as a mobile phase, 100 ml or more of the buffer was fed at a flow rate of 0.5 ml per min beforehand.
3. The concentrated solution 1 of not more than 3 ml was charged in a sample loop, and injected into the column at a flow rate of 0.5 ml per min.
4. Monitoring was carried out with a UV/VIS detector (UV-8020 Tosoh Corporation) at a wavelength of 280 nm, and the results were recorded using a software (LC-8020 Model IITosoh Corporation) installed in PC for regulation.
5. Each 1.0-ml fraction of the eluate was collected with a fraction collector (FC-8020 Tosoh Corporation), thereby collecting the fraction containing the X-Fer0 (In) monomer.
6. In the procedure shown in "Preparation 3: Determination of Protein Concentration" described above, the concentration of X-Fer0 (In) was determined.

Preparation 7

Preparation of Substrate

A substrate having a hydrophilic surface for use in the two-dimensional arraying of the present invention is prepared.

Thermally Oxidized Silicon Substrate

A procedure for removing organic matters on the surface by a UV/ozone treatment (washing with ultraviolet ray/ozone) is demonstrated below.

1. Just before (i.e., immediately before allowing for two-dimensionally arraying of ferritin as described later), a thermally oxidized silicon substrate ($SiO_2$ membrane having a thickness of 3 nm) was cut into a piece having a size of 5×10 mm.
2. Using an apparatus (Model UV-1, SAMCO Inc.), the thermally oxidized silicon substrate was subjected to an UV/ozone treatment under conditions at a substrate temperature of 110° C. and an oxygen flow rate of 0.5 L/min for a washing time of 10 min.

Two-Dimensional Arraying of Ferritin

After completing the foregoing Preparations 1 to 7, ferritin was two-dimensionally arrayed according to the following procedure (hereinafter, may be referred to as "sandwich method").

1. A protein/2 mM Tris buffer having a concentration twice of the final concentration was prepared. For example, in the case of Y6S4DE-Fer0 (In) in which the final concentration was to be 0.5 mg/ml, 1.0 mg/ml Y6S4DE-Fer0 (In) was prepared.
2. A solution for arraying having a concentration two times of the final concentration was prepared. For example, in the case of ammonium sulfate in which the final concentration was to be 13 mM, a 26 mM ammonium sulfate solution was prepared.
3. Each 5 µl of the protein solution and a crystallization solution was charged in a micro test tube, and mixed by pipetting or with a Vortex mixer.
4. An appropriate size of Parafilm was provided in a plastic dish, and 5 µl of the mixed solution was dropped on the Parafilm.
5. The substrate prepared according to "Preparation 7: Preparation of Substrate" was provided such that the droplet was brought into contact with its surface subjected to a hydrophilizing treatment.
6. The plastic dish was covered by a lid, and left to stand still in an incubator (LTI-2000, Tokyo Rikakikai Co., LTD.) at 20 (±0.5)° C. for 30 min.
7. After the lapse of a predetermined time period, the substrate was peeled off from the Parafilm with vacuum tweezers, and transferred into a 1.5-ml micro test tube.
8. The micro test tube was centrifuged with a centrifuge (5415D, Eppendorf Co., Ltd.) at 1500 G for 10 min, and an excess solution on the substrate was removed.
9. The substrate was removed from the micro test tube, and SEM (JEOL SEM7400F) observation was carried out. The observation condition involved an accelerating voltage of 5 kV, and an emission electric current of 10 µA.

The results are as shown below.

Example 1

Figure 5:
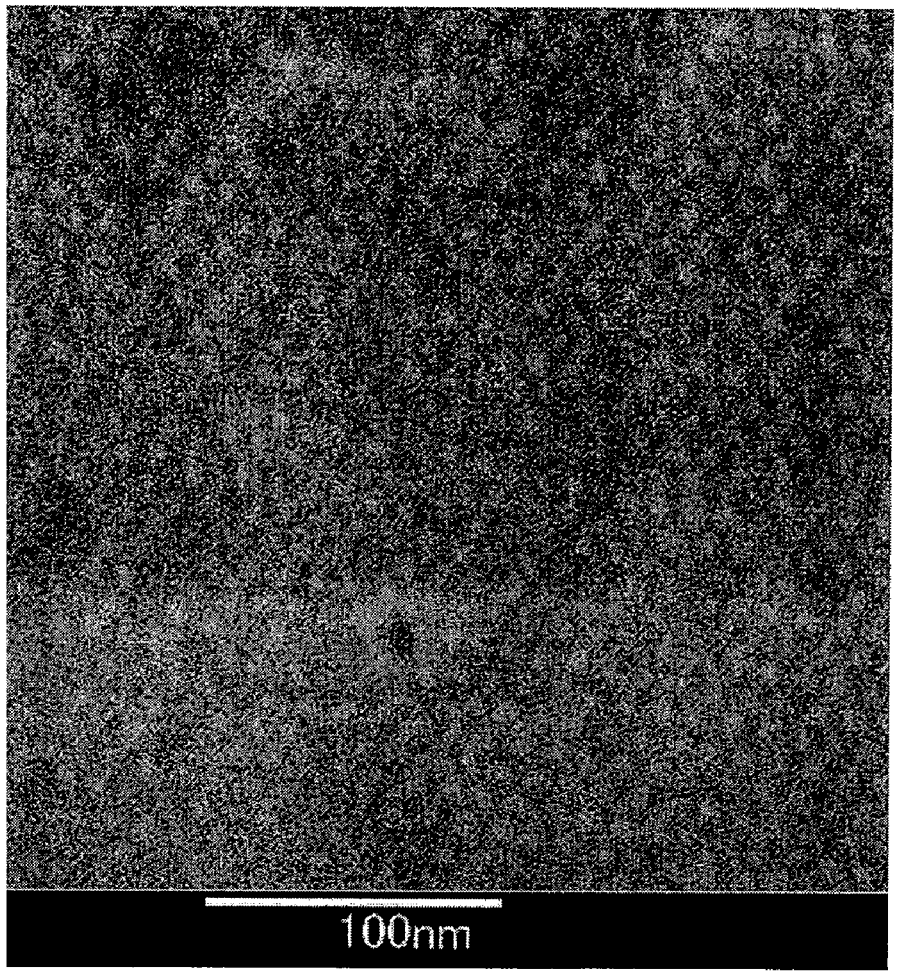
FIG. 5 shows a photograph illustrating the appearance of a two-dimensional array of ferritin obtained in Example 1.
Figure 6:
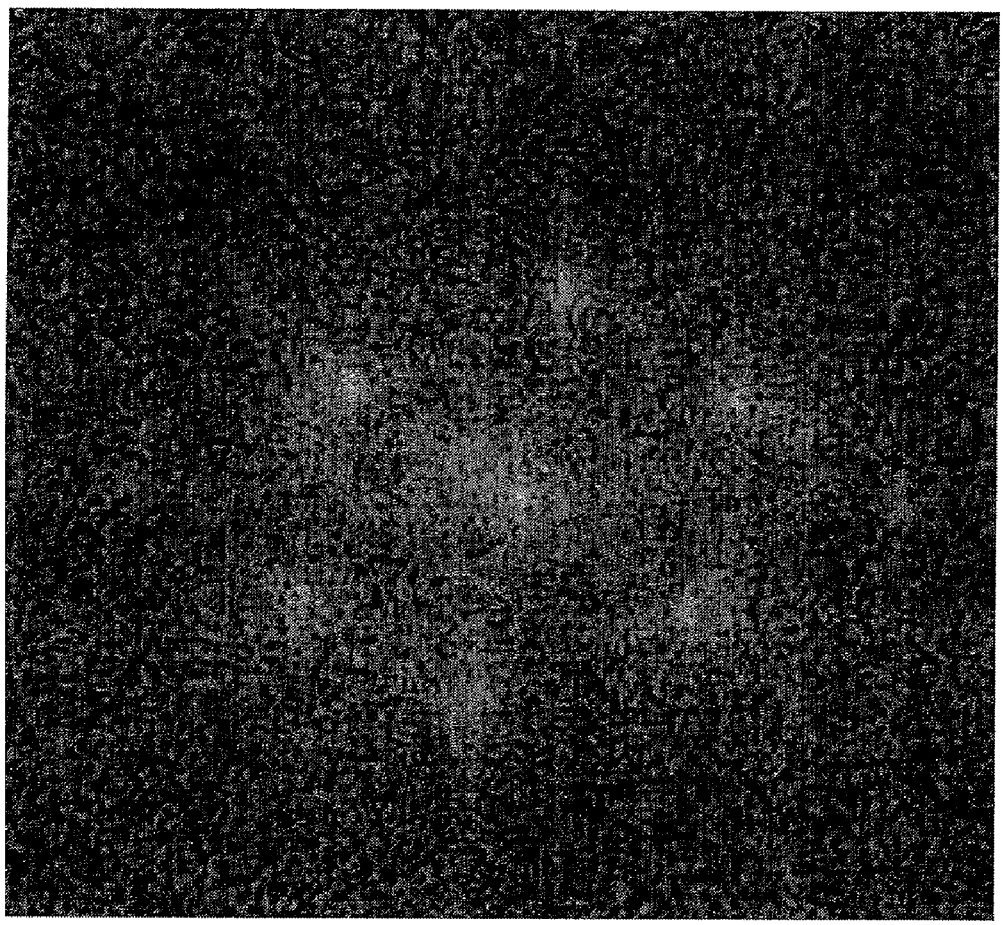
FIG. 6 shows a photograph of Fourier transformation image illustrating the appearance of a two-dimensional array of ferritin obtained in Example 1.

A photograph illustrating the appearance of a two-dimensional array of ferritin obtained using 0.5 mg/ml Y6F4DE-Fer0 (In) and 12.5 mM PIPES-NaOH (pH 7.0) is shown in FIG. 5, and a Fourier transformation image thereof is shown in FIG. 6.

Example 2

Figure 7:
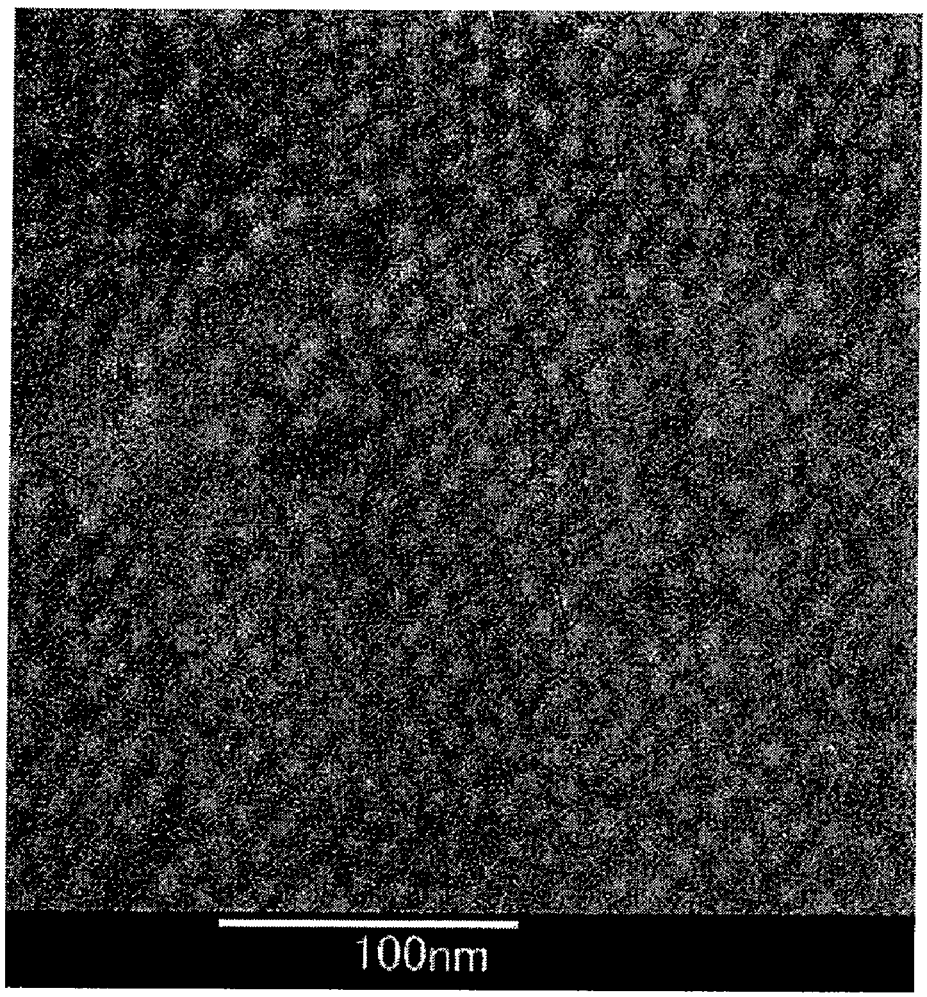
FIG. 7 shows a photograph illustrating the appearance of a two-dimensional array of ferritin obtained in Example 2.
Figure 8:
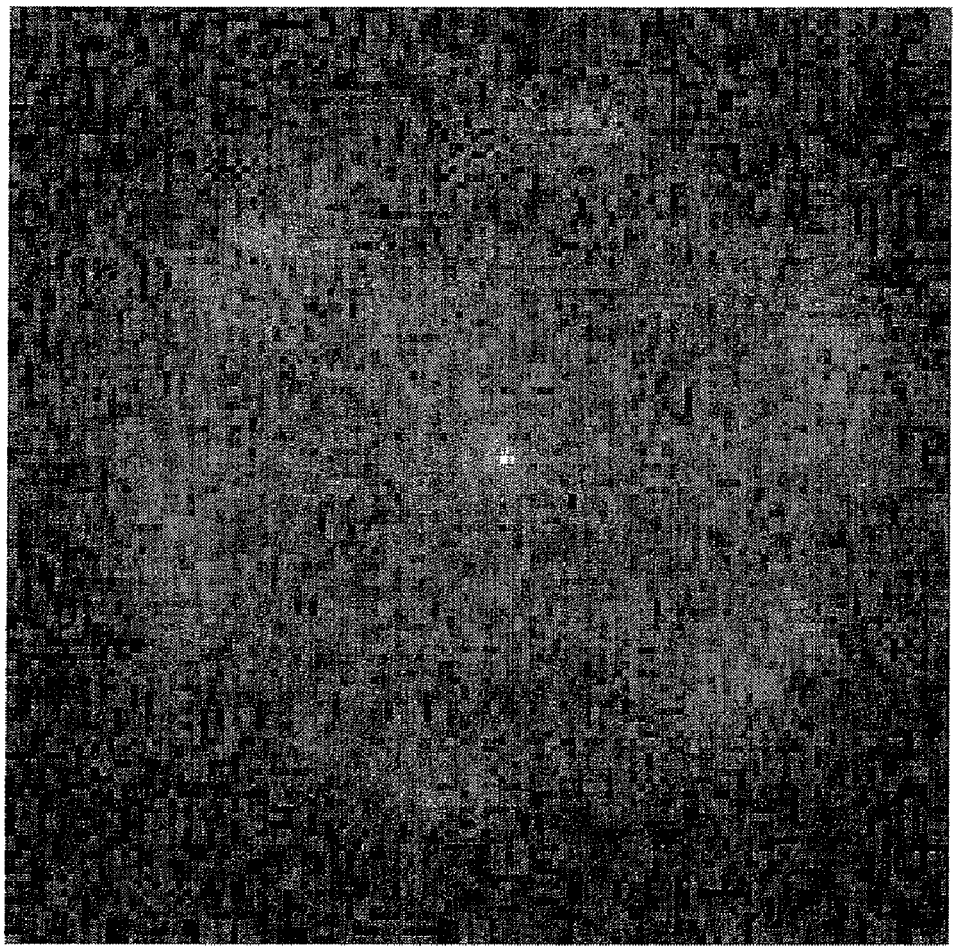
FIG. 8 shows a photograph of Fourier transformation image illustrating the appearance of a two-dimensional array of ferritin obtained in Example 2.

A photograph illustrating the appearance of a two-dimensional array of ferritin obtained using 0.5 mg/ml Y6F4DE-Fer0 (In) and 12.5 mM PIPES-Tris (pH 7.0) is shown in FIG. 7, and a Fourier transformation image thereof is shown in FIG. 8.

Example 3

Figure 9:
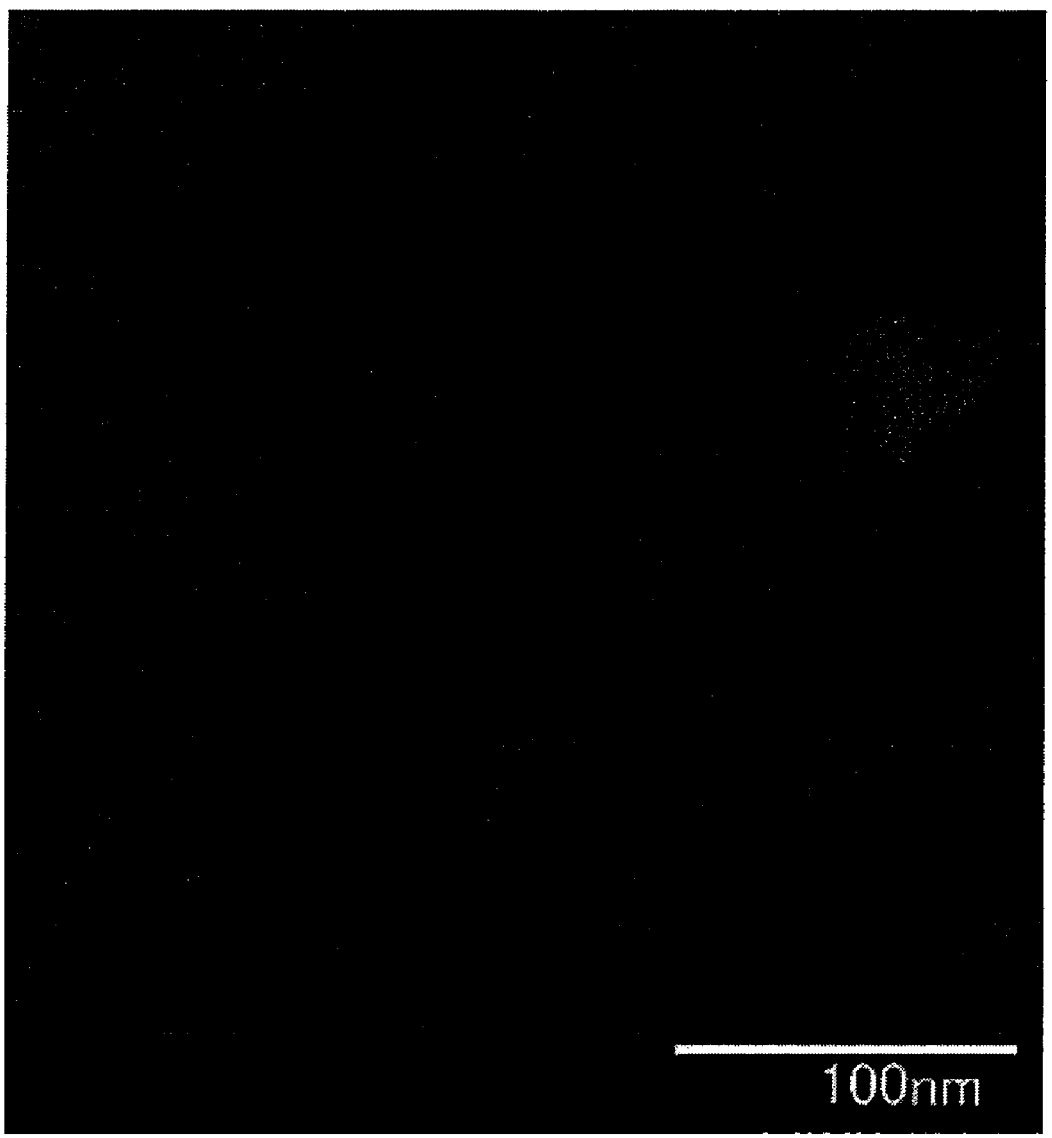
FIG. 9 shows a photograph illustrating the appearance of a two-dimensional array of ferritin obtained in Example 3.
Figure 10:
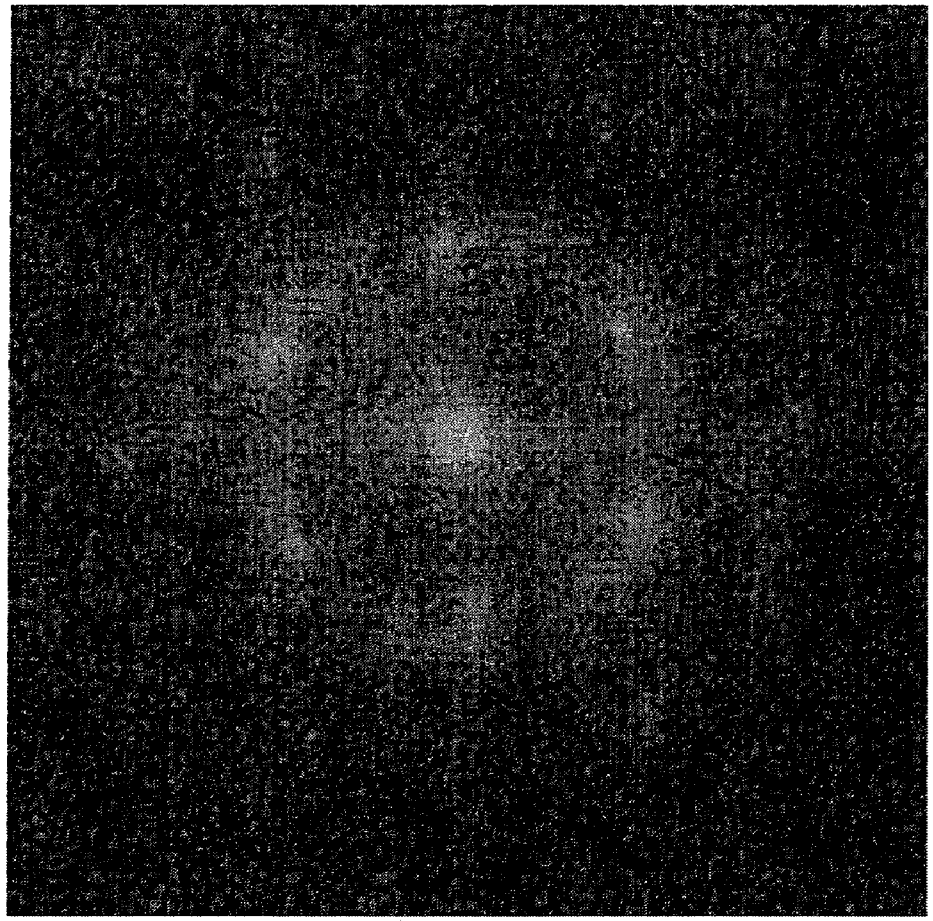
FIG. 10 shows a photograph of Fourier transformation image illustrating the appearance of a two-dimensional array of ferritin obtained in Example 3.

A photograph illustrating the appearance of a two-dimensional array of ferritin obtained using 0.5 mg/ml Y6F4DE-Fer0 (In) and 13 mM ammonium sulfate is shown in FIG. 9, and a Fourier transformation image thereof is shown in FIG. 10.

Example 4

Figure 11:
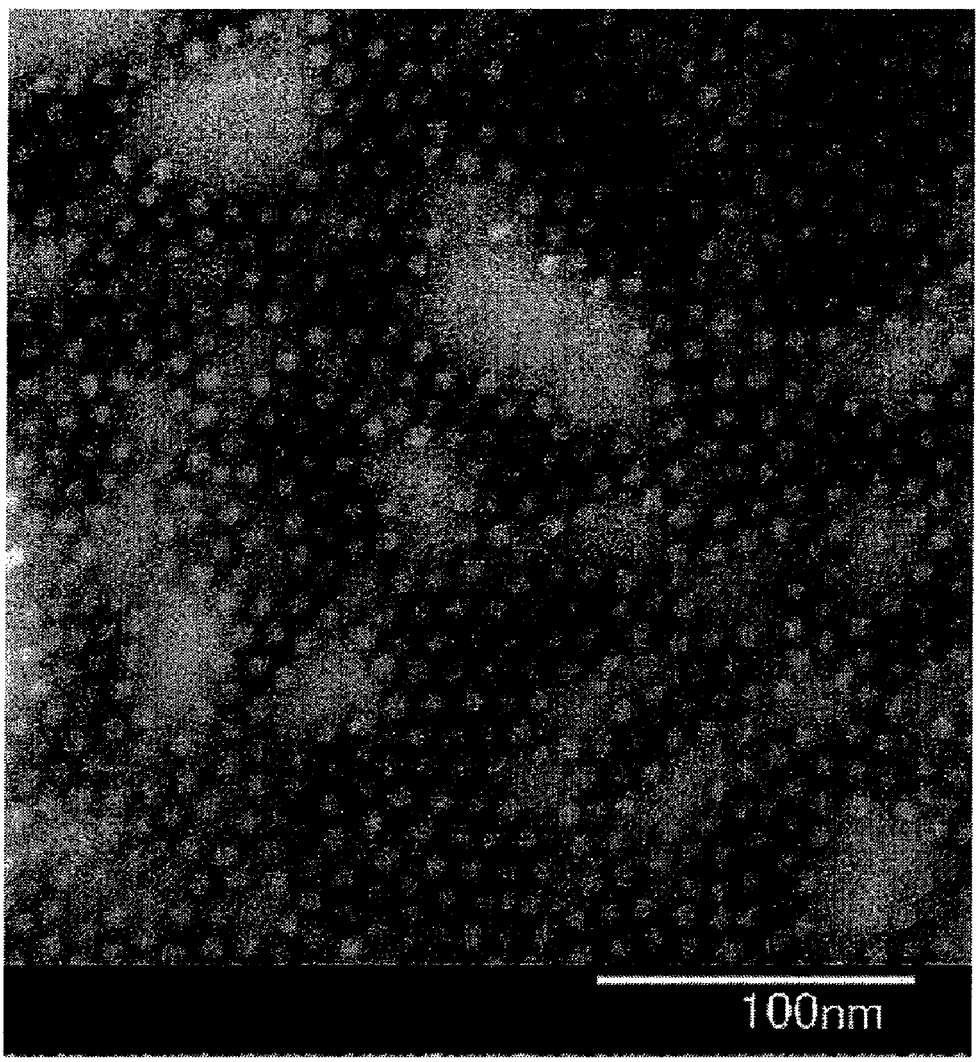
FIG. 11 shows a photograph illustrating the appearance of a two-dimensional array of ferritin obtained in Example 4.
Figure 12:
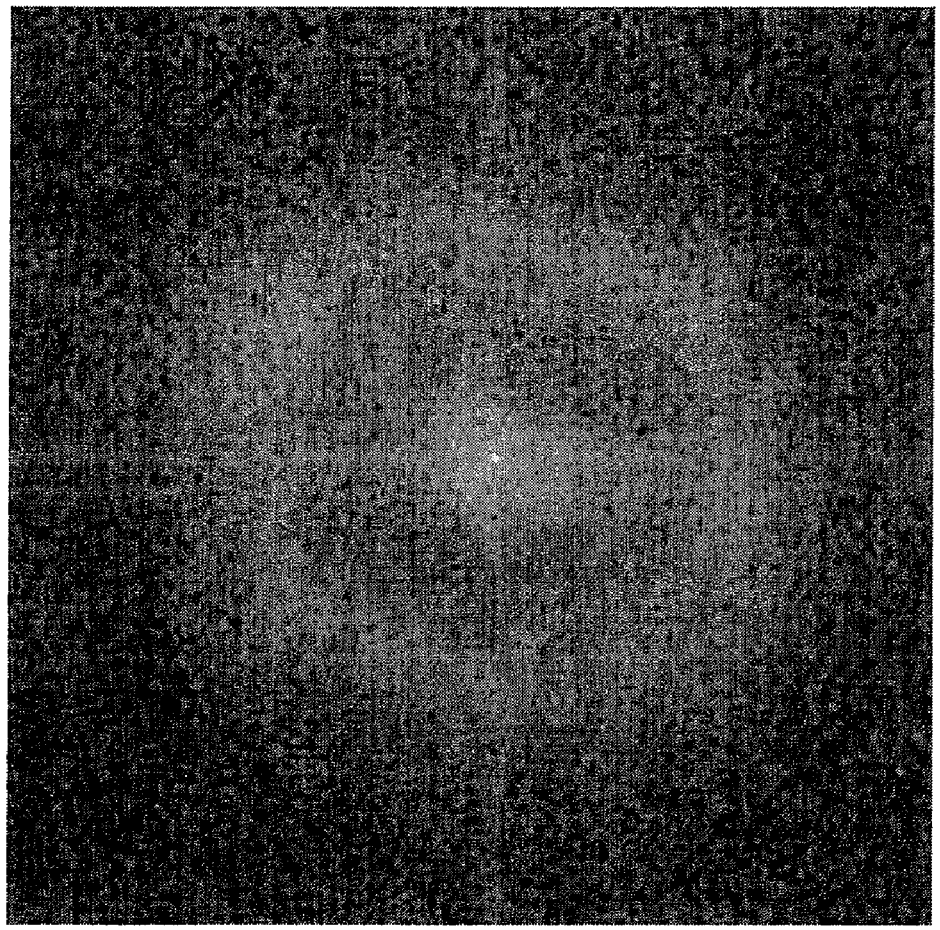
FIG. 12 shows a photograph of Fourier transformation image illustrating the appearance of a two-dimensional array of ferritin obtained in Example 4.

A photograph illustrating the appearance of a two-dimensional array of ferritin obtained using 0.5 mg/ml Y6F4DE-Fer0 (In) and 20 mM ammonium acetate is shown in FIG. 11, and a Fourier transformation image thereof is shown in FIG. 12.

As shown in FIG. 5 to FIG. 12, it was verified that the ferritin having an amino acid sequence set out in SEQ ID NO:

1 on its outer peripheral surface formed "favorable two-dimensional array" or "inferior two-dimensional array".

Comparative Example 1

Figure 13:
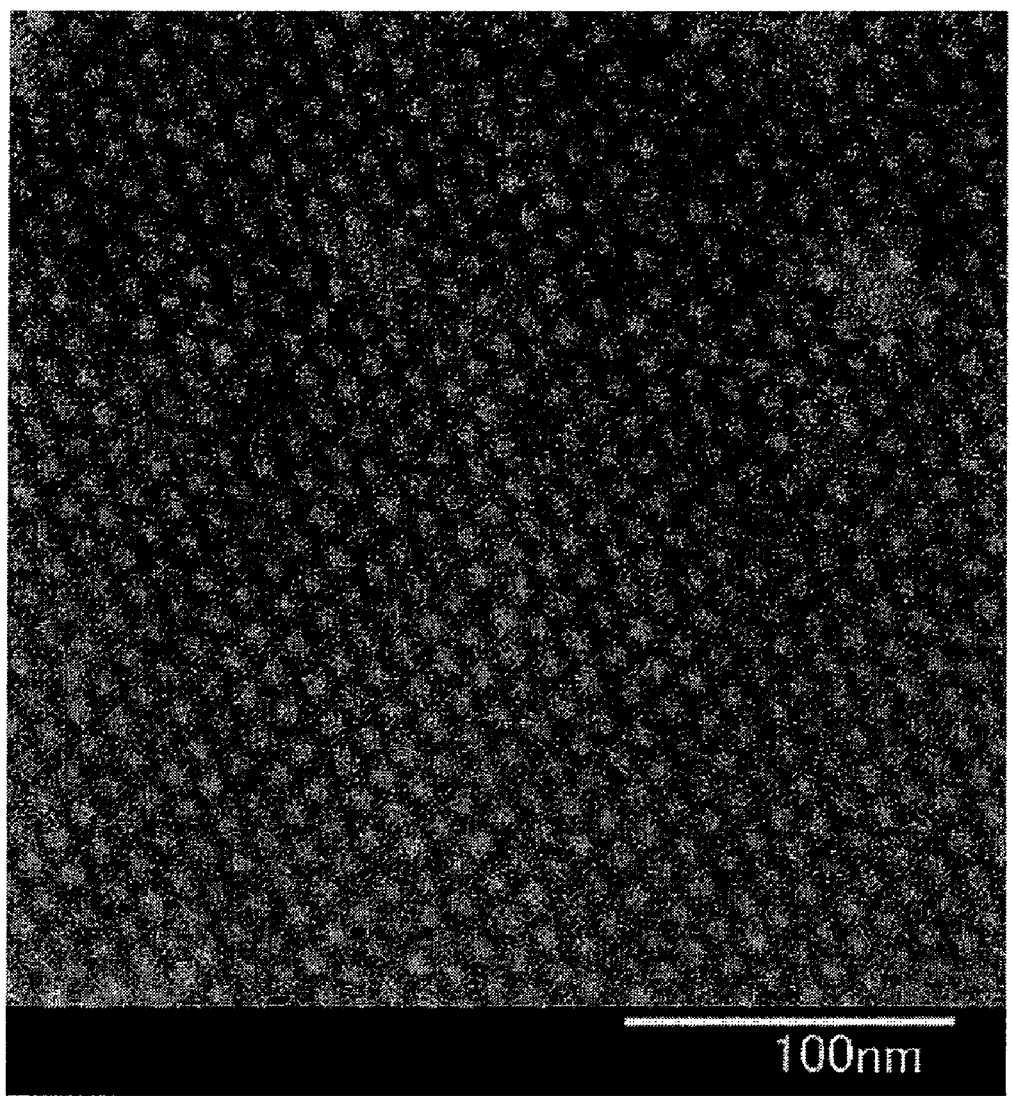
FIG. 13 shows a photograph illustrating the appearance of a two-dimensional array of ferritin obtained in Comparative Example 1.
Figure 14:
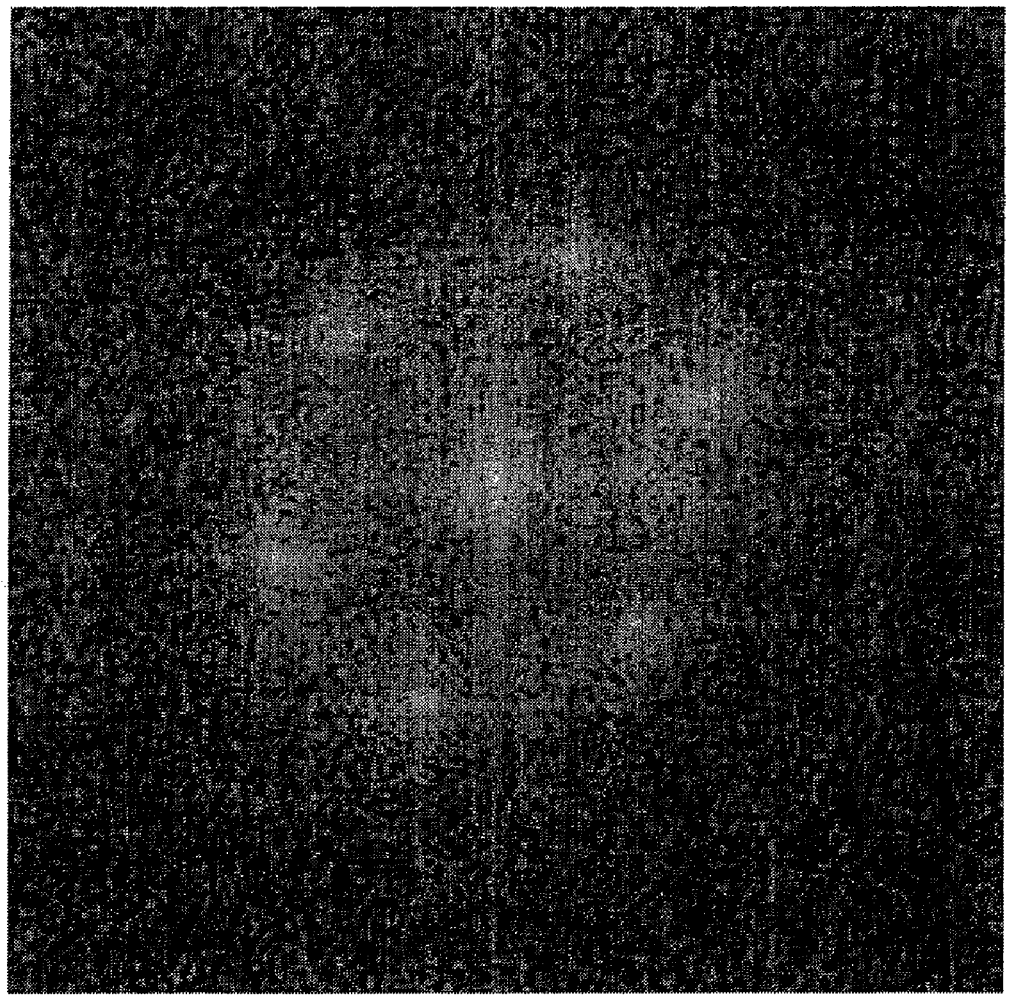
FIG. 14 shows a photograph of Fourier transformation image illustrating the appearance of a two-dimensional array of ferritin obtained in Comparative Example 1.

A photograph illustrating the appearance of a two-dimensional array of ferritin obtained using 0.5 mg/ml N1-LF (In) and 12.5 mM PIPES-NaOH (pH 7.0) is shown in FIG. 13, and a Fourier transformation image thereof is shown in FIG. 14.

Comparative Example 2

Figure 15:
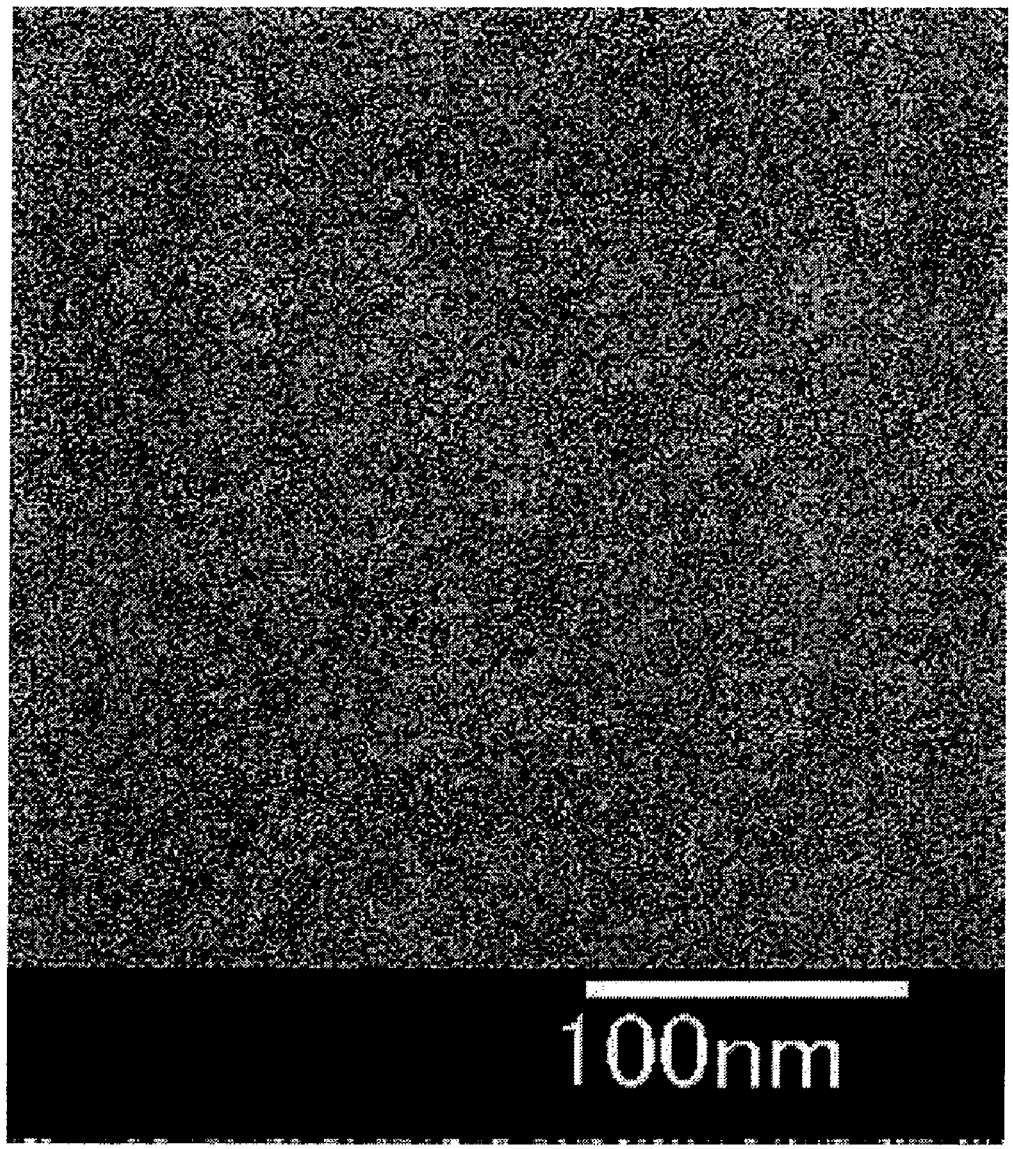
FIG. 15 shows a photograph illustrating the appearance of a two-dimensional array of ferritin obtained in Comparative Example 2.
Figure 16:
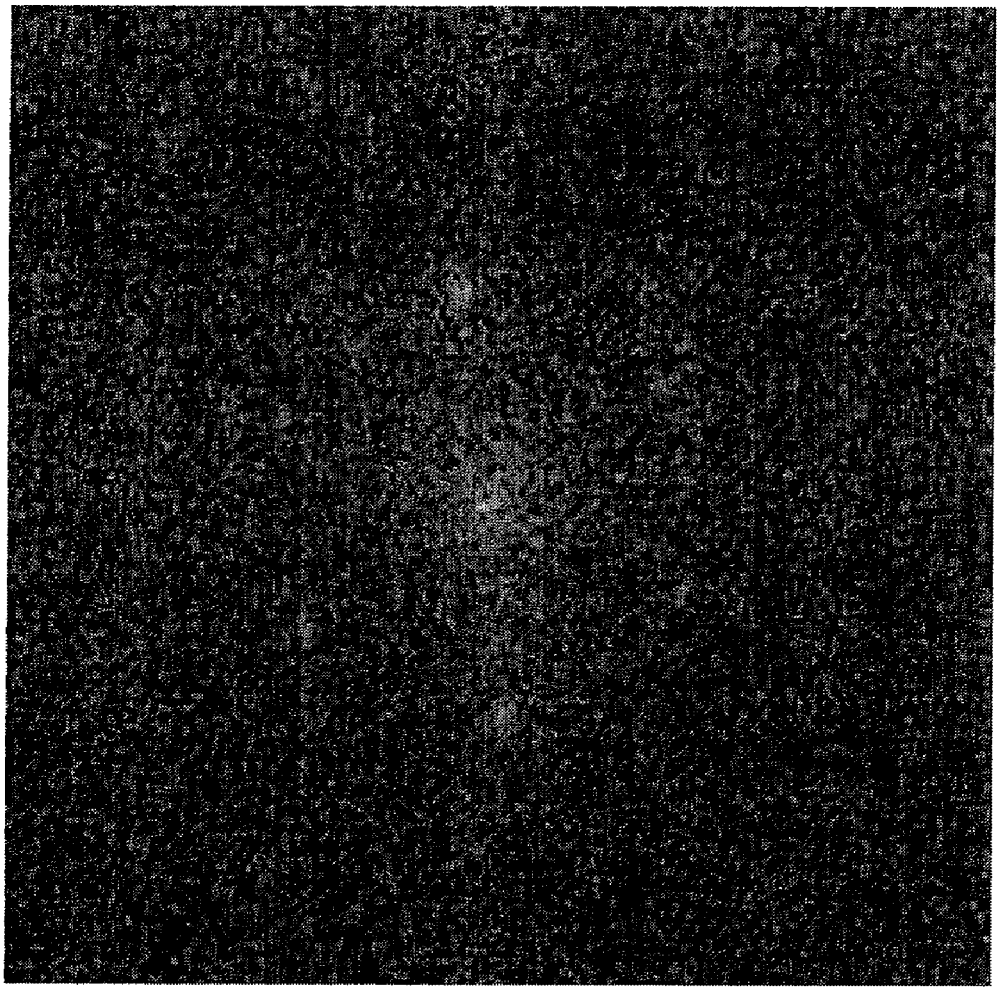
FIG. 16 shows a photograph of Fourier transformation image illustrating the appearance of a two-dimensional array of ferritin obtained in Comparative Example 2.

A photograph illustrating the appearance of a two-dimensional array of ferritin obtained using 0.5 mg/ml N1-LF (In) and 12.5 mM PIPES-Tris (pH 7.0) is shown in FIG. 15, and a Fourier transformation image thereof is shown in FIG. 16.

Comparative Example 3

Figure 17:
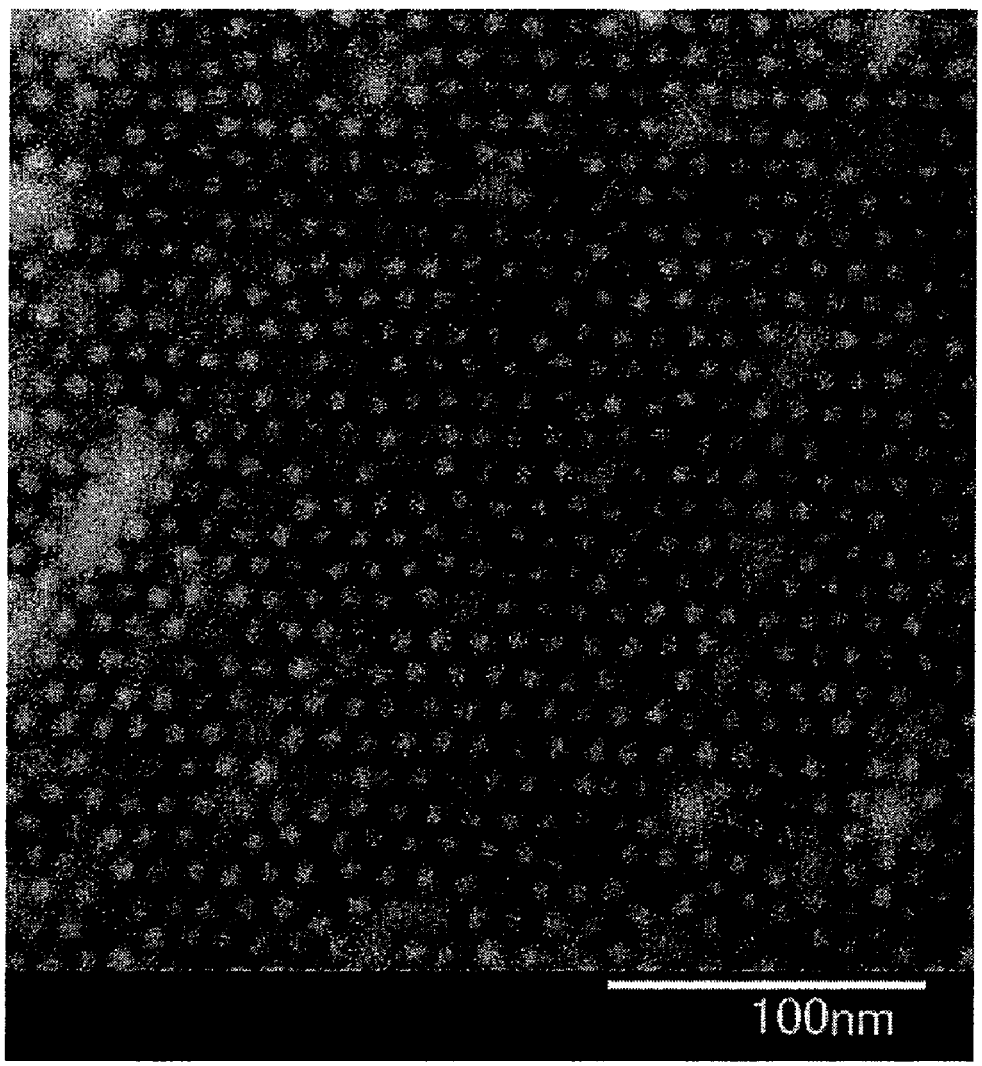
FIG. 17 shows a photograph illustrating the appearance of a two-dimensional array of ferritin obtained in Comparative Example 3.
Figure 18:
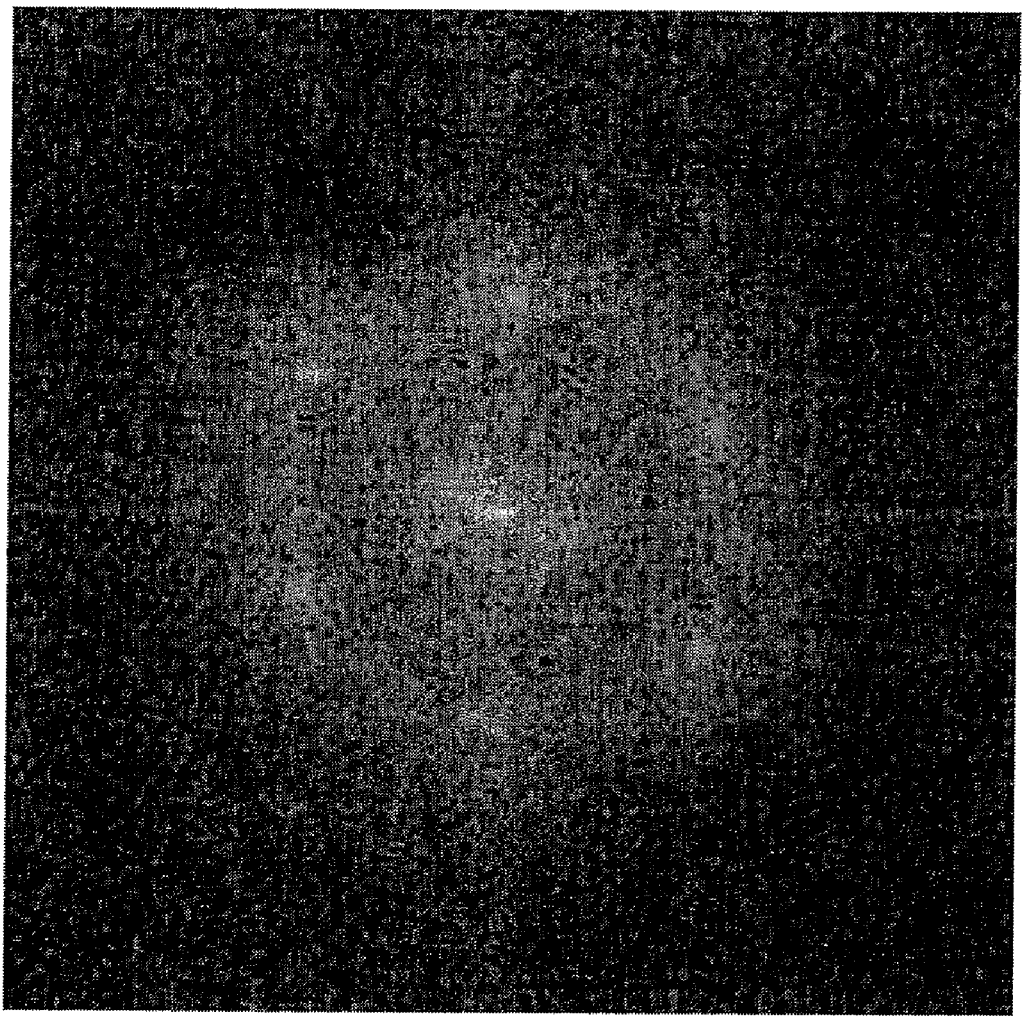
FIG. 18 shows a photograph of Fourier transformation image illustrating the appearance of a two-dimensional array of ferritin obtained in Comparative Example 3.

A photograph illustrating the appearance of a two-dimensional array of ferritin obtained using 0.5 mg/ml N1-LF (In) and 13 mM ammonium sulfate is shown in FIG. 17, and a Fourier transformation image thereof is shown in FIG. 18.

Comparative Example 4

Figure 19:
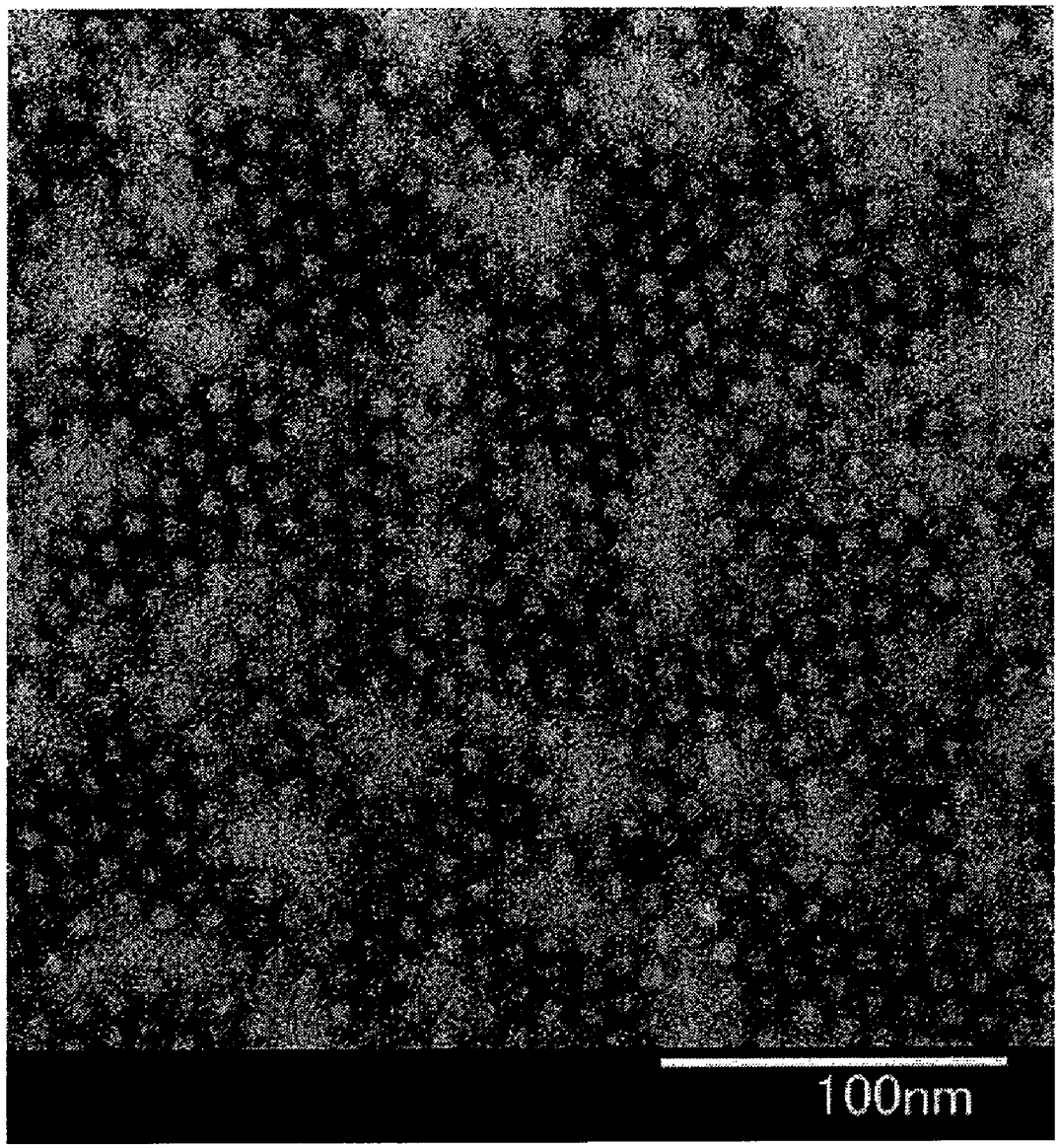
FIG. 19 shows a photograph illustrating the appearance of a two-dimensional array of ferritin obtained in Comparative Example 4.
Figure 20:
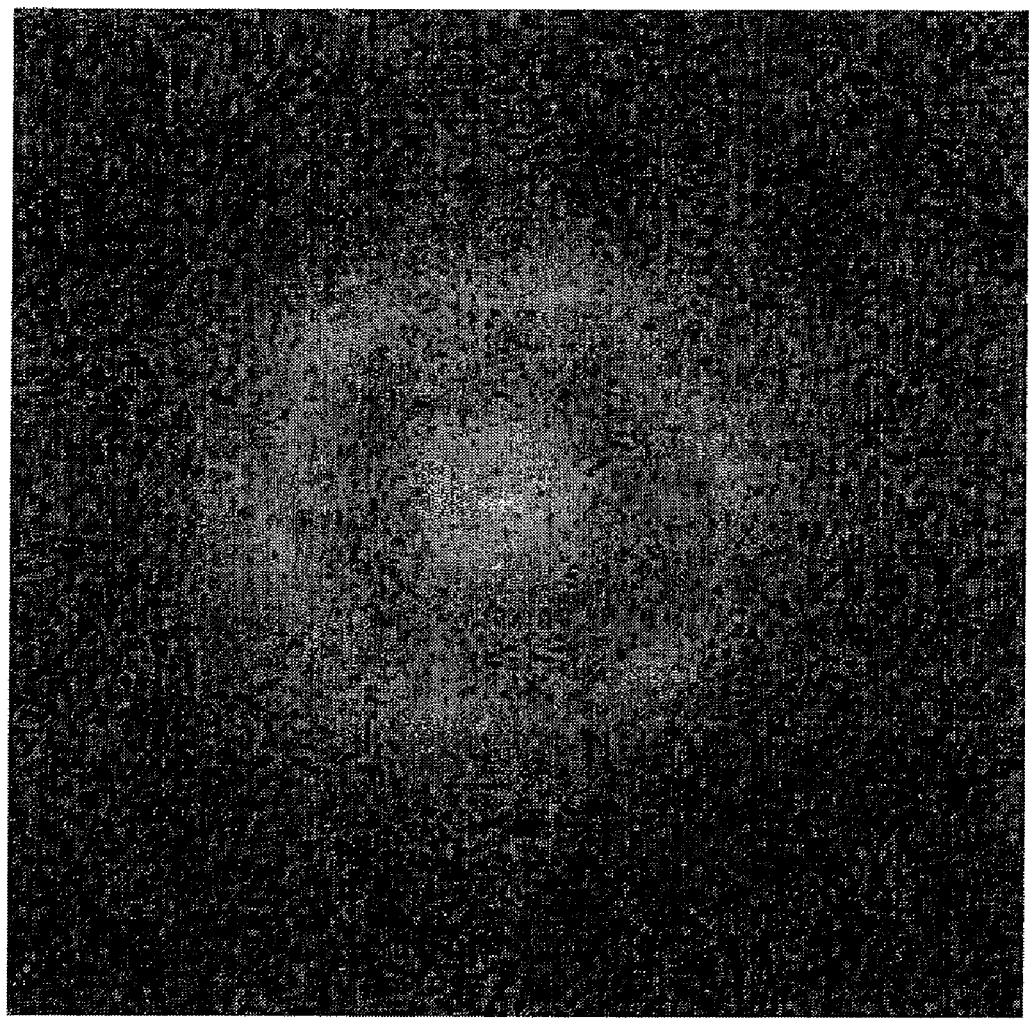
FIG. 20 shows a photograph of Fourier transformation image illustrating the appearance of a two-dimensional array of ferritin obtained in Comparative Example 4.

A photograph illustrating the appearance of a two-dimensional array of ferritin obtained using 0.5 mg/ml N1-LF (In) and 20 mM ammonium acetate is shown in FIG. 19, and a Fourier transformation image thereof is shown in FIG. 20.

It could be verified that the ferritin having an amino acid sequence set out in SEQ ID NO: 1 on its outer peripheral surface formed "favorable two-dimensional array" or "inferior two-dimensional array", although when compared with N1-LF in conventional examples shown in FIG. 13 to FIG. 20, they were equal to or equal to with limitations (for example, domain size of the two-dimensional array being small) to the same.

Comparative Example 5

Figure 21:
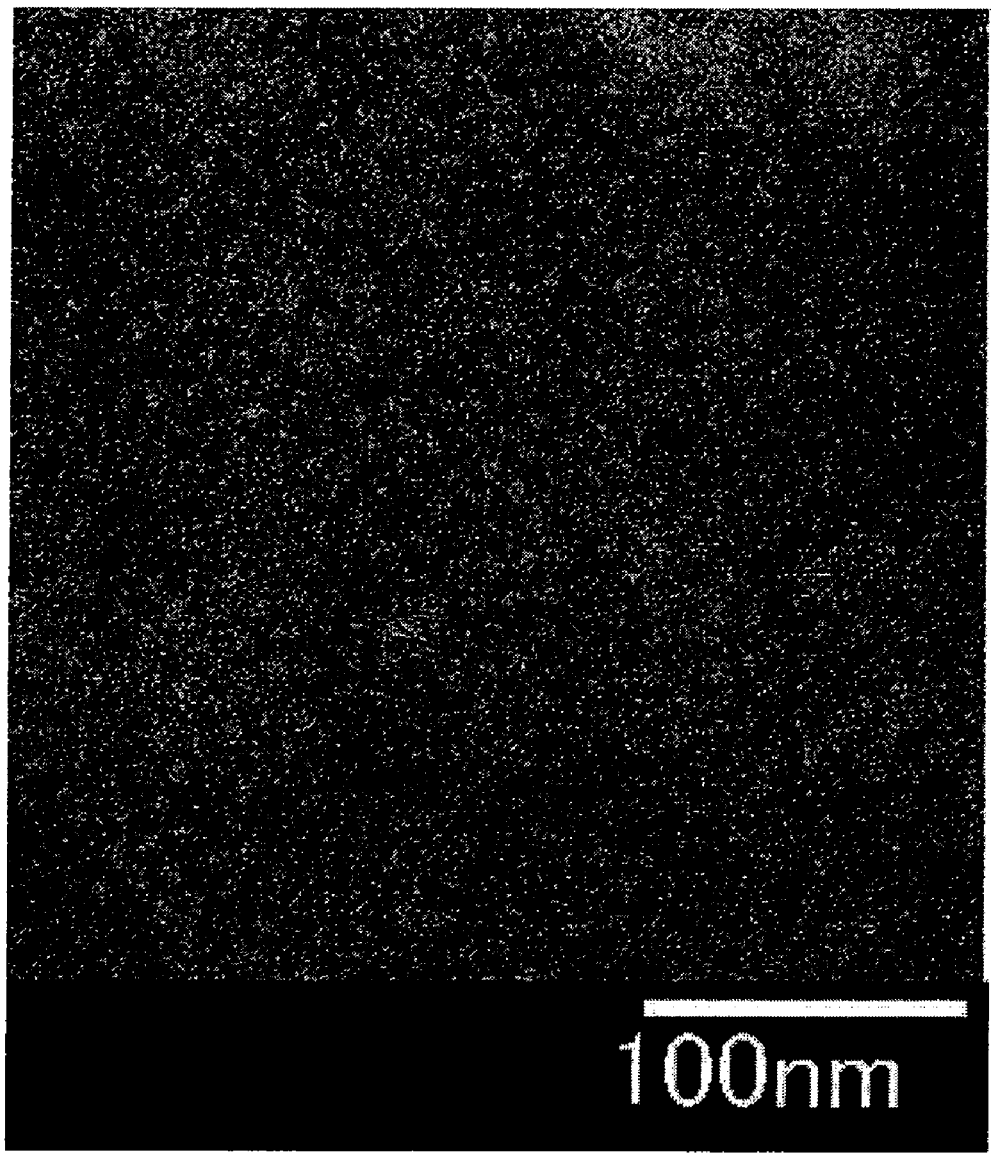
FIG. 21 shows a photograph illustrating the appearance of a two-dimensional array of ferritin obtained in Comparative Example 5.
Figure 22:
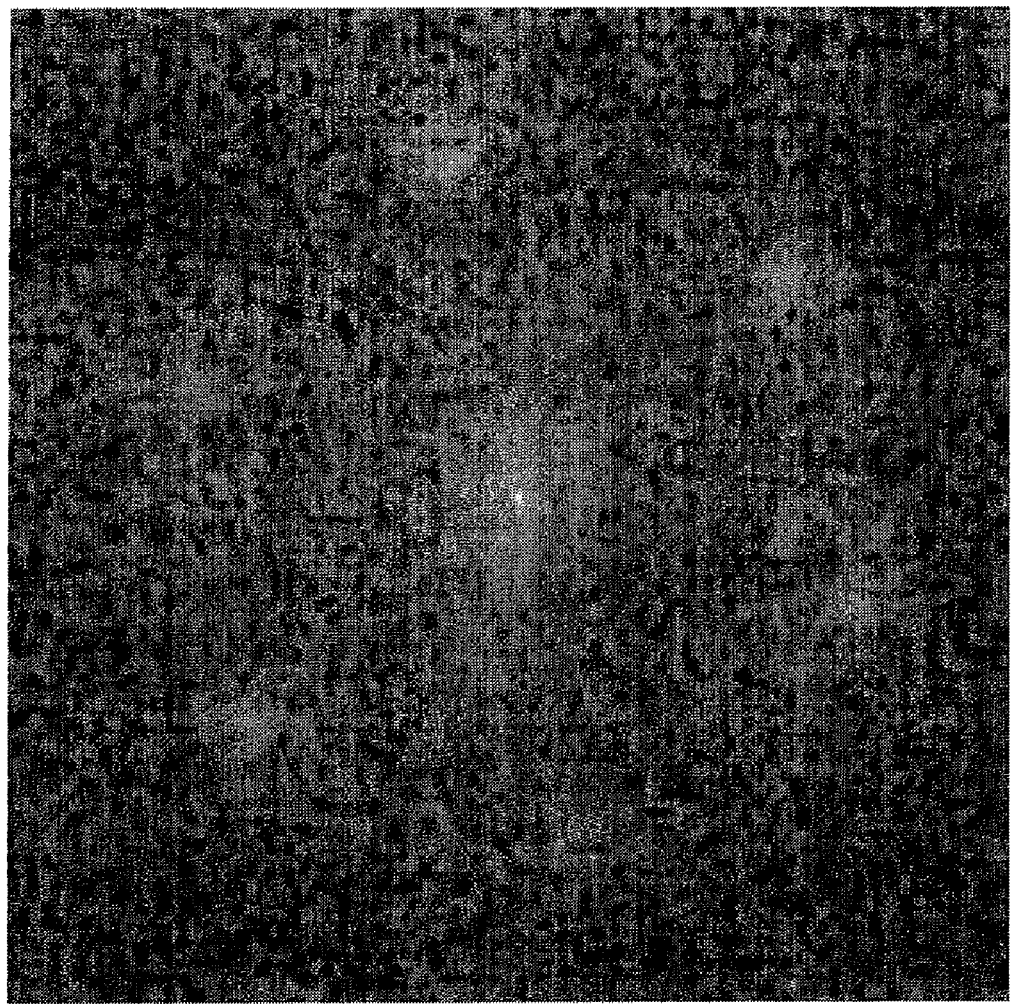
FIG. 22 shows a photograph of Fourier transformation image illustrating the appearance of a two-dimensional array of ferritin obtained in Comparative Example 5.

A photograph illustrating the appearance of a two-dimensional array of ferritin obtained using 0.5 mg/ml D2N-Fer0 (In) and 12.5 mM PIPES-NaOH (pH 7.0) is shown in FIG. 21, and a Fourier transformation image thereof is shown in FIG. 22.

Comparative Example 6

Figure 23:
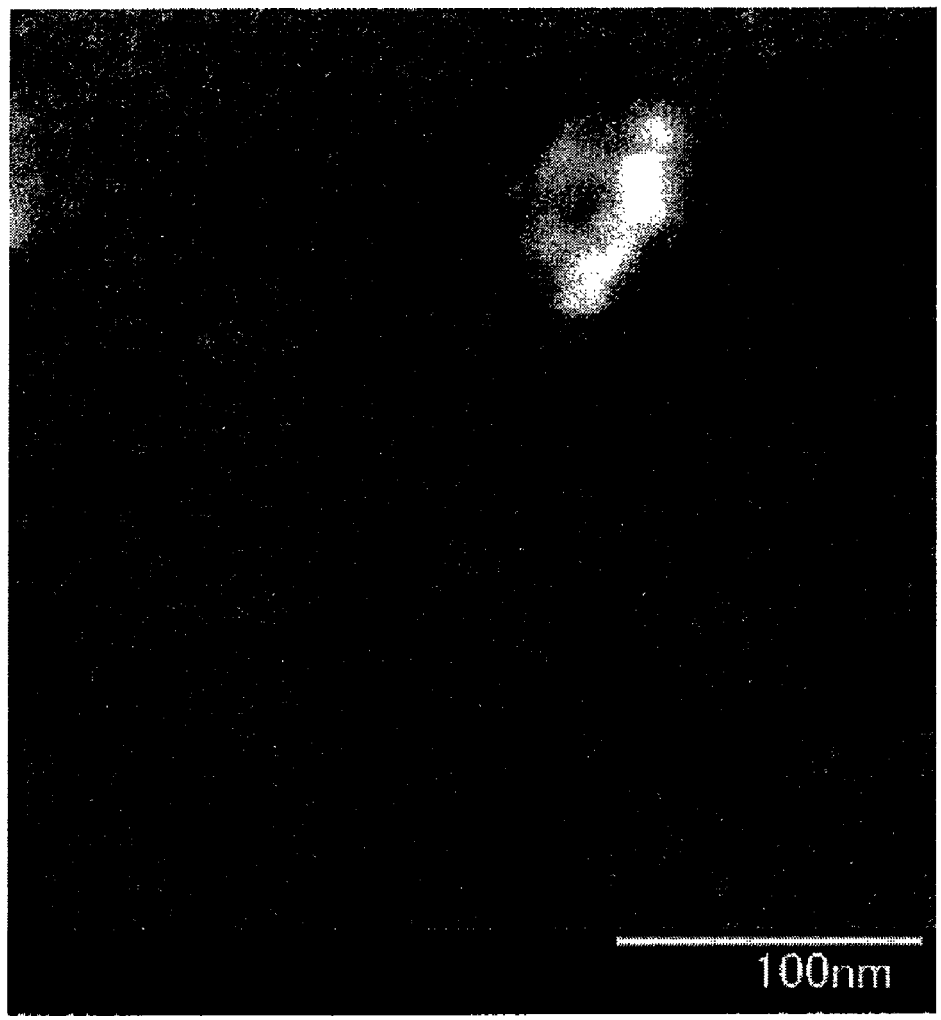
FIG. 23 shows a photograph illustrating the appearance of a two-dimensional array of ferritin obtained in Comparative Example 6.
Figure 24:
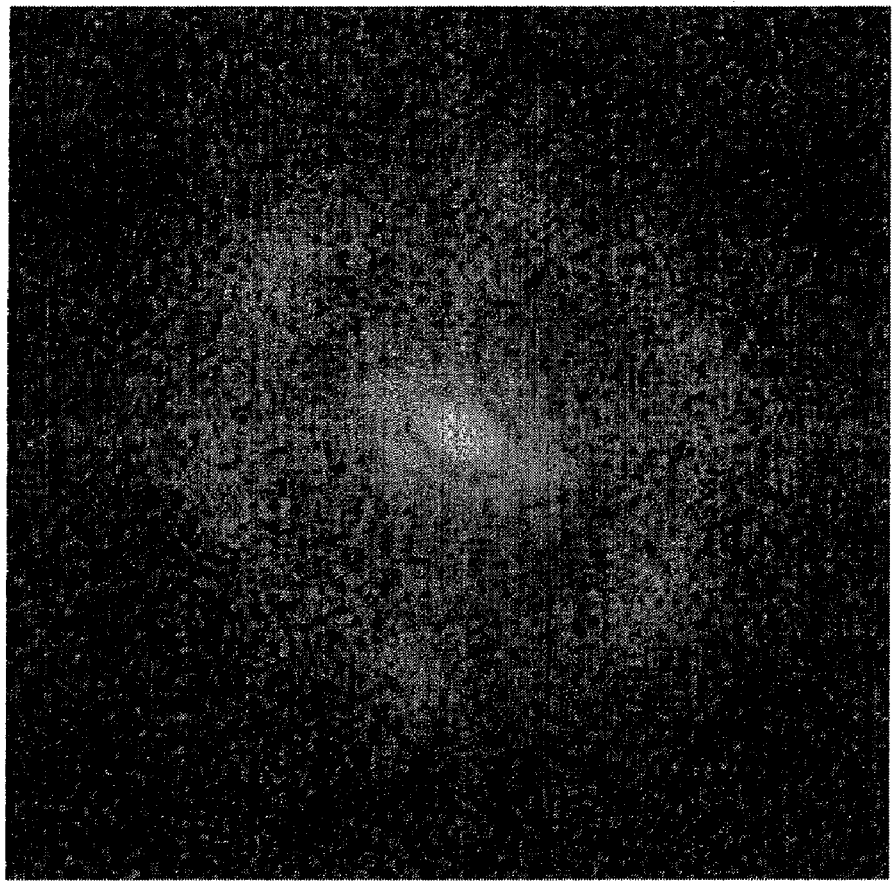
FIG. 24 shows a photograph of Fourier transformation image illustrating the appearance of a two-dimensional array of ferritin obtained in Comparative Example 6.

A photograph illustrating the appearance of a two-dimensional array of ferritin obtained using 0.5 mg/ml D2N-Fer0 (In) and 13 mM ammonium sulfate is shown in FIG. 23, and a Fourier transformation image thereof is shown in FIG. 24.

Comparative Example 7

Figure 25:
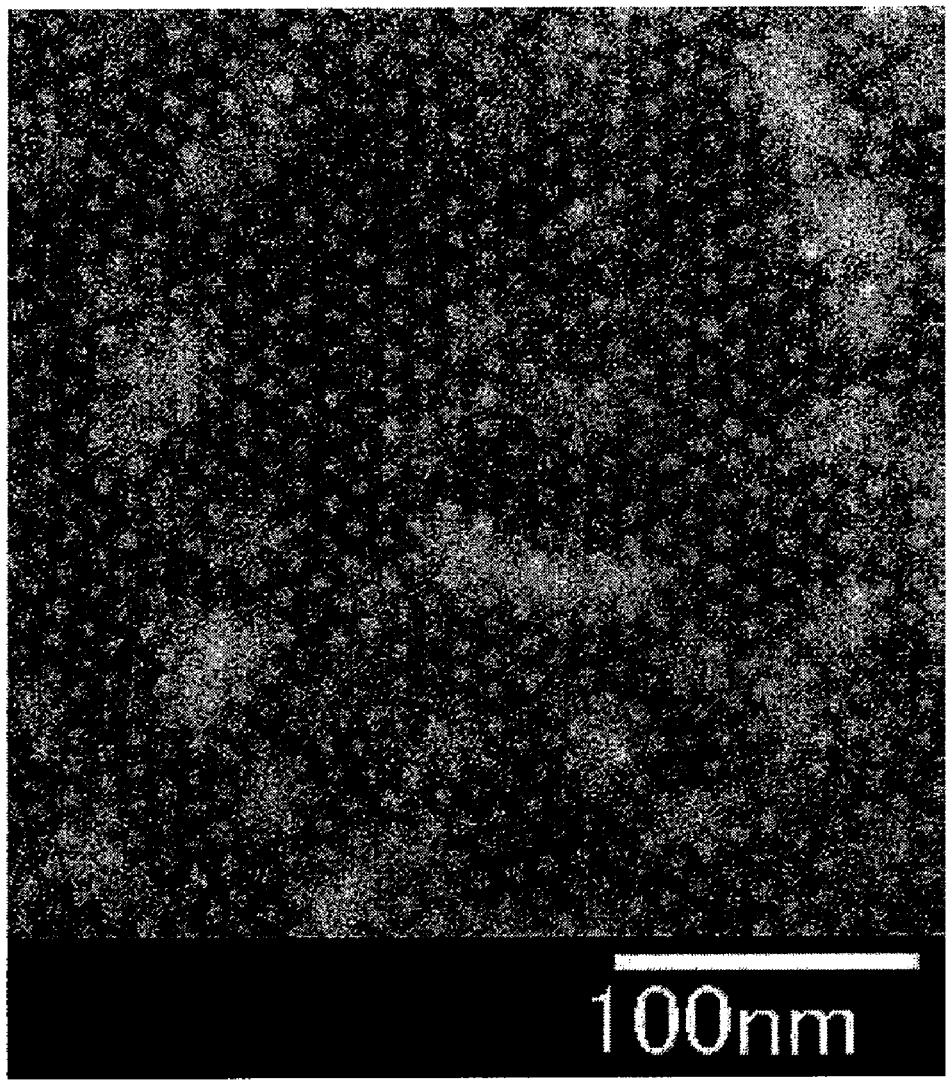
FIG. 25 shows a photograph illustrating the appearance of a two-dimensional array of ferritin obtained in Comparative Example 7.
Figure 26:
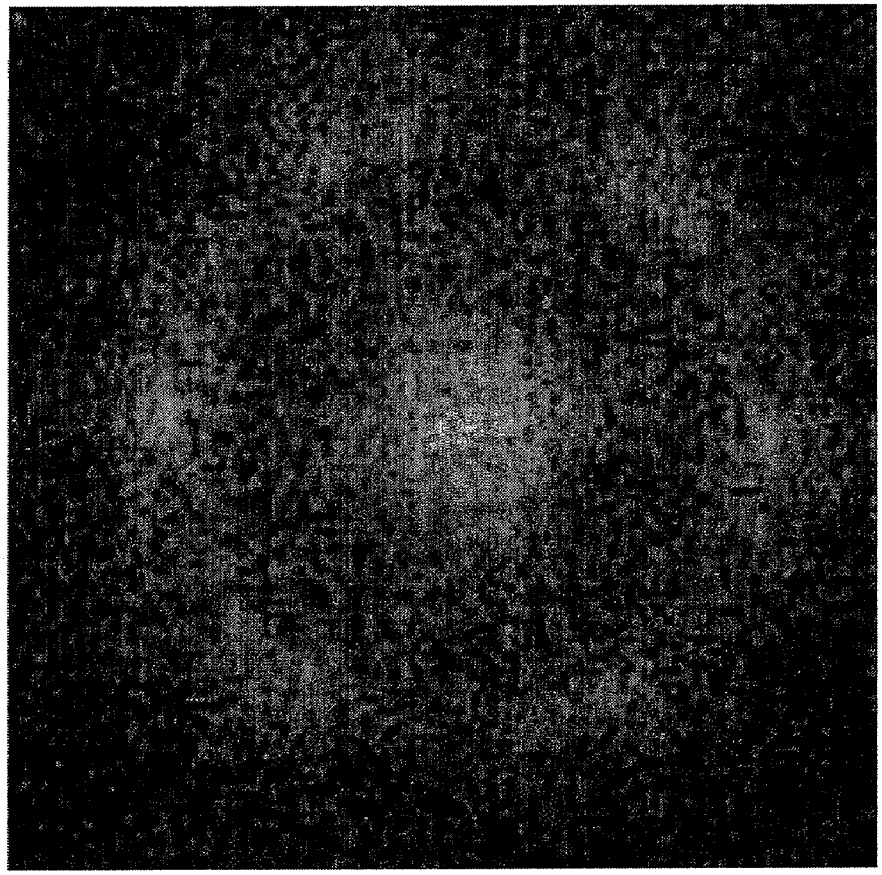
FIG. 26 shows a photograph of Fourier transformation image illustrating the appearance of a two-dimensional array of ferritin obtained in Comparative Example 7.

A photograph illustrating the appearance of a two-dimensional array of ferritin obtained using 0.5 mg/ml D2N-Fer0 (In) and 20 mM ammonium acetate is shown in FIG. 25, and a Fourier transformation image thereof is shown in FIG. 26.

Comparative Example 8

Figure 27:
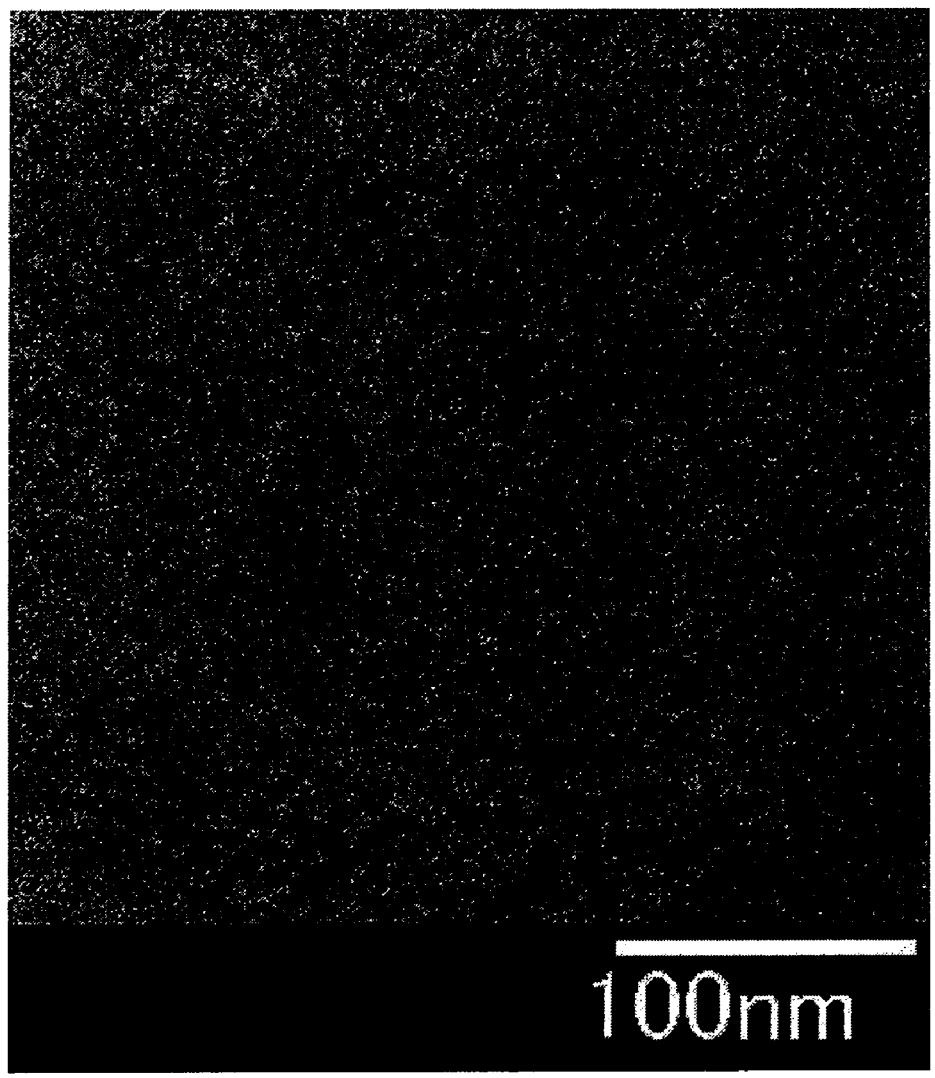
FIG. 27 shows a photograph illustrating the appearance of a two-dimensional array of ferritin obtained in Comparative Example 8.
Figure 28:
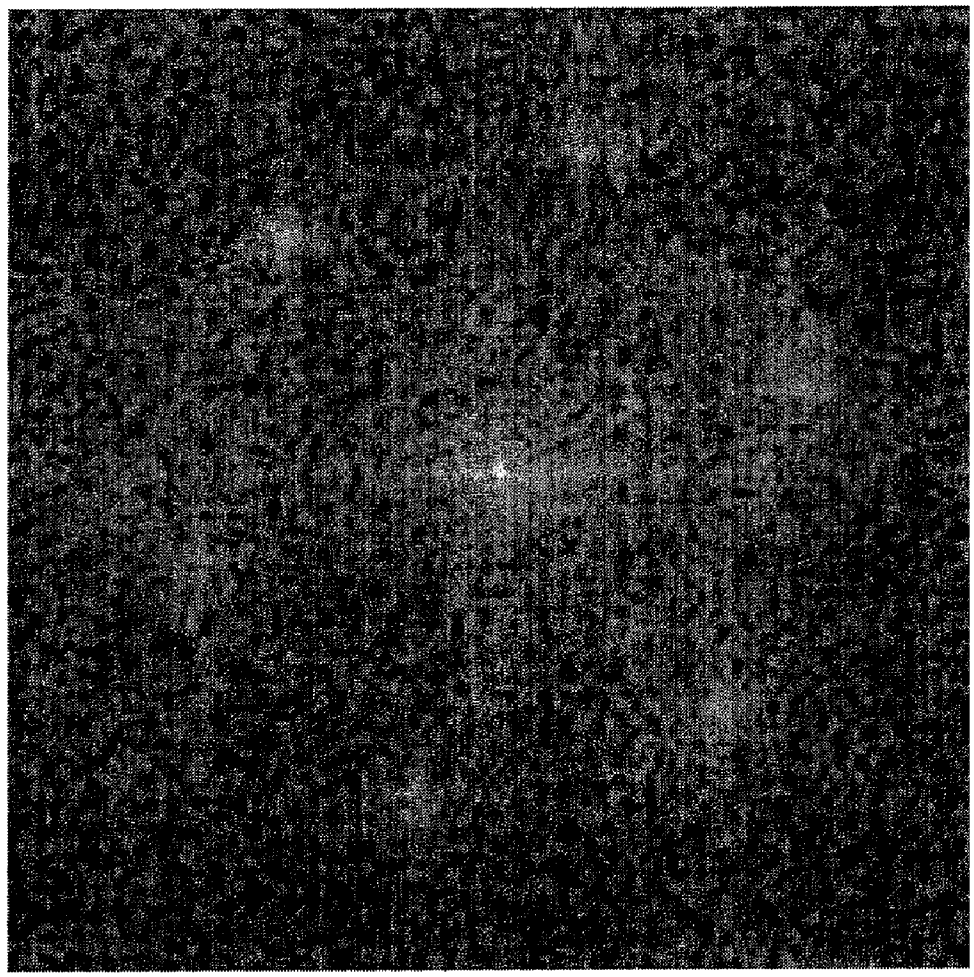
FIG. 28 shows a photograph of Fourier transformation image illustrating the appearance of a two-dimensional array of ferritin obtained in Comparative Example 8.

A photograph illustrating the appearance of a two-dimensional array of ferritin obtained using 0.5 mg/ml E10Q-Fer0 (In) and 12.5 mM PIPES-NaOH (pH 7.0) is shown in FIG. 27, and a Fourier transformation image thereof is shown in FIG. 28.

Comparative Example 9

Figure 29:
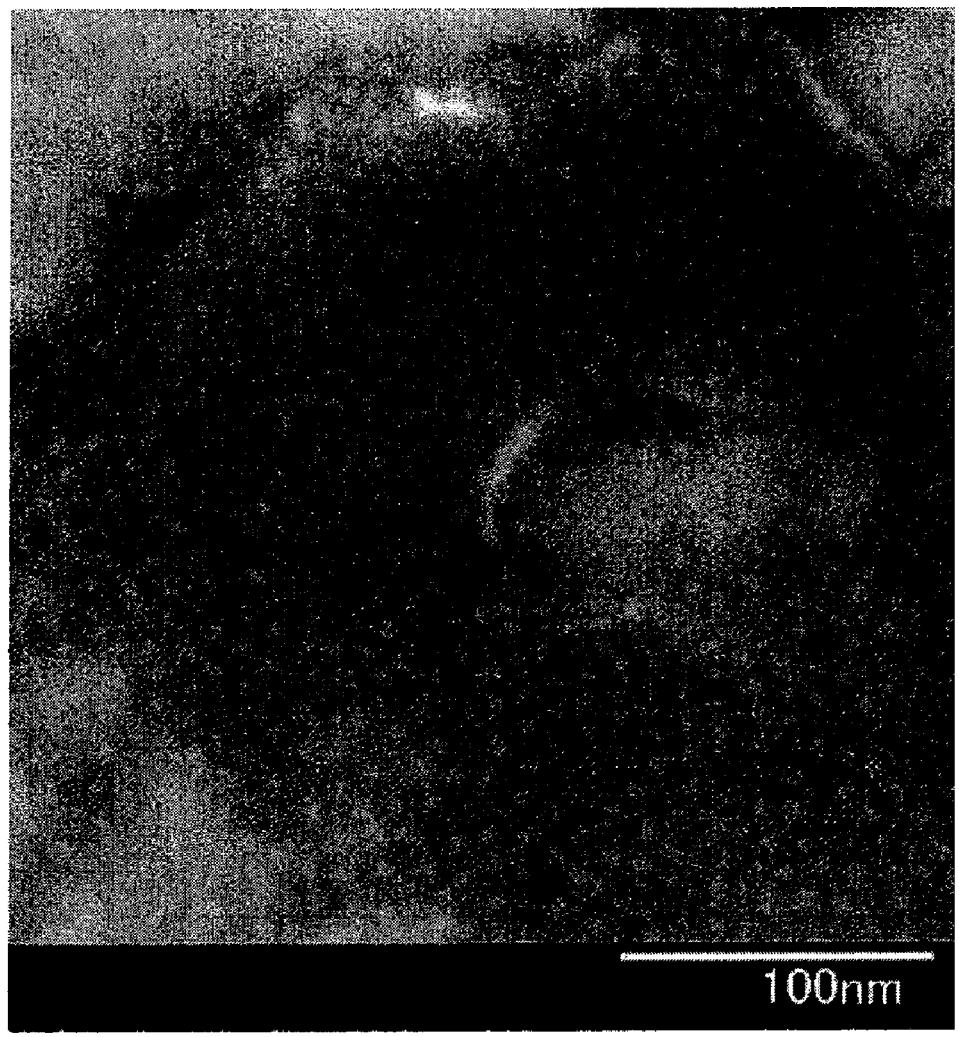
FIG. 29 shows a photograph illustrating the appearance of a two-dimensional array of ferritin obtained in Comparative Example 9.
Figure 30:
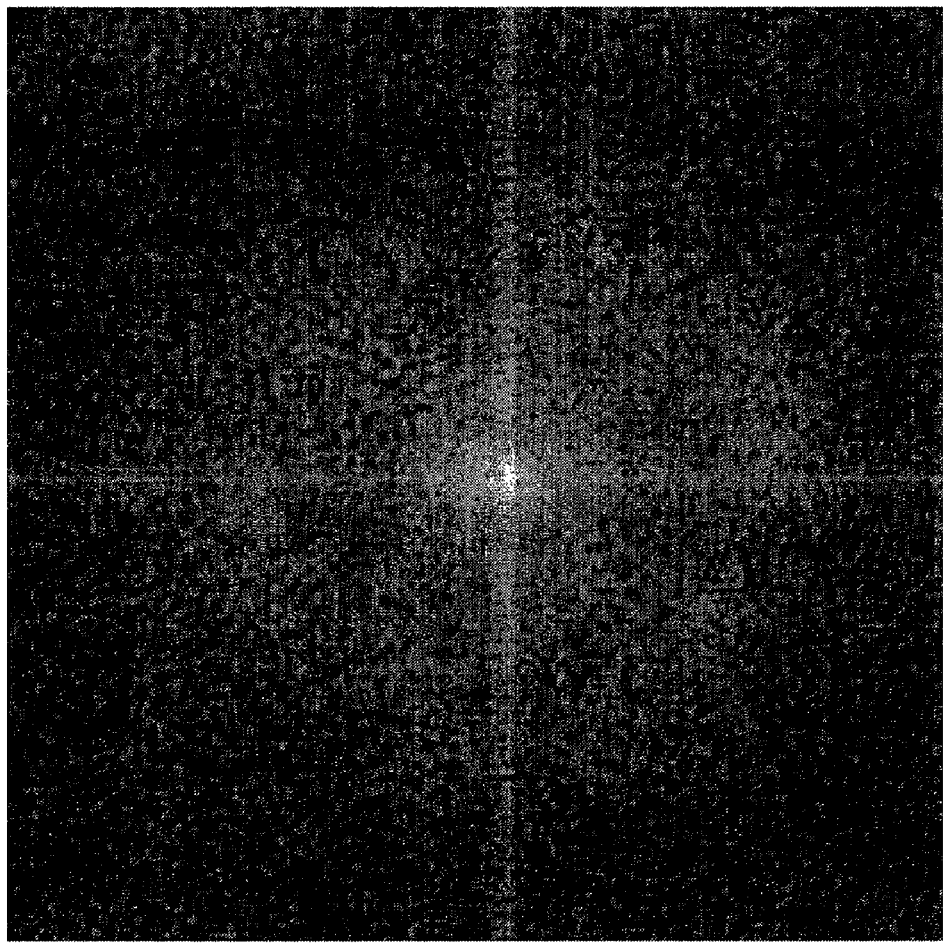
FIG. 30 shows a photograph of Fourier transformation image illustrating the appearance of a two-dimensional array of ferritin obtained in Comparative Example 9.

A photograph illustrating the appearance of a two-dimensional array of ferritin obtained using 0.5 mg/ml E10Q-Fer0 (In) and 13 mM ammonium sulfate is shown in FIG. 29, and a Fourier transformation image thereof is shown in FIG. 30.

Comparative Example 10

Figure 31:
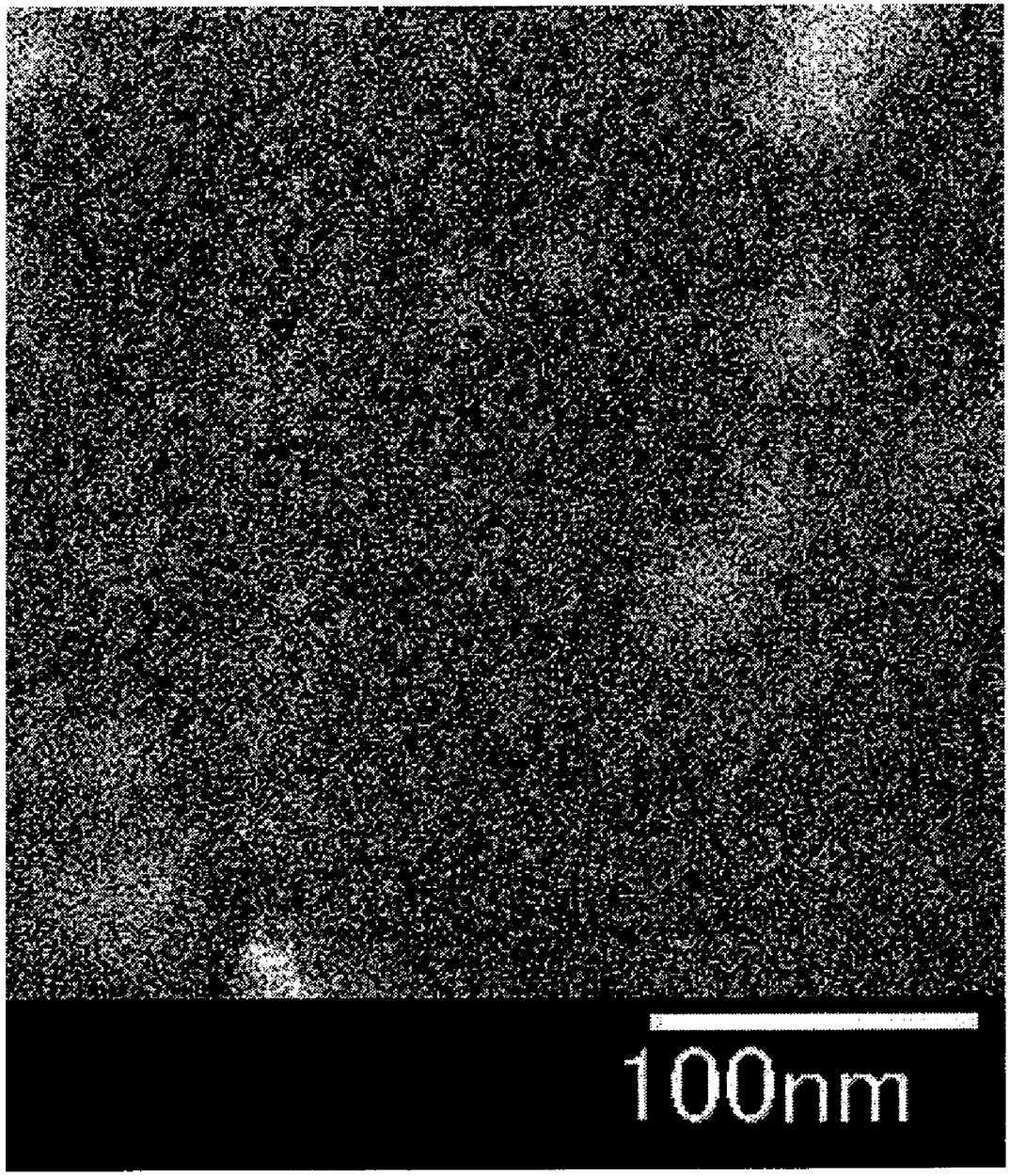
FIG. 31 shows a photograph illustrating the appearance of a two-dimensional array of ferritin obtained in Comparative Example 10.
Figure 32:
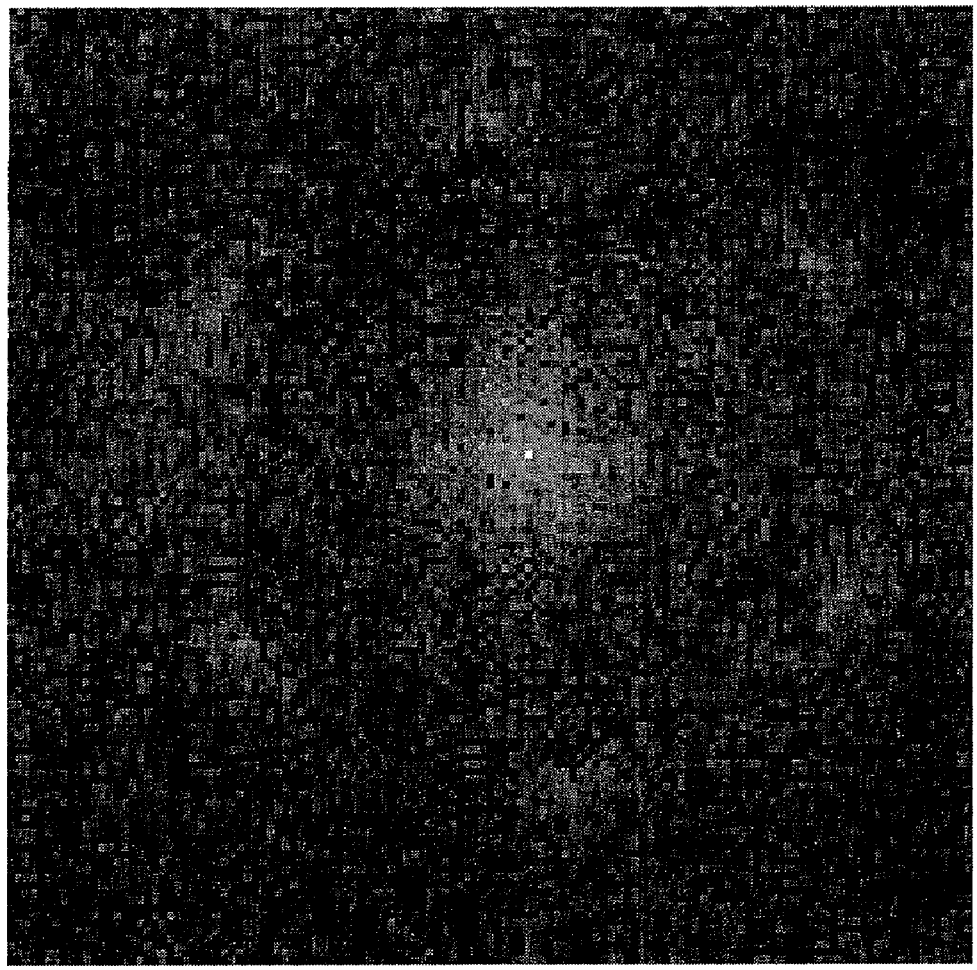
FIG. 32 shows a photograph of Fourier transformation image illustrating the appearance of a two-dimensional array of ferritin obtained in Comparative Example 10.

A photograph illustrating the appearance of a two-dimensional array of ferritin obtained using 0.5 mg/ml E10Q-Fer0 (In) and 20 mM ammonium acetate is shown in FIG. 31, and a Fourier transformation image thereof is shown in FIG. 32.

Comparative Example 11

Figure 33:
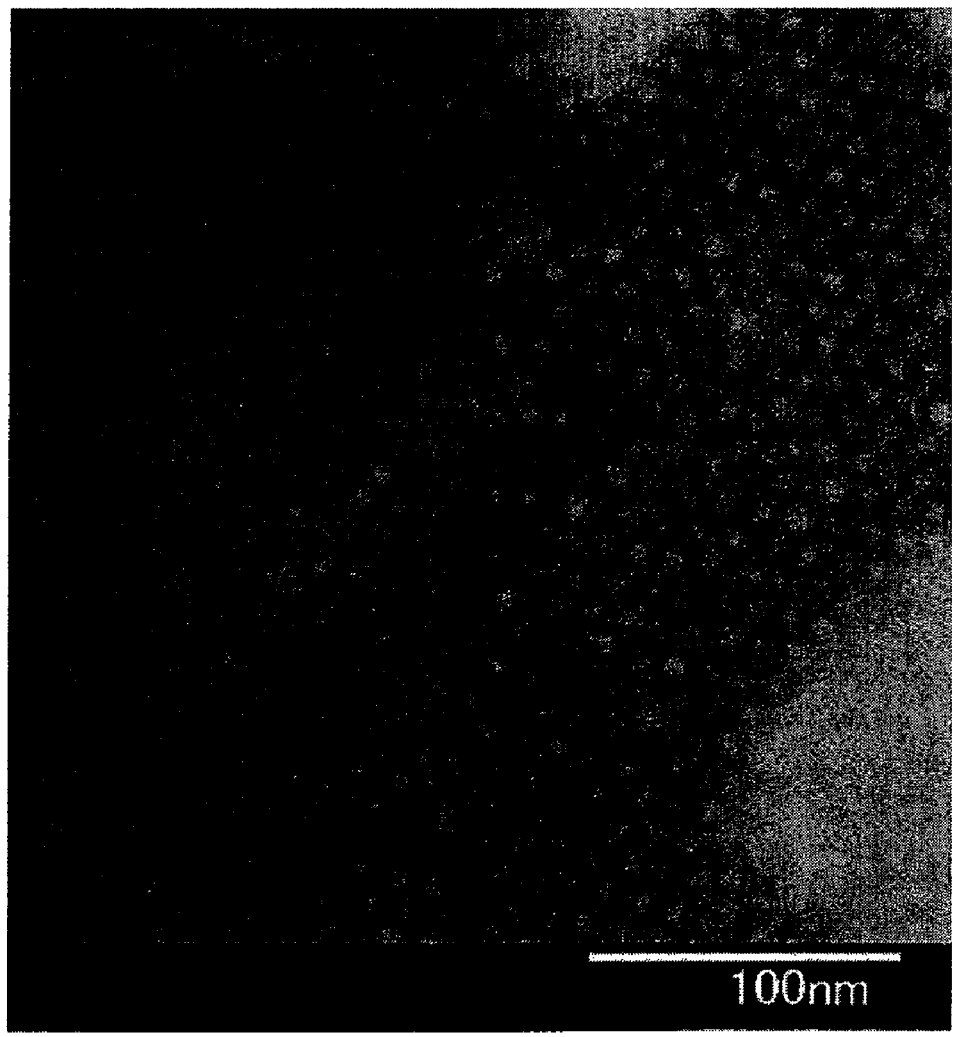
FIG. 33 shows a photograph illustrating the appearance of a two-dimensional array of ferritin obtained in Comparative Example 11.
Figure 34:
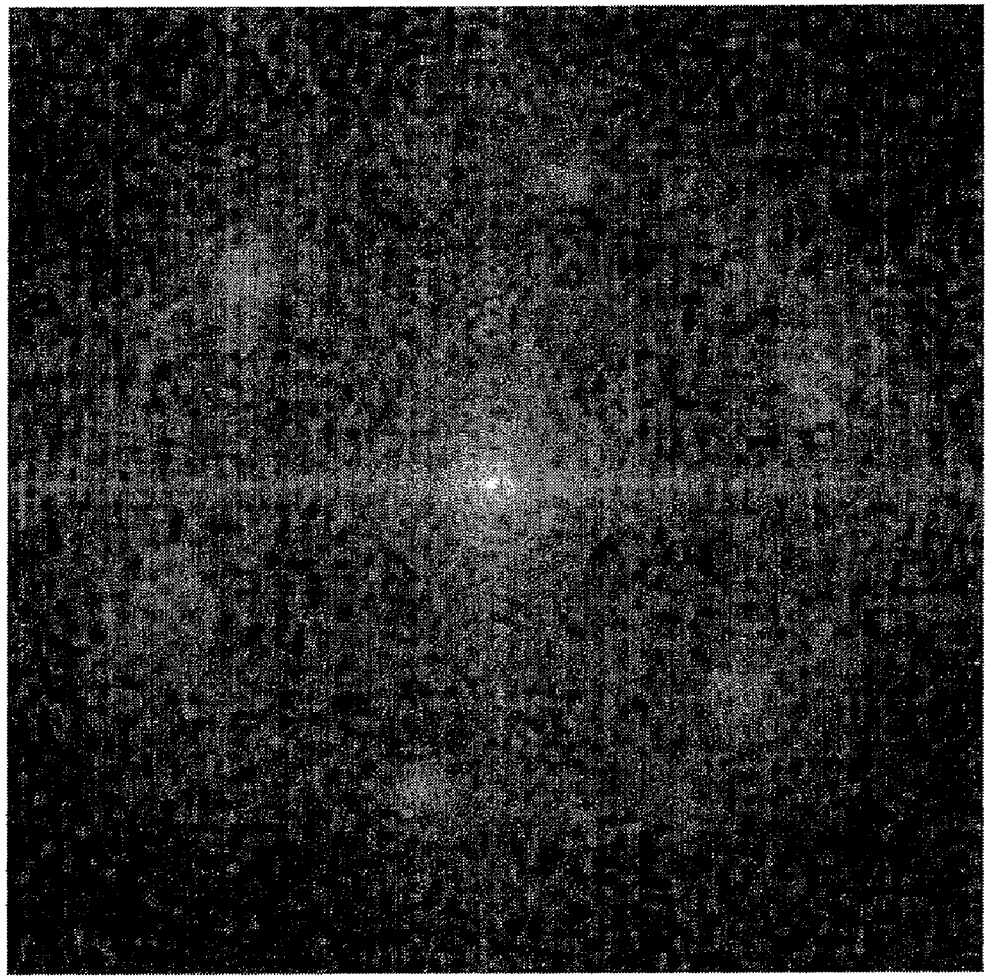
FIG. 34 shows a photograph of Fourier transformation image illustrating the appearance of a two-dimensional array of ferritin obtained in Comparative Example 11.

A photograph illustrating the appearance of a two-dimensional array of ferritin obtained using suspended E10S-Fer0 (In) and 2 mM Tris-HCl buffer (pH8.0), and a thermally oxidized silicon substrate is shown in FIG. 33, and a Fourier transformation image thereof is shown in FIG. 34.

Comparative Example 12

Figure 35:
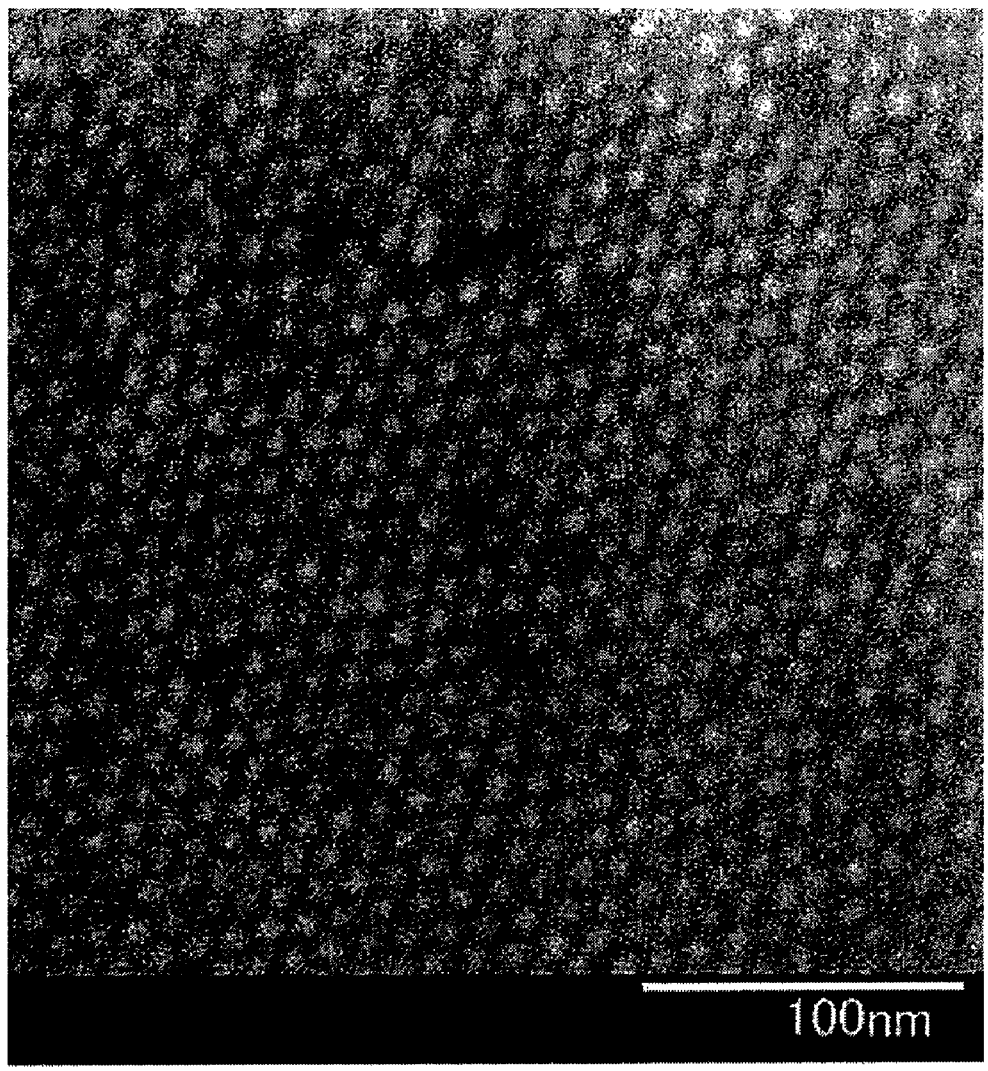
FIG. 35 shows a photograph illustrating the appearance of a two-dimensional array of ferritin obtained in Comparative Example 12.
Figure 36:
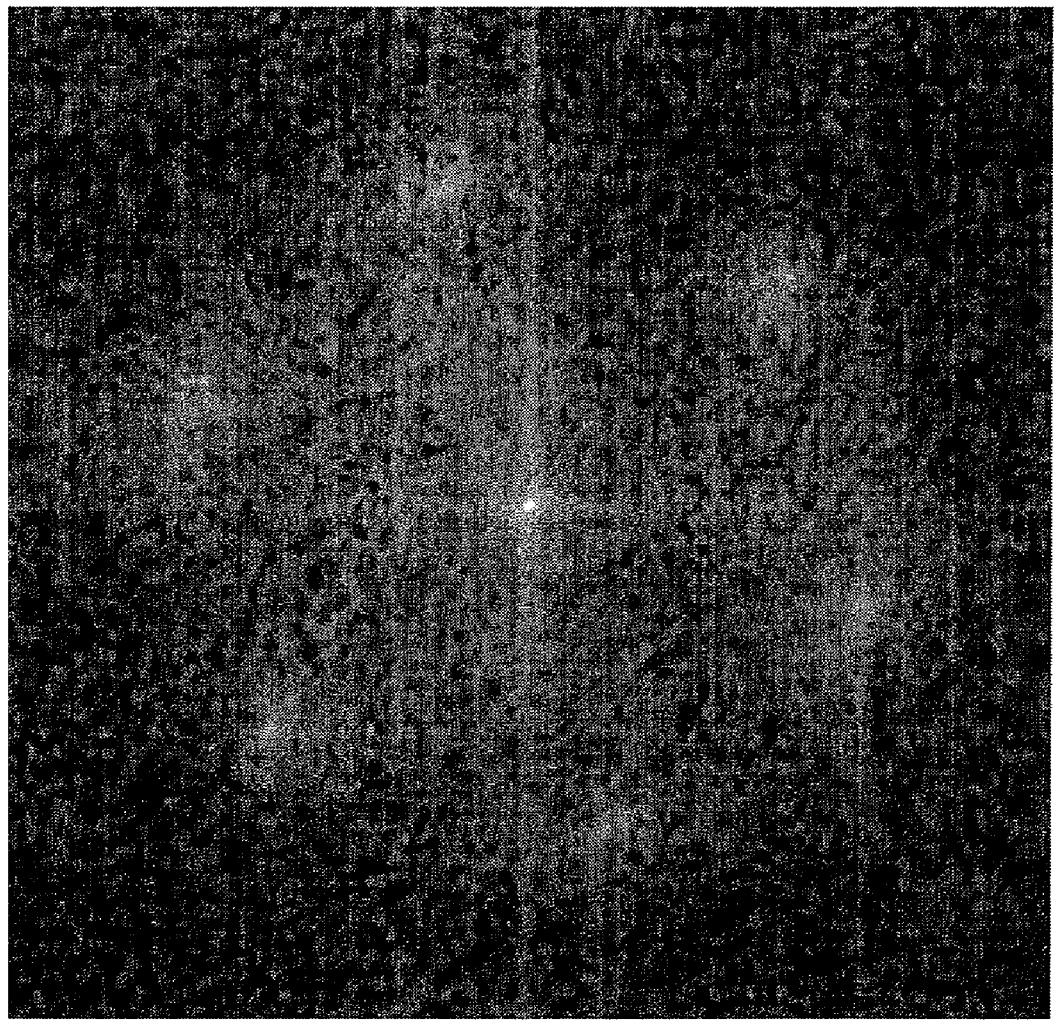
FIG. 36 shows a photograph of Fourier transformation image illustrating the appearance of a two-dimensional array of ferritin obtained in Comparative Example 12.

A photograph illustrating the appearance of a two-dimensional array of ferritin obtained using 0.5 mg/ml P7S-Fer0 (In) and 12.5 mM PIPES-NaOH (pH 7.0) is shown in FIG. 35, and a Fourier transformation image thereof is shown in FIG. 36.

Comparative Example 13

Figure 37:
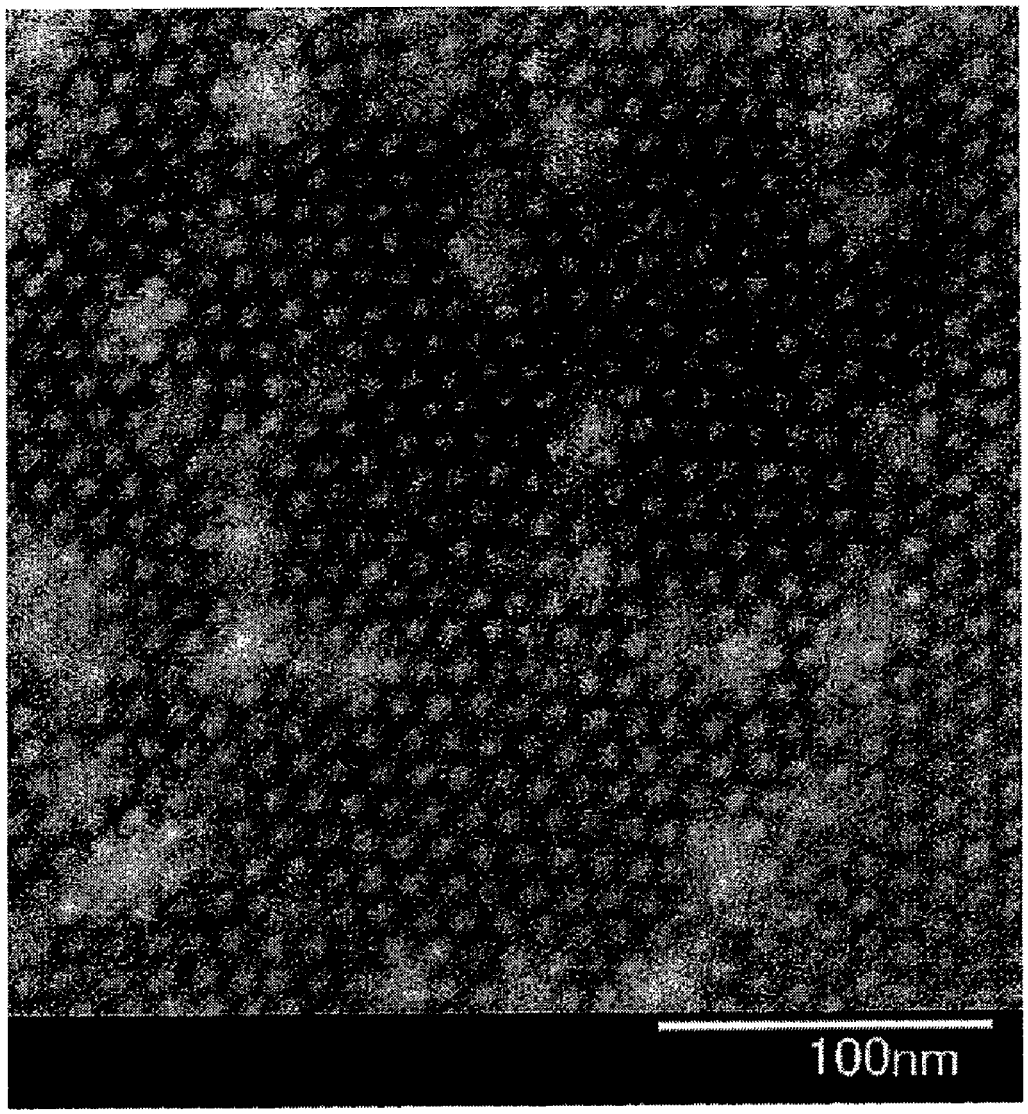
FIG. 37 shows a photograph illustrating the appearance of a two-dimensional array of ferritin obtained in Comparative Example 13.
Figure 38:
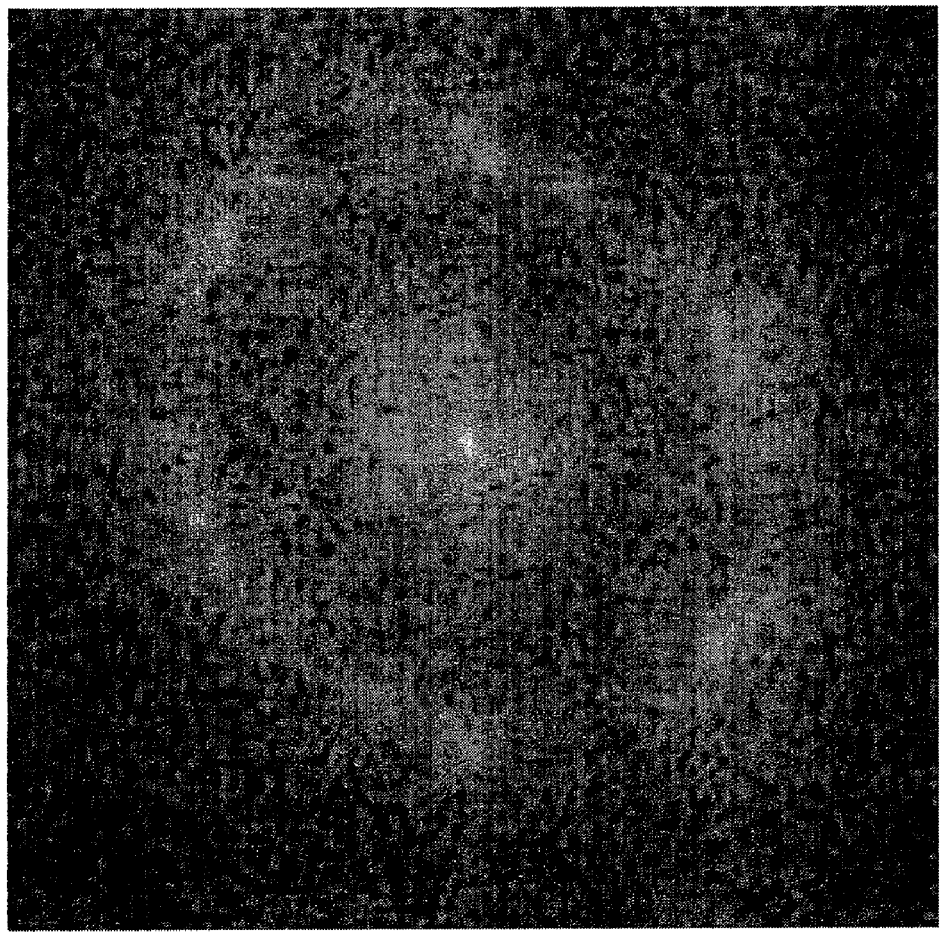
FIG. 38 shows a photograph of Fourier transformation image illustrating the appearance of a two-dimensional array of ferritin obtained in Comparative Example 13.

A photograph illustrating the appearance of a two-dimensional array of ferritin obtained using 0.5 mg/ml P7S-Fer0 (In) and 13 mM ammonium sulfate is shown in FIG. 37, and a Fourier transformation image thereof is shown in FIG. 38.

Comparative Example 14

Figure 39:
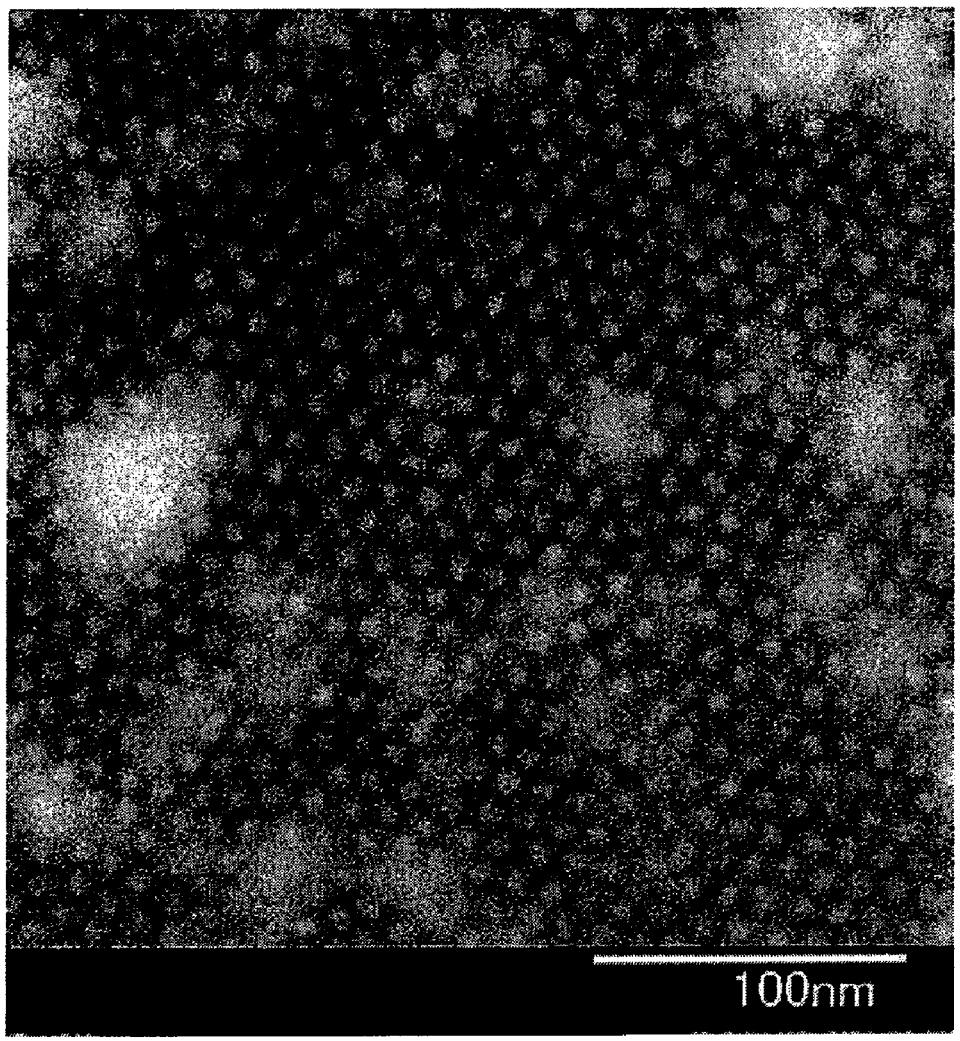
FIG. 39 shows a photograph illustrating the appearance of a two-dimensional array of ferritin obtained in Comparative Example 14.
Figure 40:
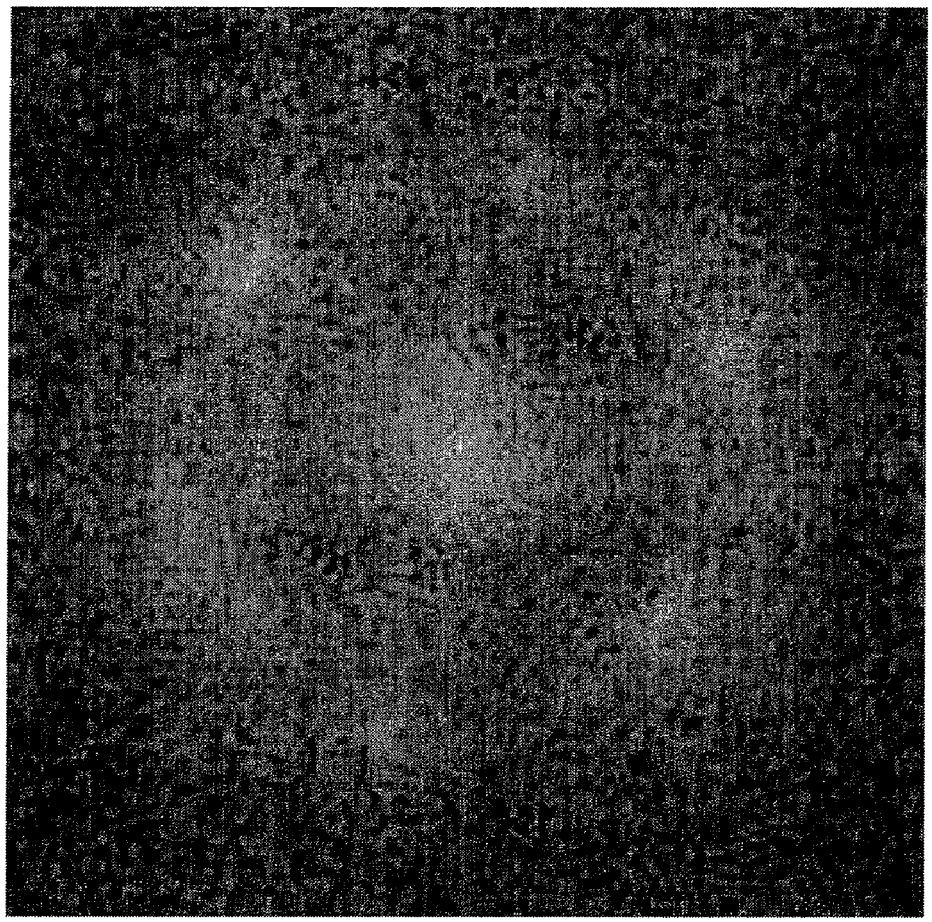
FIG. 40 shows a photograph of Fourier transformation image illustrating the appearance of a two-dimensional array of ferritin obtained in Comparative Example 14.

A photograph illustrating the appearance of a two-dimensional array of ferritin obtained using 0.5 mg/ml P7S-Fer0 (In) and 20 mM ammonium acetate is shown in FIG. 39, and a Fourier transformation image thereof is shown in FIG. 40.

It could be verified that the ferritin D2N-Fer0, E10Q-Fer0, E10S-Fer0 and P7S-Fer0 having an amino acid sequence with substitution by a different amino acid residue from N1-LF in conventional example on its outer peripheral surface formed "favorable" or "inferior" two-dimensional array.

Comparative Example 15

Figure 41:
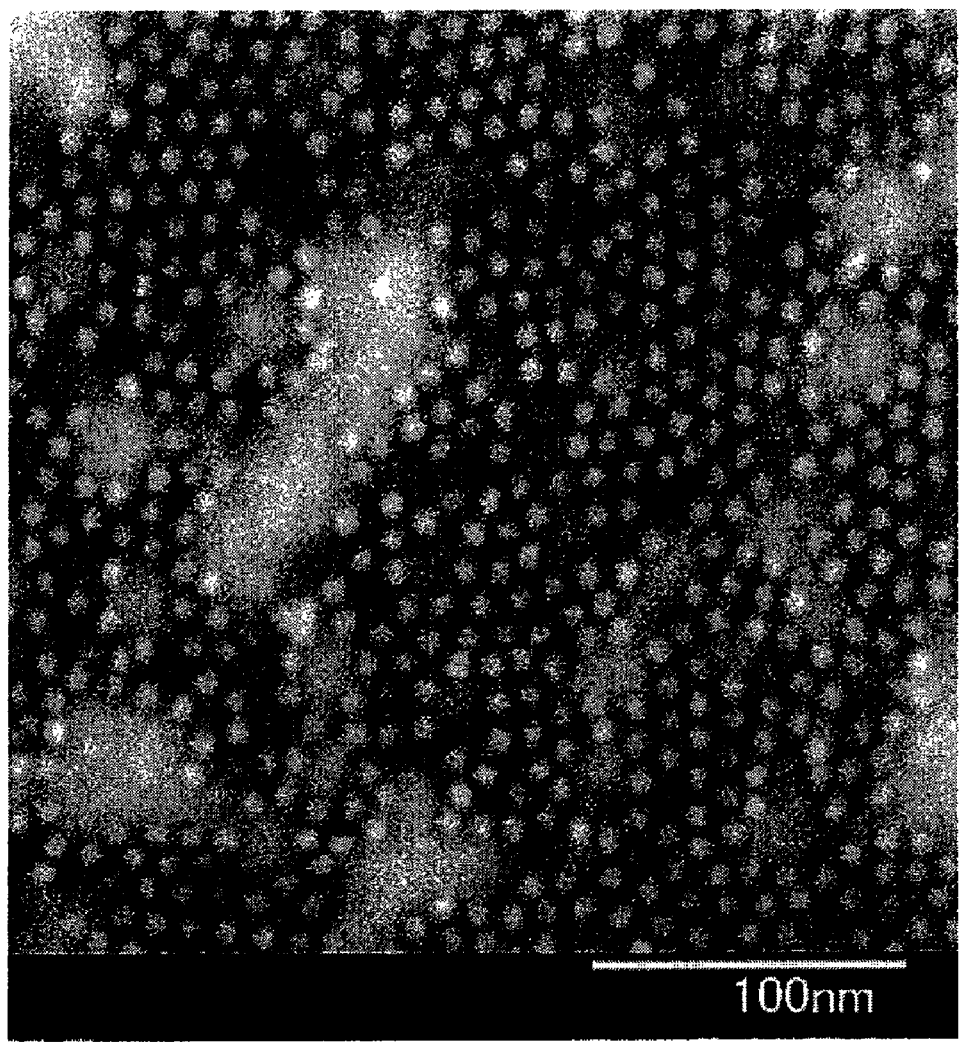
FIG. 41 shows a photograph illustrating the appearance of a two-dimensional array of ferritin obtained in Comparative Example 15.
Figure 42:
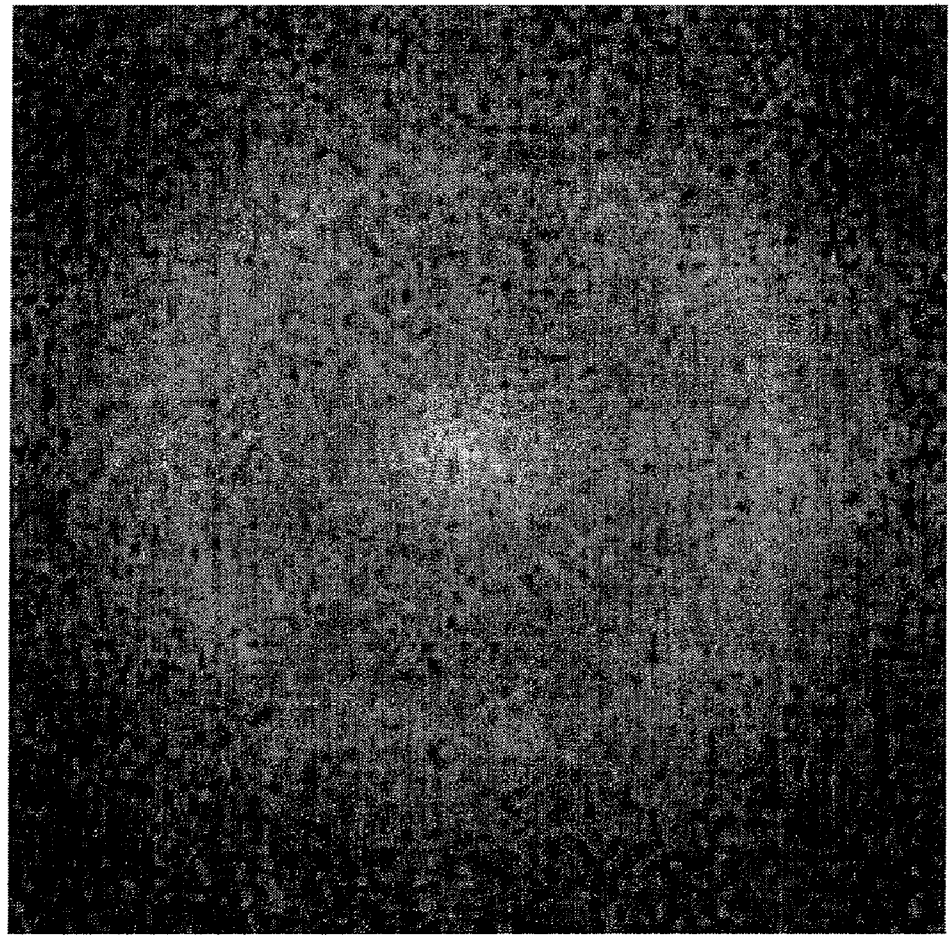
FIG. 42 shows a photograph of Fourier transformation image illustrating the appearance of a two-dimensional array of ferritin obtained in Comparative Example 15.

A photograph illustrating the appearance of a two-dimensional array of ferritin obtained using 0.5 mg/ml Y8FY9F-Fer0 (In) and 12.5 mM PIPES-NaOH (pH 7.0) is shown in FIG. 41, and a Fourier transformation image thereof is shown in FIG. 42.

Comparative Example 16

A photograph illustrating the appearance of a two-dimensional array of ferritin obtained using 0.5 mg/ml Y8FY9F-

Figure 43:
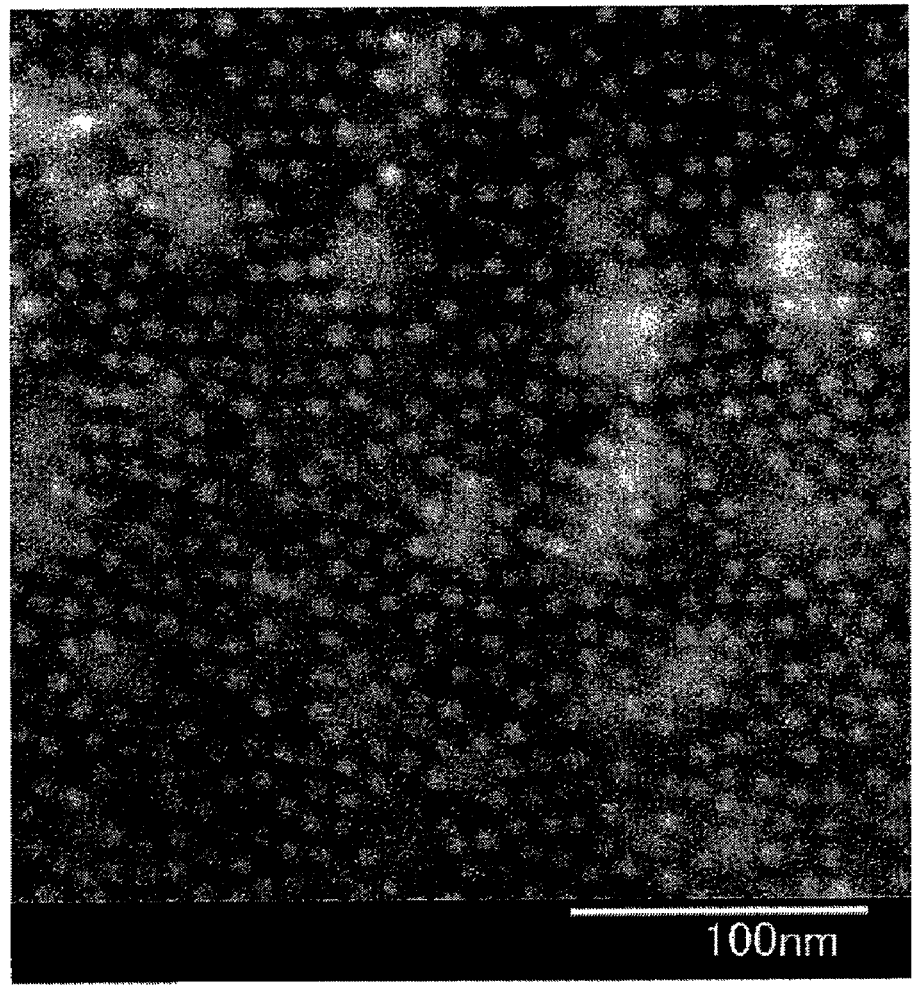
FIG. 43 shows a photograph illustrating the appearance of a two-dimensional array of ferritin obtained in Comparative Example 16.
Figure 44:
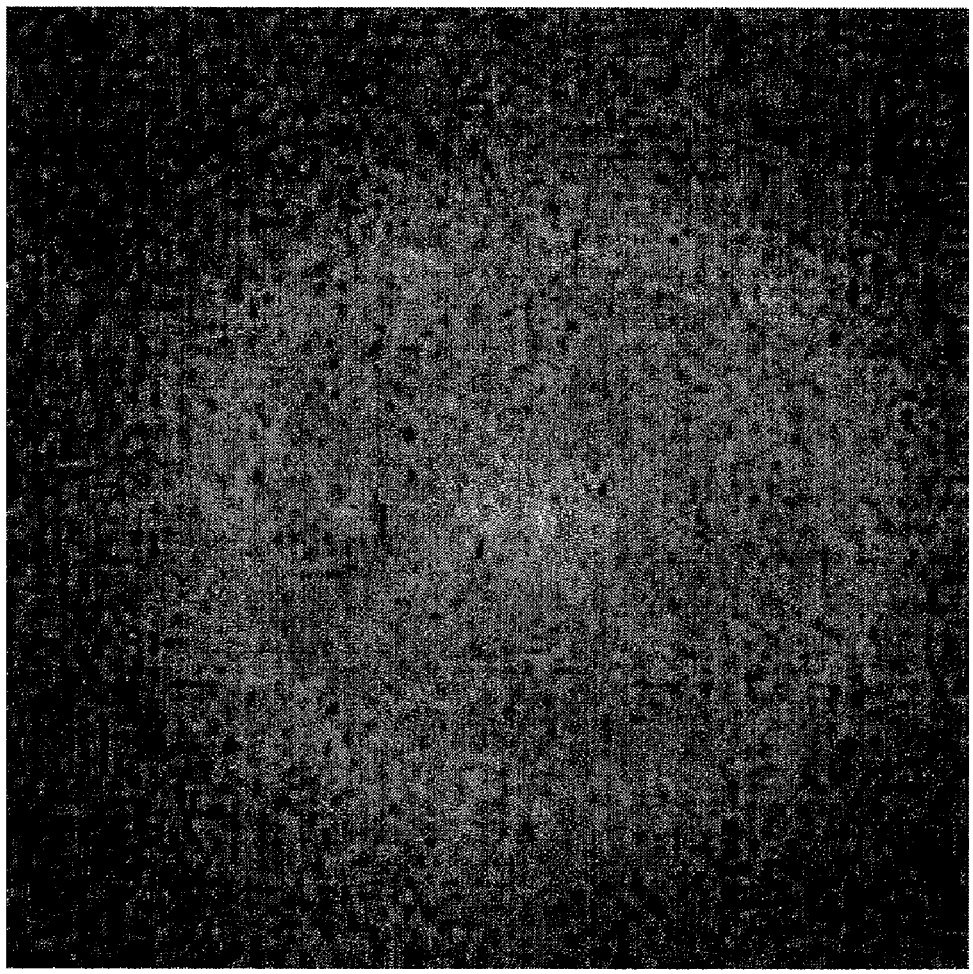
FIG. 44 shows a photograph of Fourier transformation image illustrating the appearance of a two-dimensional array of ferritin obtained in Comparative Example 16.

Fer0 (In) and 12.5 mM PIPES-Tris (pH 7.0) is shown in FIG. 43, and a Fourier transformation image thereof is shown in FIG. 44.

Comparative Example 17

Figure 45:
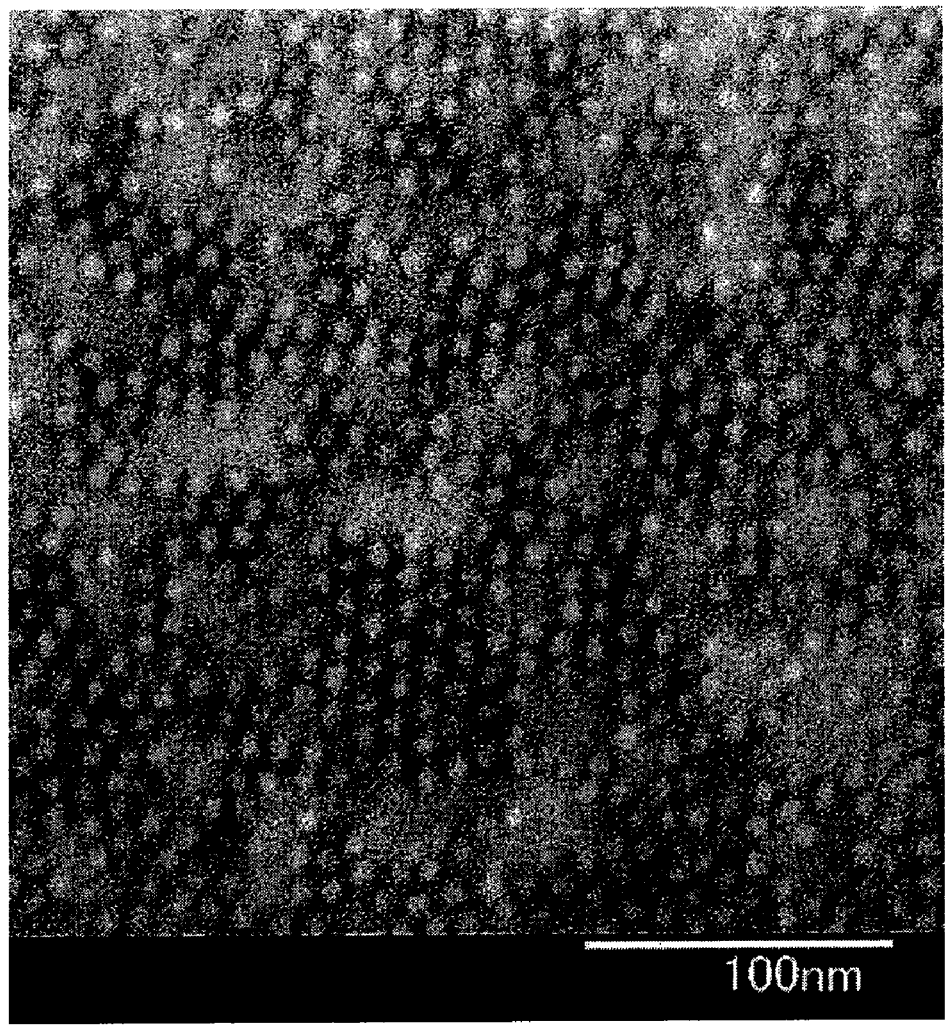
FIG. 45 shows a photograph illustrating the appearance of a two-dimensional array of ferritin obtained in Comparative Example 17.
Figure 46:
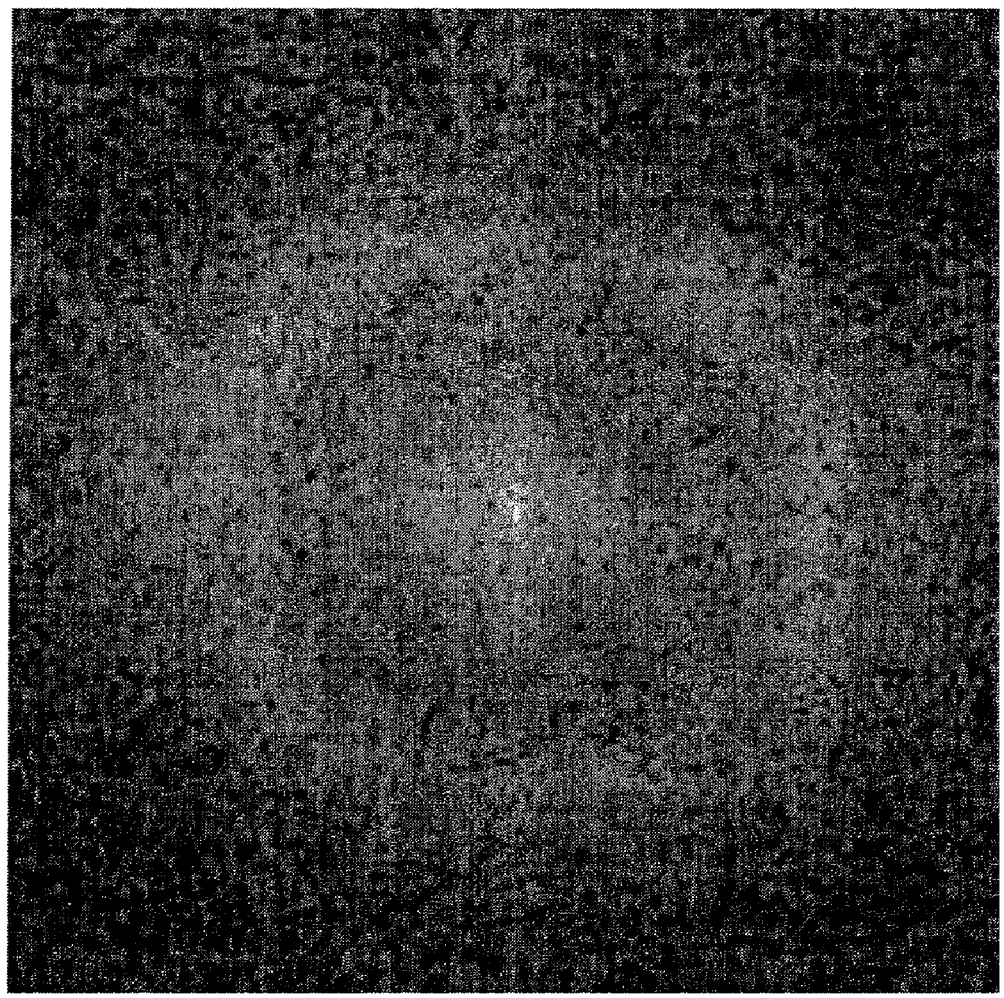
FIG. 46 shows a photograph of Fourier transformation image illustrating the appearance of a two-dimensional array of ferritin obtained in Comparative Example 17.

A photograph illustrating the appearance of a two-dimensional array of ferritin obtained using 0.5 mg/ml Y8FY9F-Fer0 (In) and 13 mM ammonium sulfate is shown in FIG. 45, and a Fourier transformation image thereof is shown in FIG. 46.

Comparative Example 18

Figure 47:
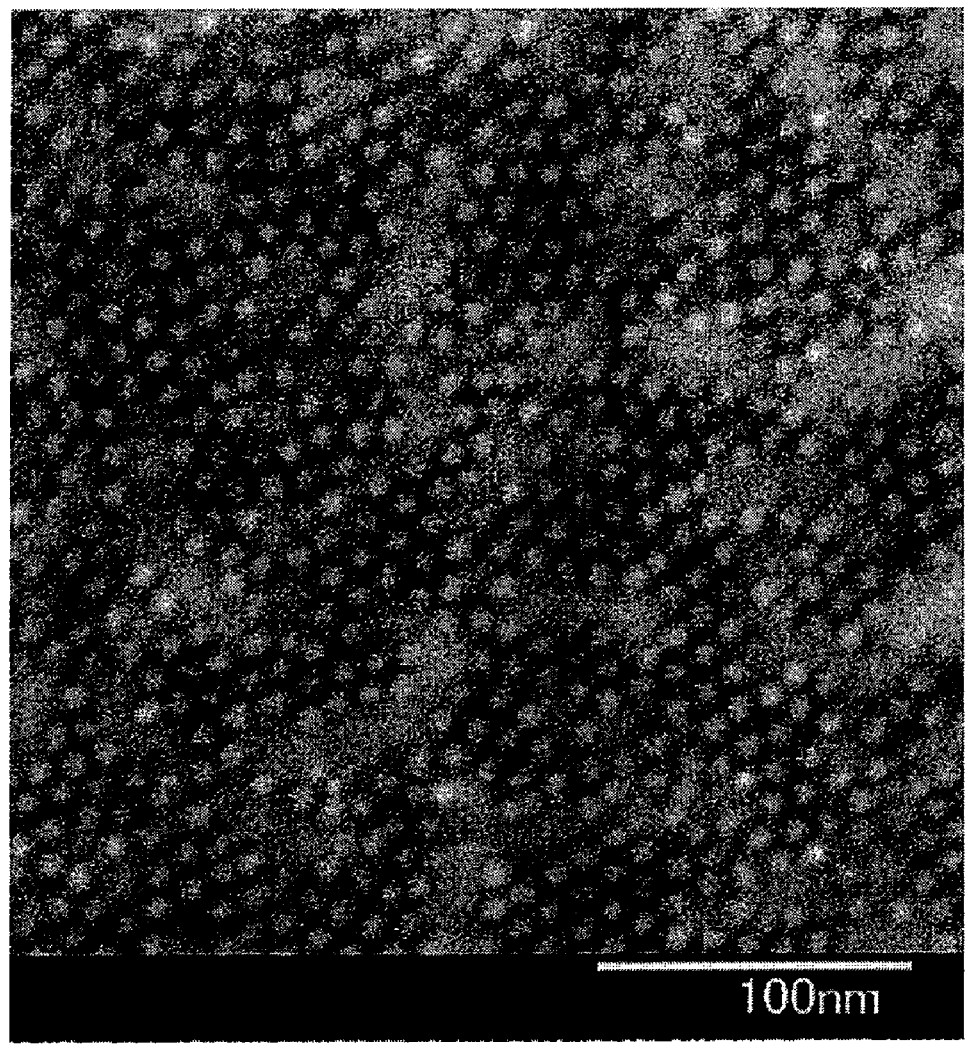
FIG. 47 shows a photograph illustrating the appearance of a two-dimensional array of ferritin obtained in Comparative Example 18.
Figure 48:
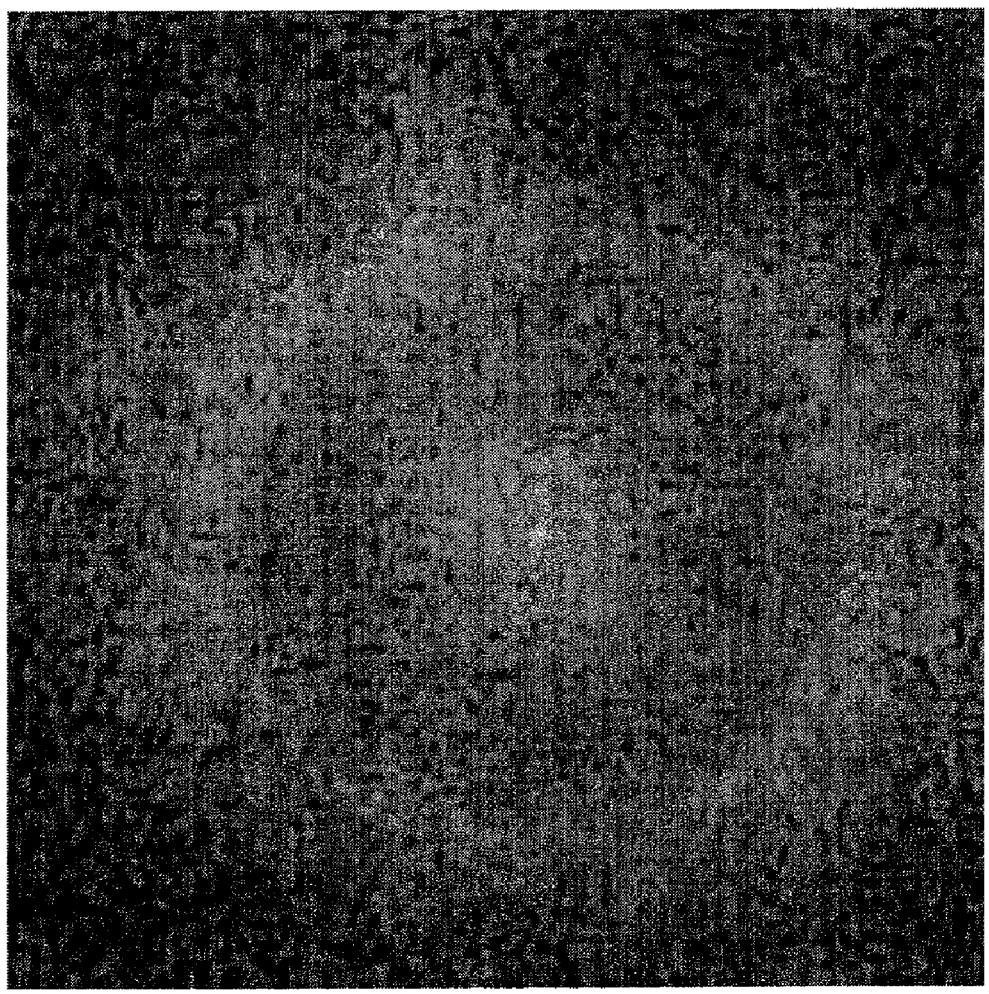
FIG. 48 shows a photograph of Fourier transformation image illustrating the appearance of a two-dimensional array of ferritin obtained in Comparative Example 18.

A photograph illustrating the appearance of a two-dimensional array of ferritin obtained using 0.5 mg/ml S5TS6T-Fer0 (In) and 20 mM ammonium acetate is shown in FIG. 47, and a Fourier transformation image thereof is shown in FIG. 48.

Comparative Example 19

Figure 49:
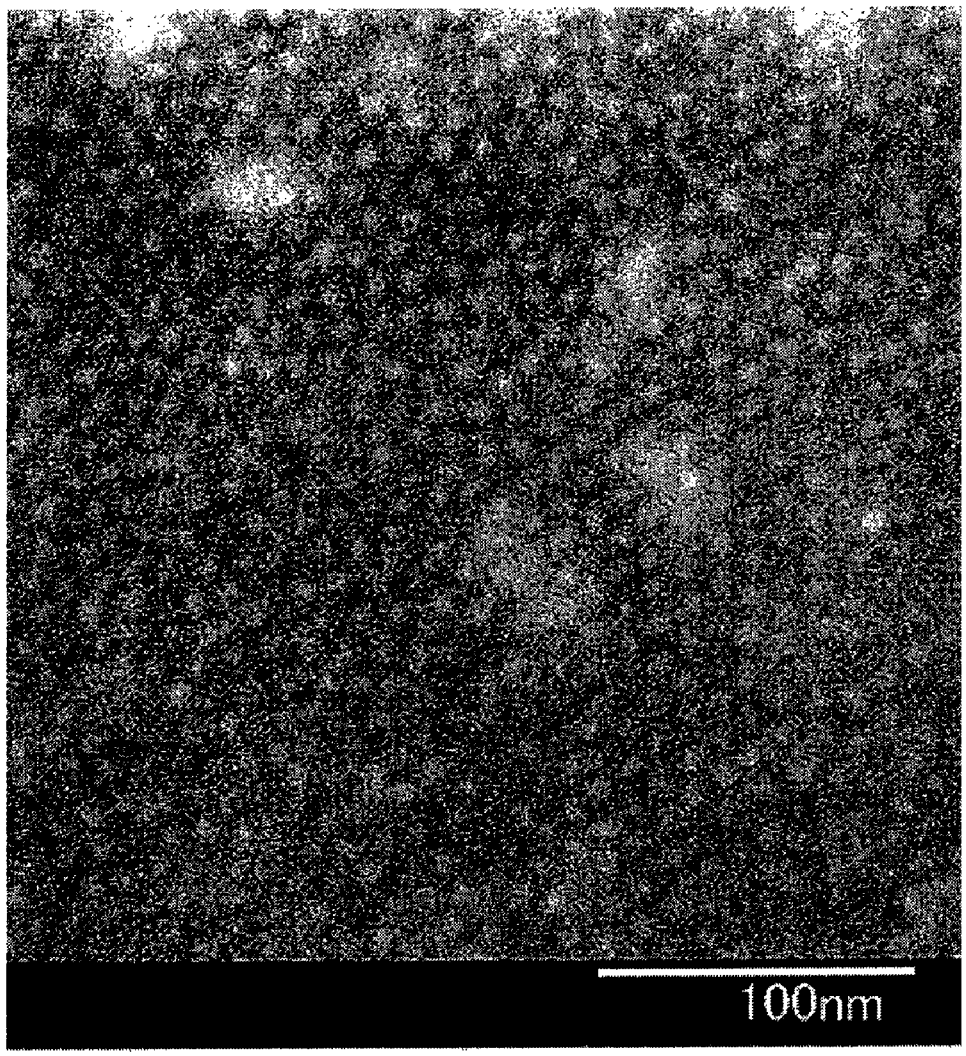
FIG. 49 shows a photograph illustrating the appearance of a two-dimensional array of ferritin obtained in Comparative Example 19.
Figure 50:
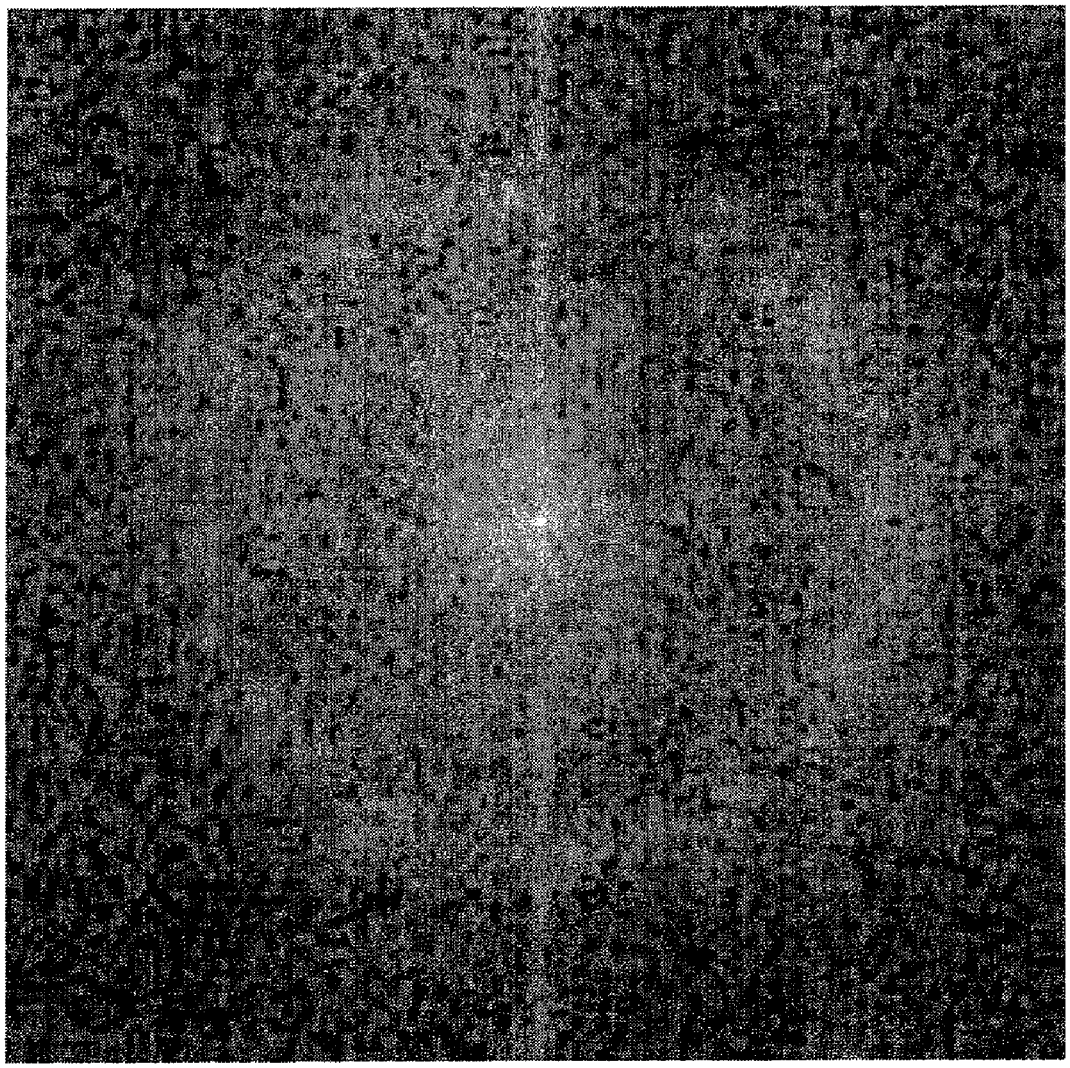
FIG. 50 shows a photograph of Fourier transformation image illustrating the appearance of a two-dimensional array of ferritin obtained in Comparative Example 19.

A photograph illustrating the appearance of a two-dimensional array of ferritin obtained using 0.5 mg/ml S5TS6T-Fer0 (In) and 13 mM ammonium sulfate is shown in FIG. 49, and a Fourier transformation image thereof is shown in FIG. 50.

Comparative Example 20

Figure 51:
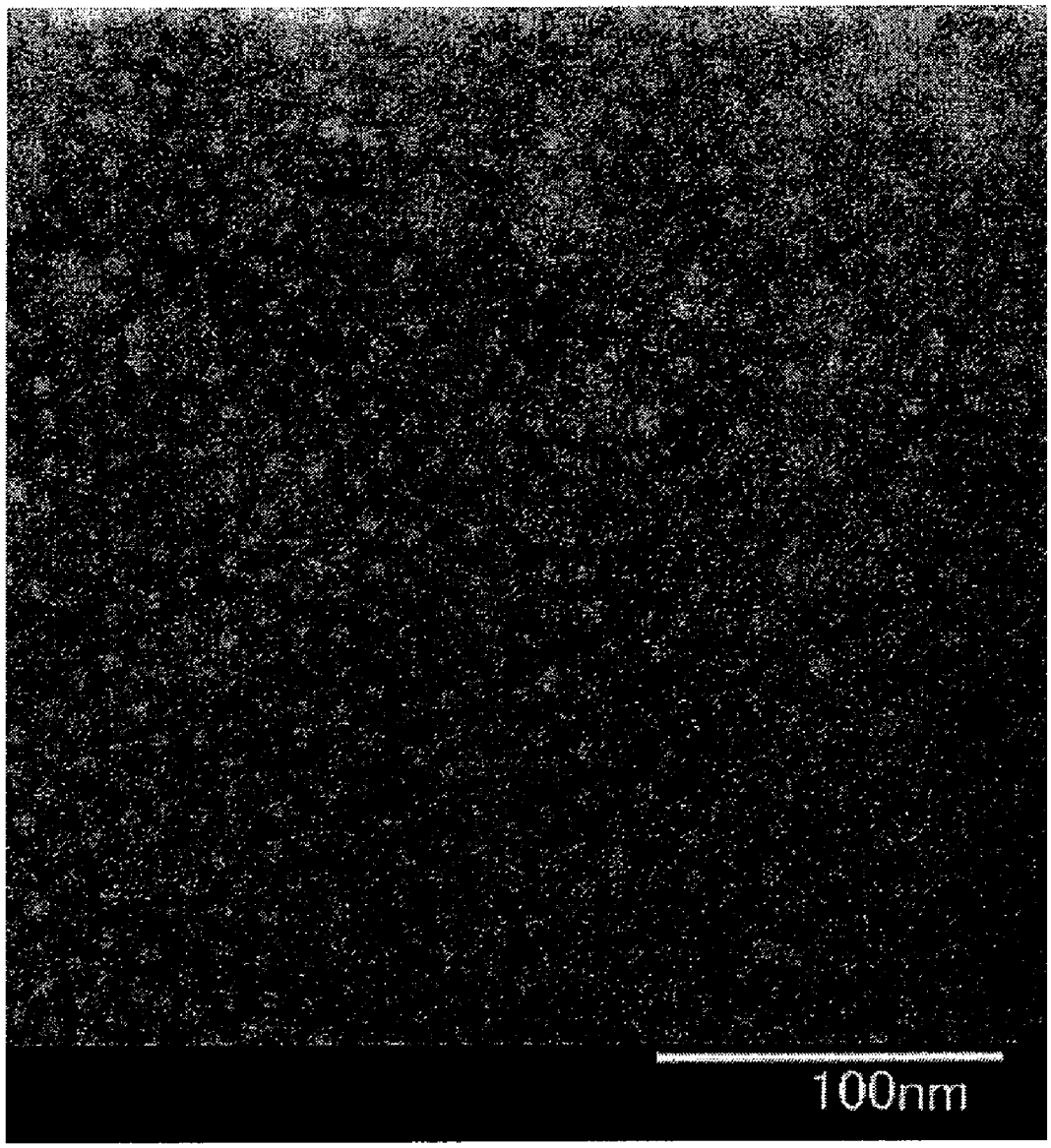
FIG. 51 shows a photograph illustrating the appearance of a two-dimensional array of ferritin obtained in Comparative Example 20.
Figure 52:
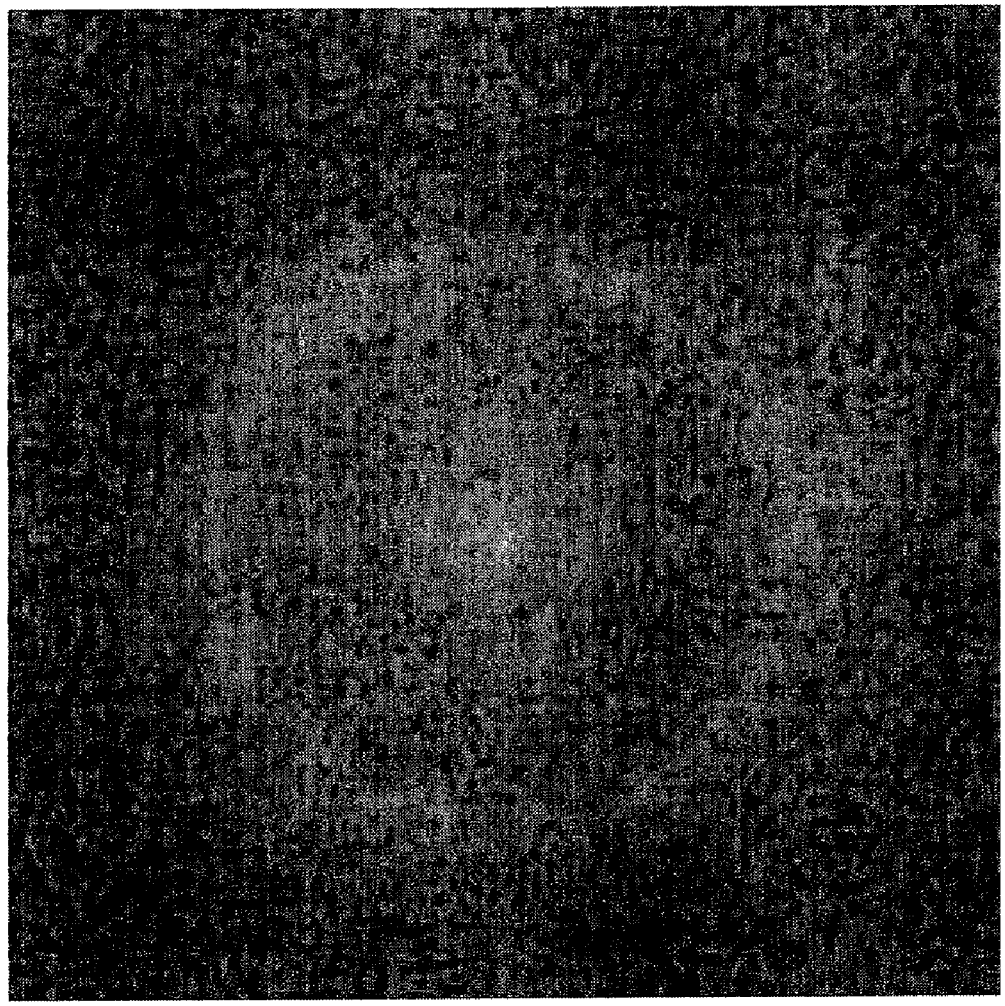
FIG. 52 shows a photograph of Fourier transformation image illustrating the appearance of a two-dimensional array of ferritin obtained in Comparative Example 20.

A photograph illustrating the appearance of a two-dimensional array of ferritin obtained using 0.5 mg/ml S5TS6T-Fer0 (In) and 20 mM ammonium acetate is shown in FIG. 51, and a Fourier transformation image thereof is shown in FIG. 52.

It could be verified that the ferritin Y8FY9F-Fer0 and S5TS6T-Fer0 having an amino acid sequence with substitution by two different amino acid residues from N1-LF in conventional example on its outer peripheral surface formed "inferior two-dimensional array".

Comparative Example 21

Figure 53:
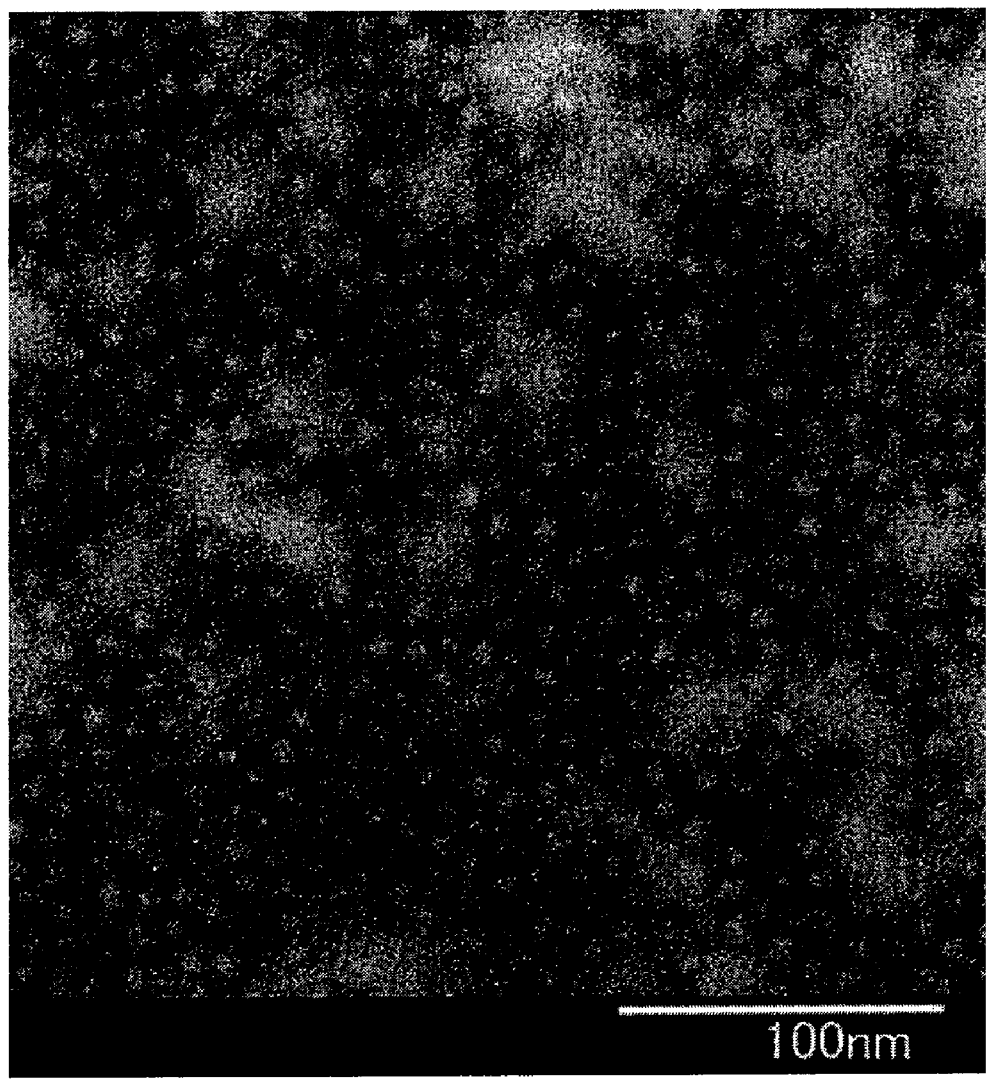
FIG. 53 shows a photograph illustrating the appearance of a two-dimensional array of ferritin obtained in Comparative Example 21.
Figure 54:
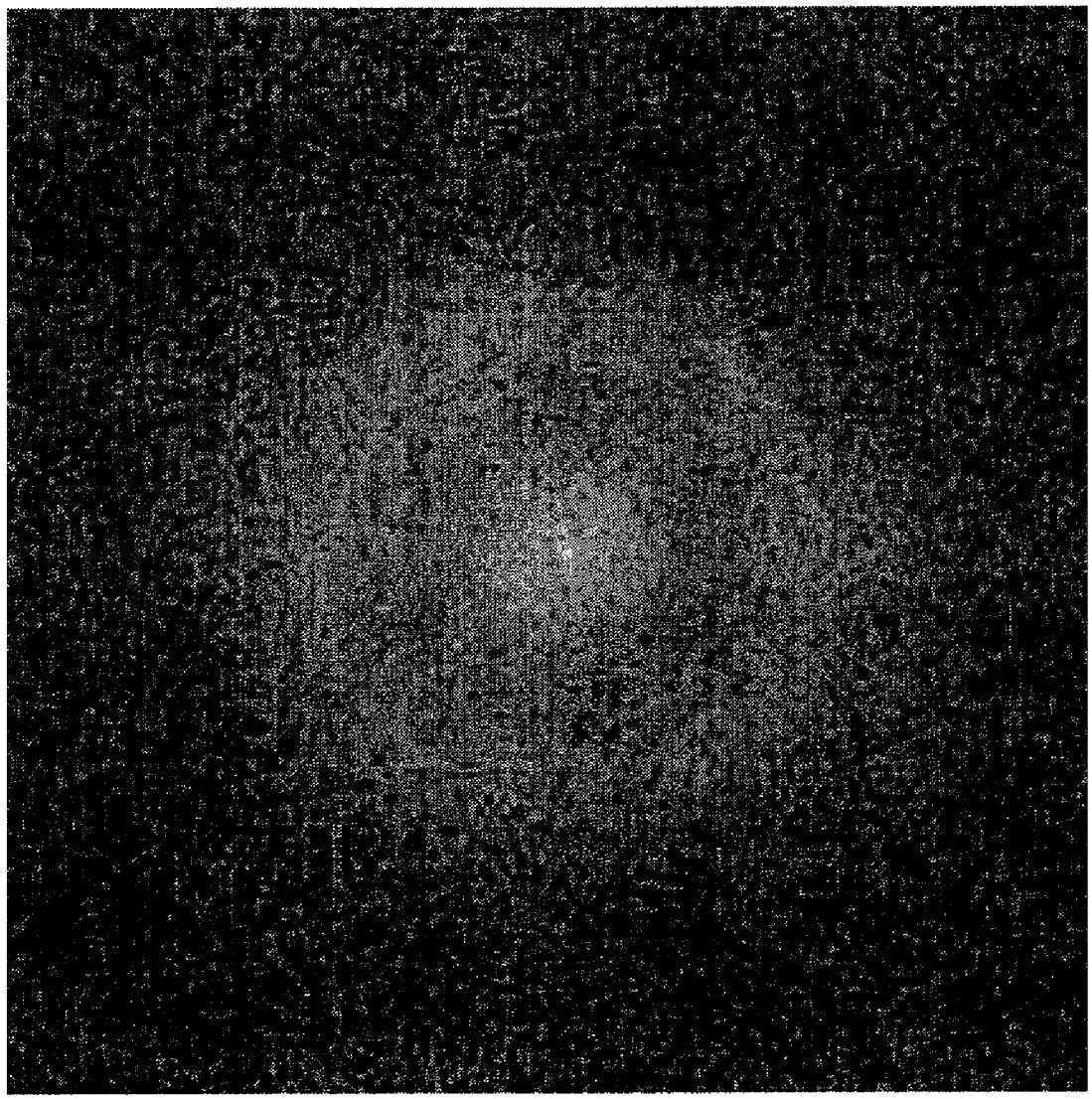
FIG. 54 shows a photograph of Fourier transformation image illustrating the appearance of a two-dimensional array of ferritin obtained in Comparative Example 21.

A photograph illustrating the appearance of attachment of ferritin obtained using 0.5 mg/ml ΔHY-Fer0 (In) and 12.5 mM PIPES-NaOH (pH 7.0) is shown in FIG. 53, and a Fourier transformation image thereof is shown in FIG. 54.

Comparative Example 22

Figure 55:
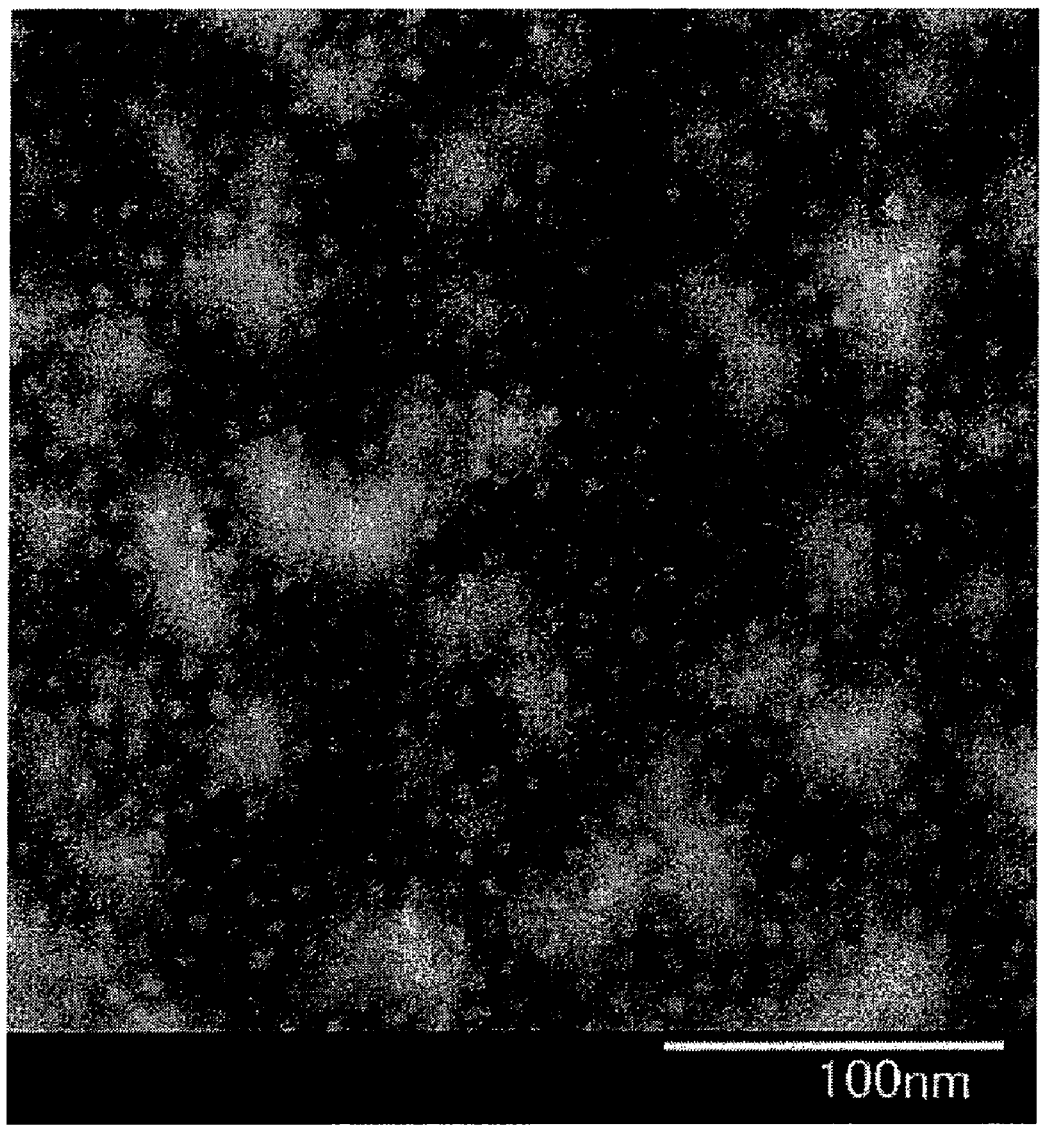
FIG. 55 shows a photograph illustrating the appearance of a two-dimensional array of ferritin obtained in Comparative Example 22.
Figure 56:
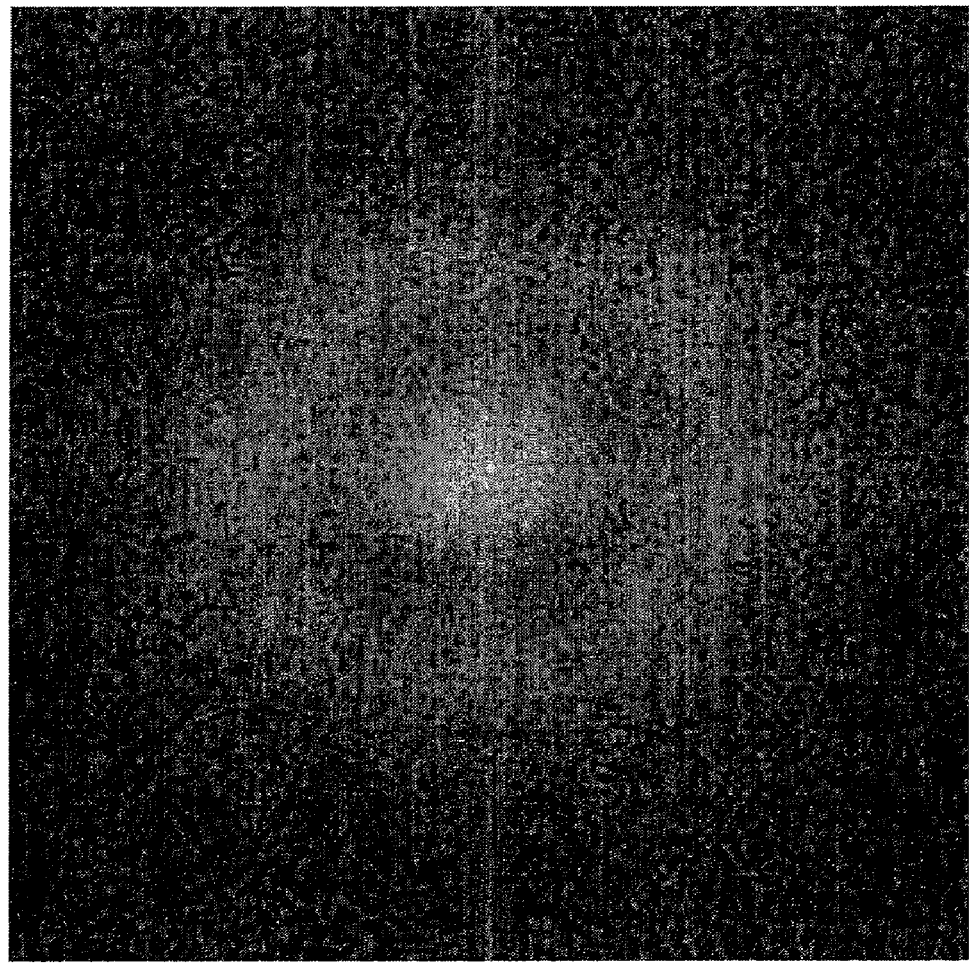
FIG. 56 shows a photograph of Fourier transformation image illustrating the appearance of a two-dimensional array of ferritin obtained in Comparative Example 22.

A photograph illustrating the appearance of attachment of ferritin obtained using 0.5 mg/ml ΔHY-Fer0 (In) and 13 mM ammonium sulfate is shown in FIG. 55, and a Fourier transformation image thereof is shown in FIG. 56.

Comparative Example 23

Figure 57:
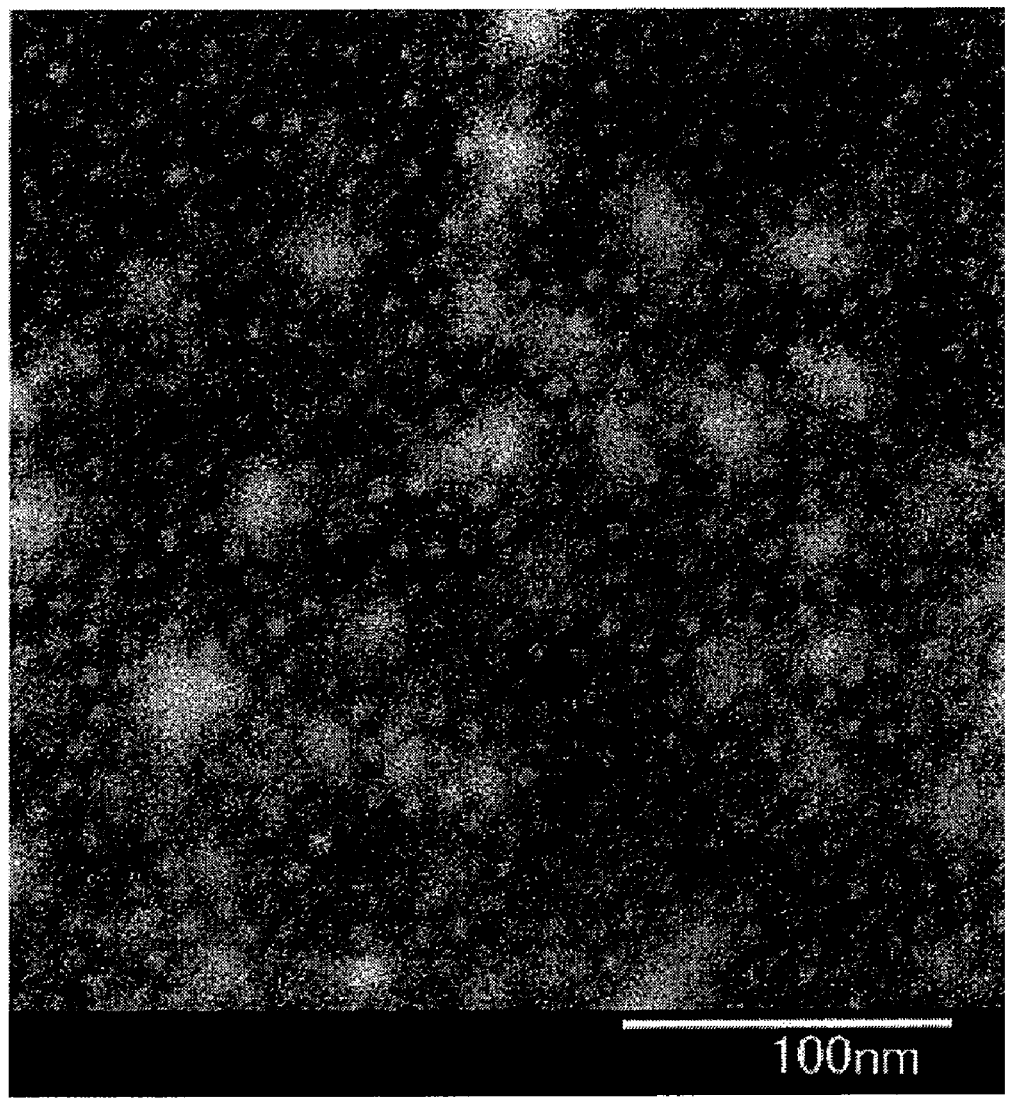
FIG. 57 shows a photograph illustrating the appearance of a two-dimensional array of ferritin obtained in Comparative Example 23.
Figure 58:
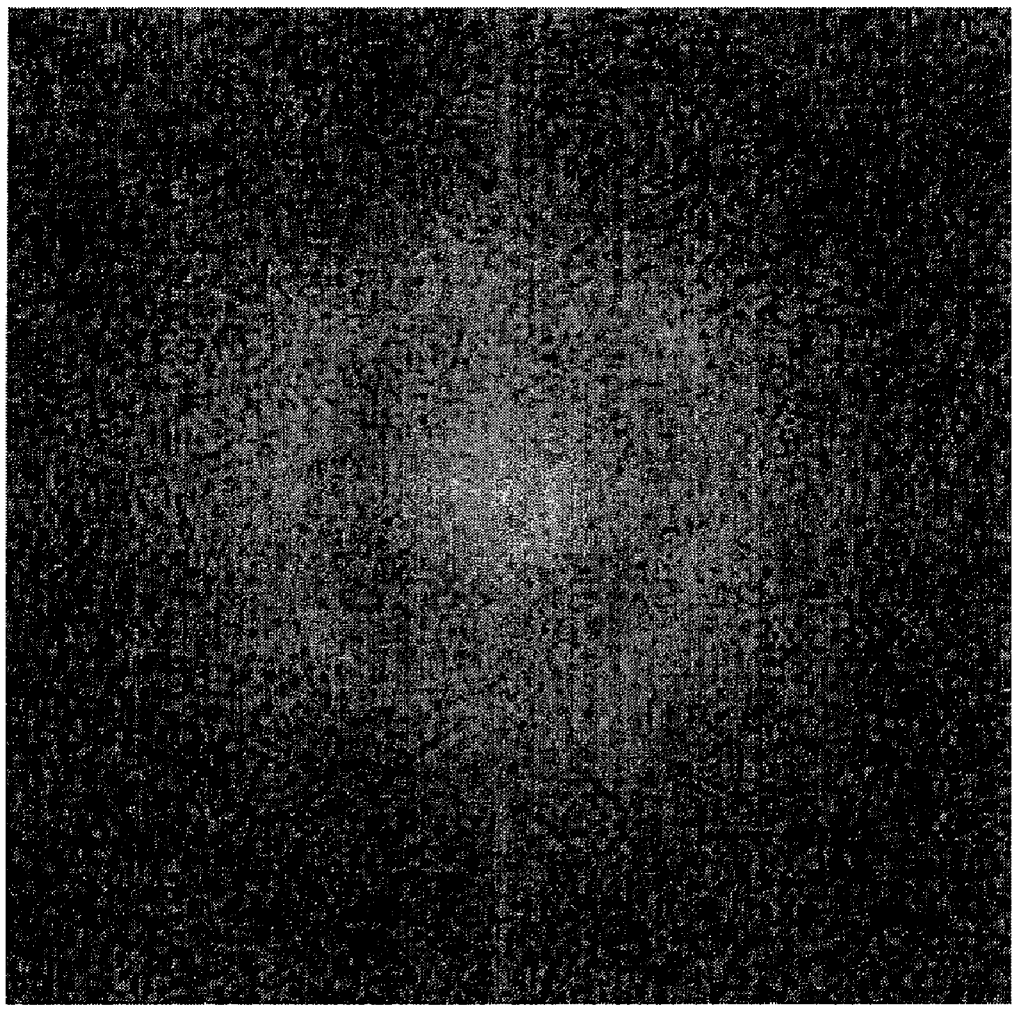
FIG. 58 shows a photograph of Fourier transformation image illustrating the appearance of a two-dimensional array of ferritin obtained in Comparative Example 23.

A photograph illustrating the appearance of attachment of ferritin obtained using 0.5 mg/ml ΔHY-Fer0 (In), and 20 mM ammonium acetate is shown in FIG. 57, and a Fourier transformation image thereof is shown in FIG. 58.

It could be verified that the ferritin ΔHY-Fer0 having an amino acid sequence with substitution by five different amino acid residues from N1-LF in conventional example on its outer peripheral surface did not form a two-dimensional array.

Comparative Example 24

Figure 59:
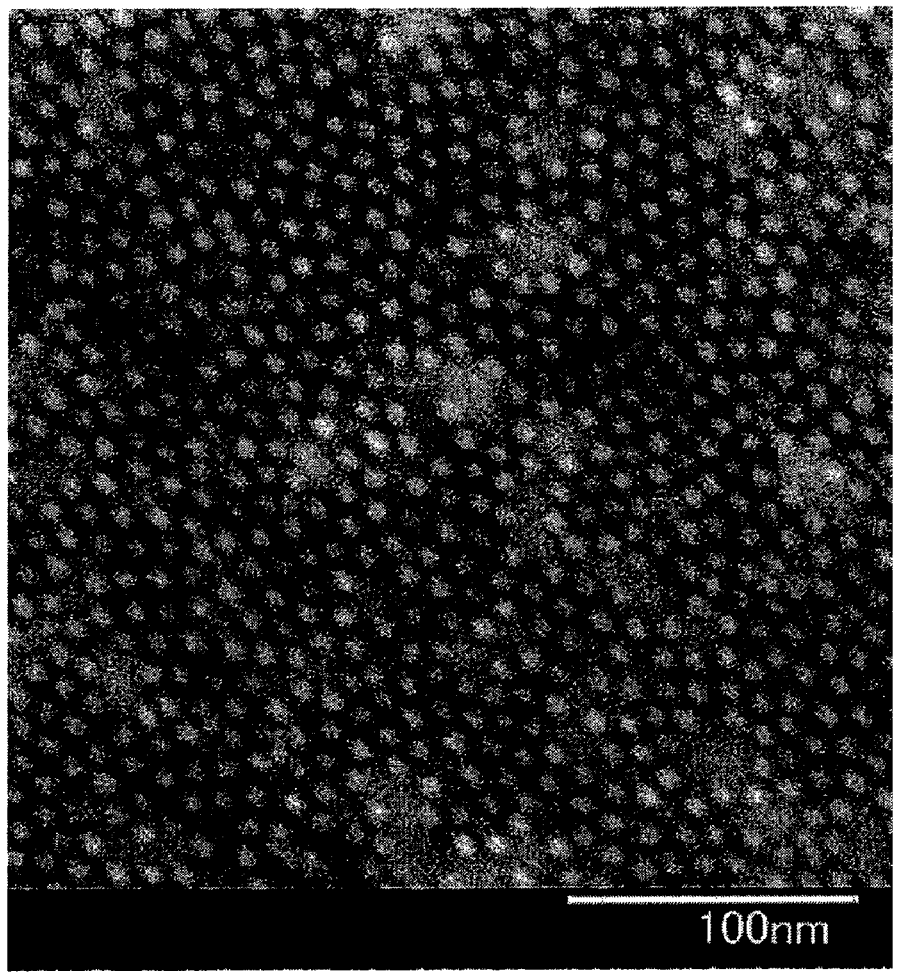
FIG. 59 shows a photograph illustrating the appearance of a two-dimensional array of ferritin obtained in Comparative Example 24.
Figure 60:
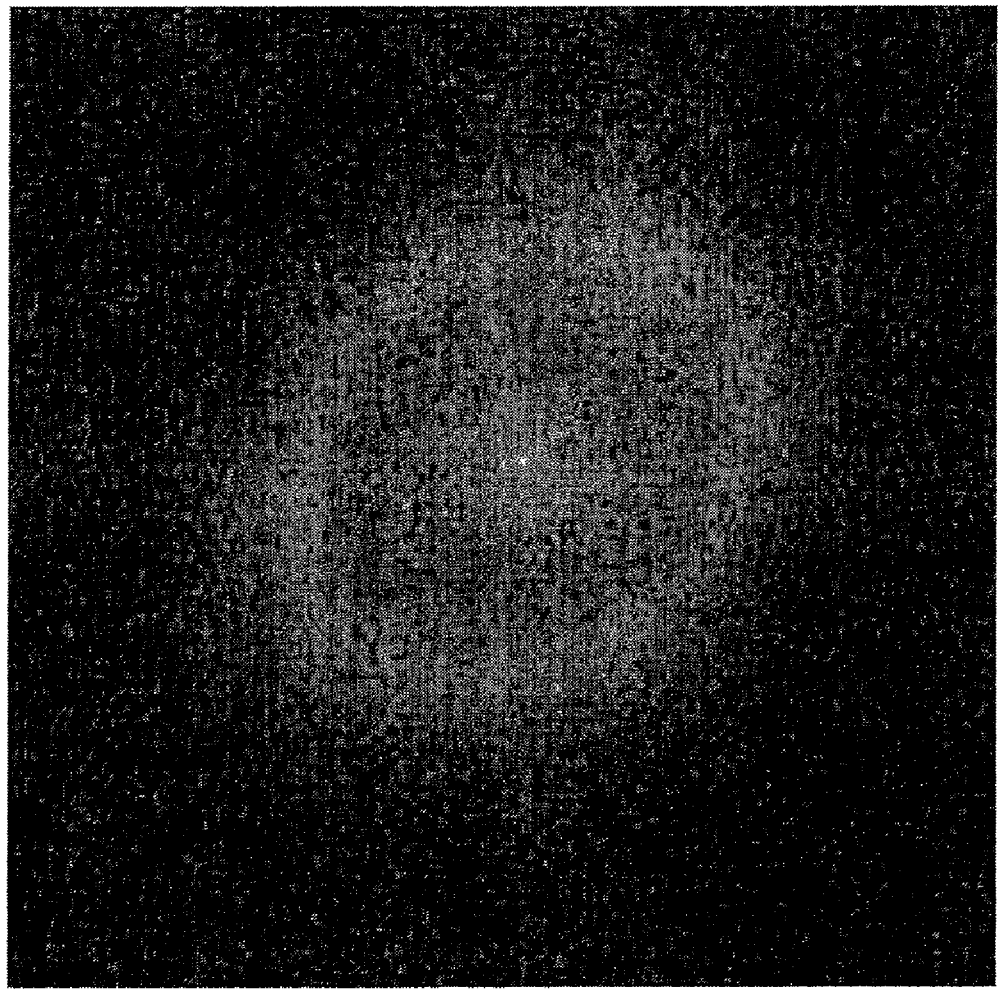
FIG. 60 shows a photograph of Fourier transformation image illustrating the appearance of a two-dimensional array of ferritin obtained in Comparative Example 24.

A photograph illustrating the appearance of a two-dimensional array of ferritin obtained using 0.5 mg/ml ΔR-Fer0 (In) and 12.5 mM PIPES-NaOH (pH 7.0) is shown in FIG. 59, and a Fourier transformation image thereof is shown in FIG. 60.

Comparative Example 25

Figure 61:
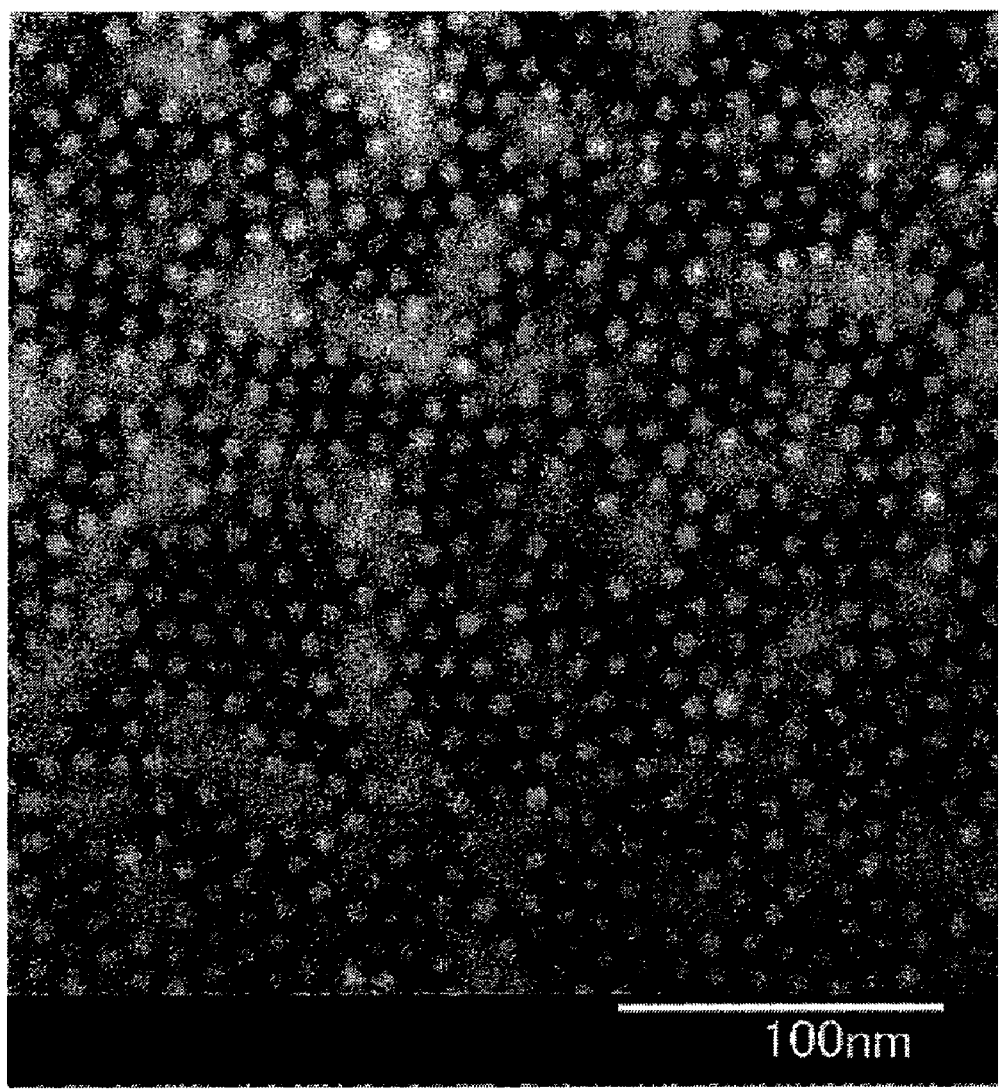
FIG. 61 shows a photograph illustrating the appearance of a two-dimensional array of ferritin obtained in Comparative Example 25.
Figure 62:
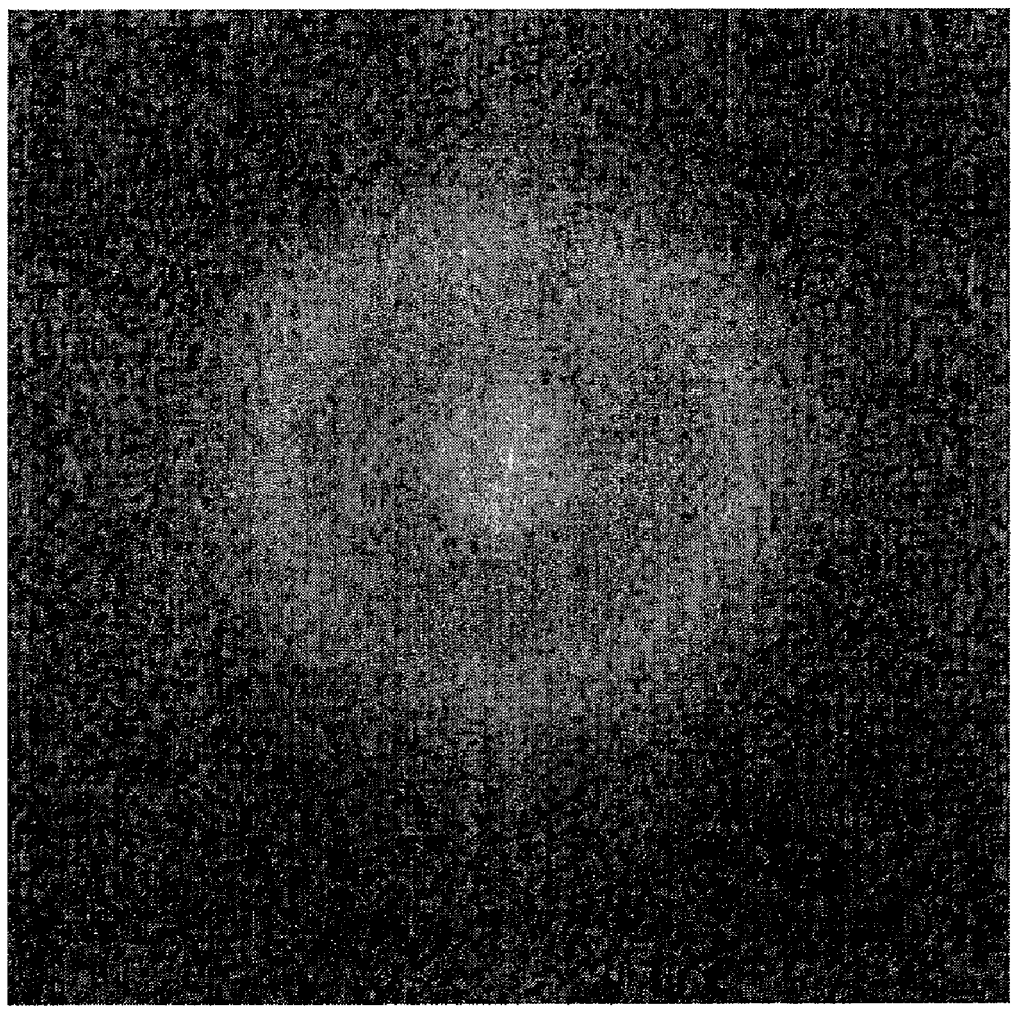
FIG. 62 shows a photograph of Fourier transformation image illustrating the appearance of a two-dimensional array of ferritin obtained in Comparative Example 25.

A photograph illustrating the appearance of a two-dimensional array of ferritin obtained using 0.5 mg/ml ΔAR-Fer0 (In) and 13 mM ammonium sulfate is shown in FIG. 61, and a Fourier transformation image thereof is shown in FIG. 62.

Comparative Example 26

Figure 63:
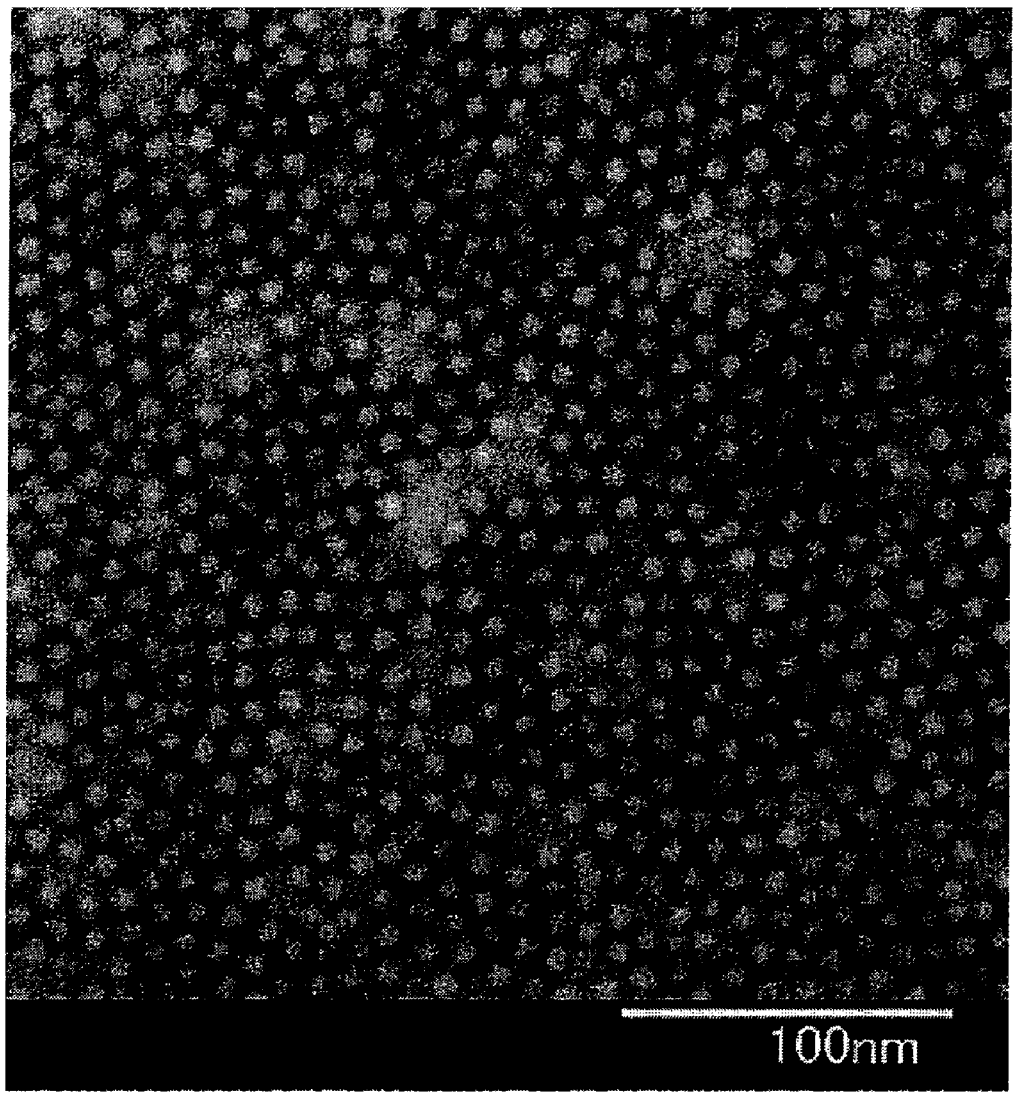
FIG. 63 shows a photograph illustrating the appearance of a two-dimensional array of ferritin obtained in Comparative Example 26.
Figure 64:
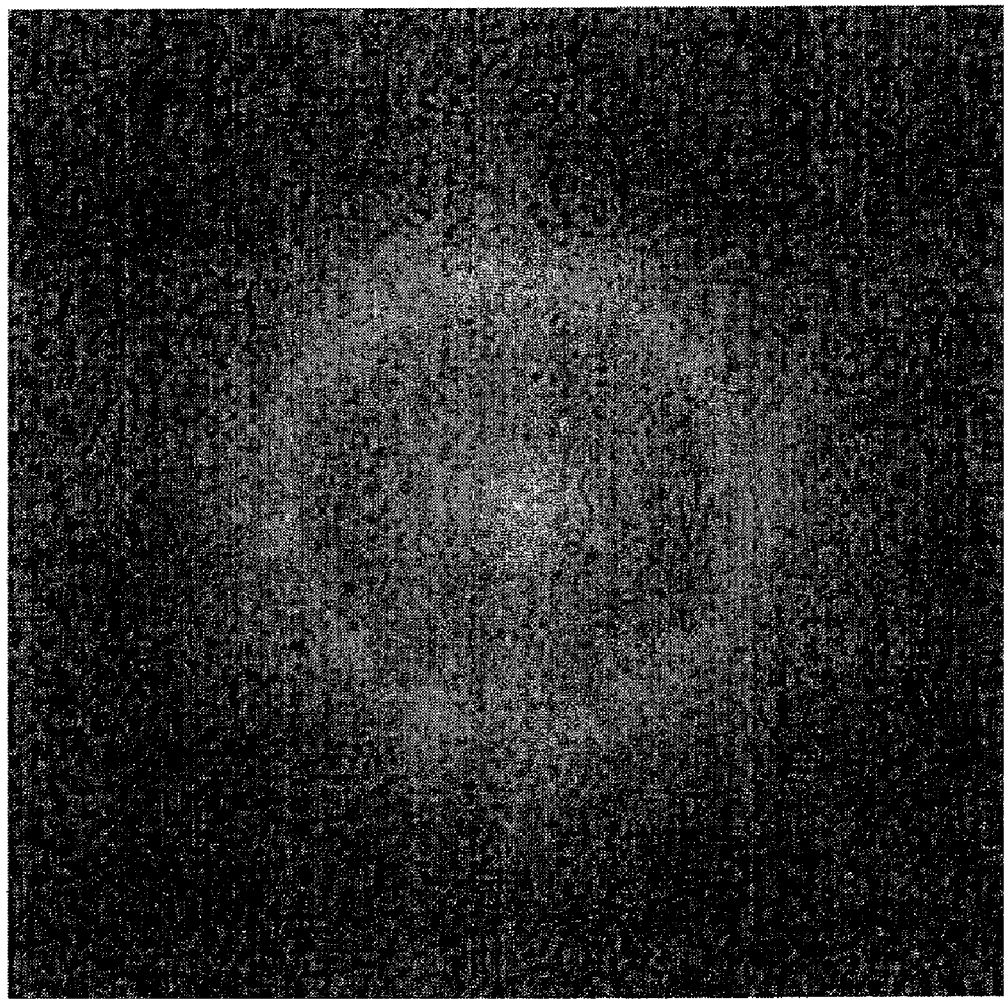
FIG. 64 shows a photograph of Fourier transformation image illustrating the appearance of a two-dimensional array of ferritin obtained in Comparative Example 26.

A photograph illustrating the appearance of a two-dimensional array of ferritin obtained using 0.5 mg/ml ΔAR-Fer0 (In) and 20 mM ammonium acetate is shown in FIG. 63, and a Fourier transformation image thereof is shown in FIG. 64.

It could be verified that the ferritin ΔAR-Fer0 having an amino acid sequence with substitution by five different amino acid residues from N1-LF in conventional example on its outer peripheral surface formed "favorable two-dimensional array" or "inferior two-dimensional array".

Comparative Example 27

Figure 65:
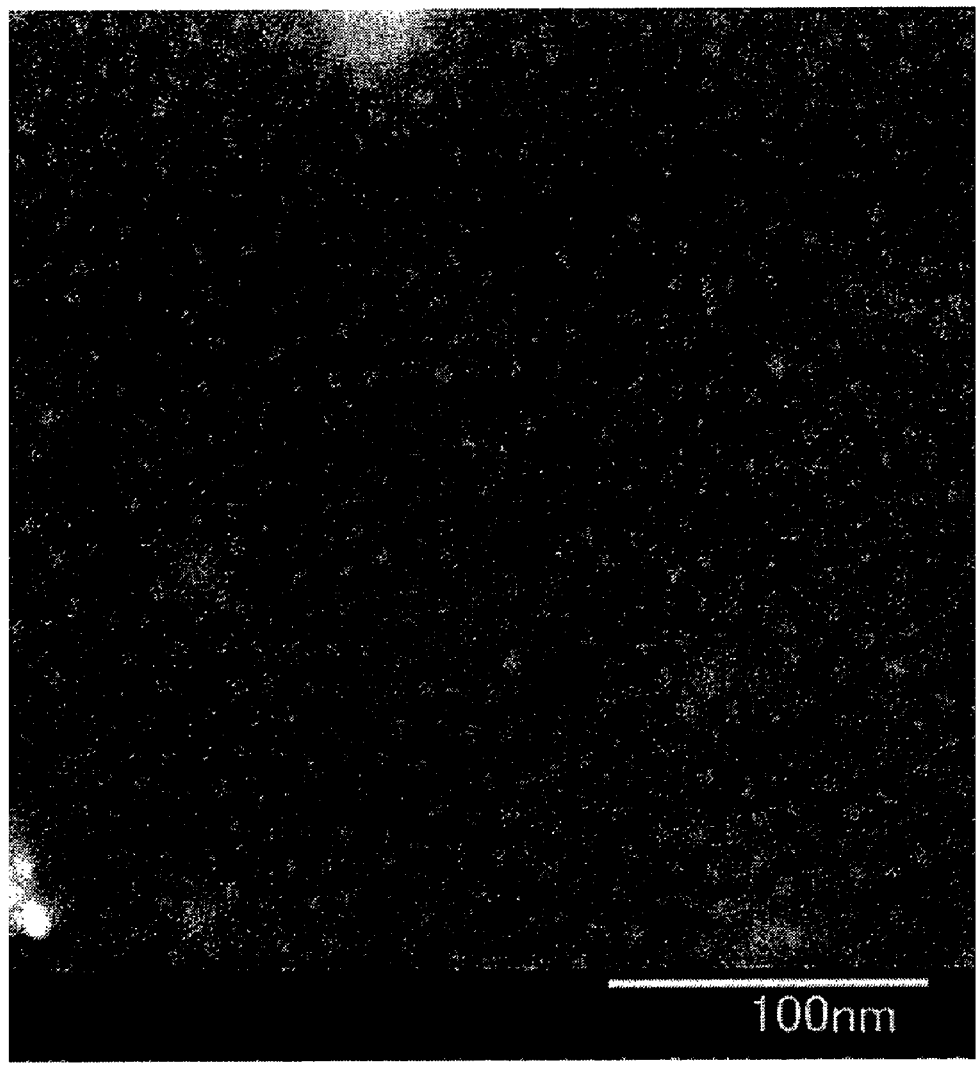
FIG. 65 shows a photograph illustrating the appearance of a two-dimensional array of ferritin obtained in Comparative Example 27.
Figure 66:
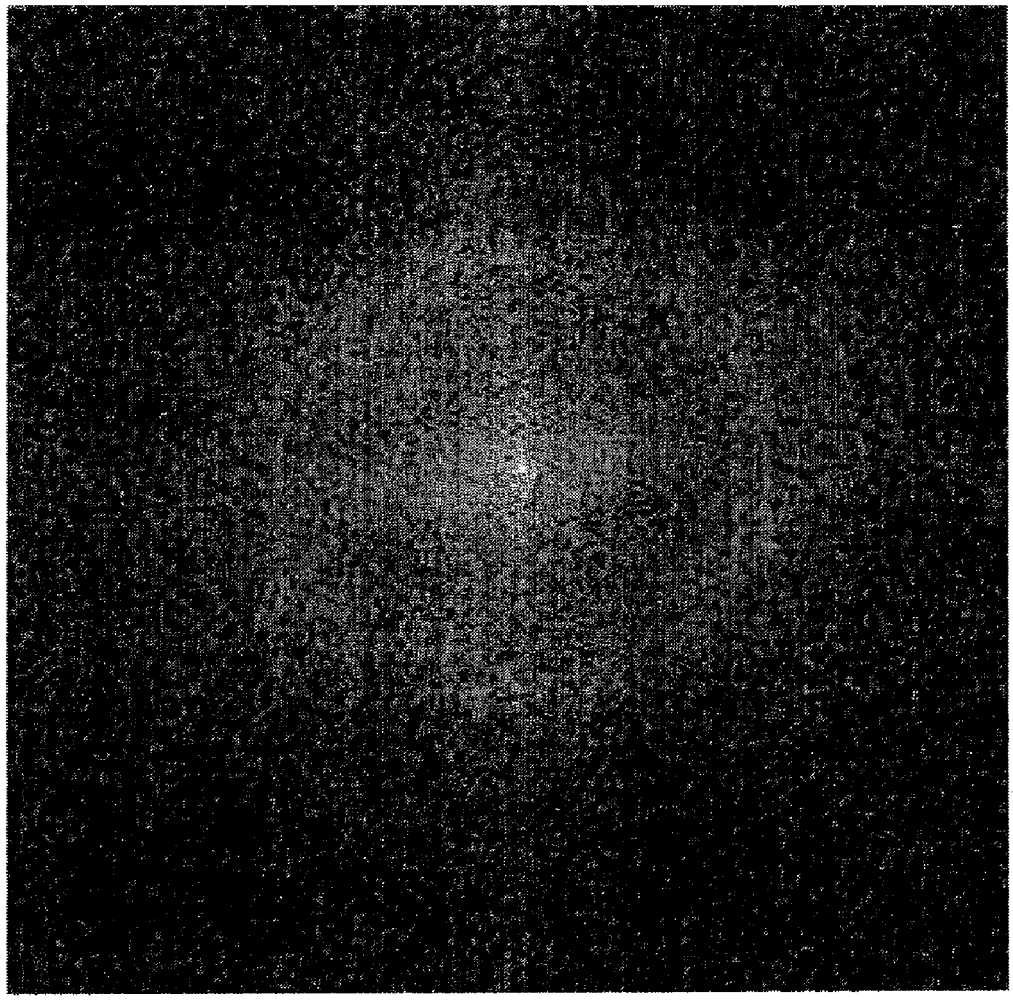
FIG. 66 shows a photograph of Fourier transformation image illustrating the appearance of a two-dimensional array of ferritin obtained in Comparative Example 27.

A photograph illustrating the appearance of a two-dimensional array of ferritin obtained using 0.5 mg/ml Shuffle-Fer0 (In) and 13 mM ammonium sulfate is shown in FIG. 65, and a Fourier transformation image thereof is shown in FIG. 66.

Comparative Example 28

Figure 67:
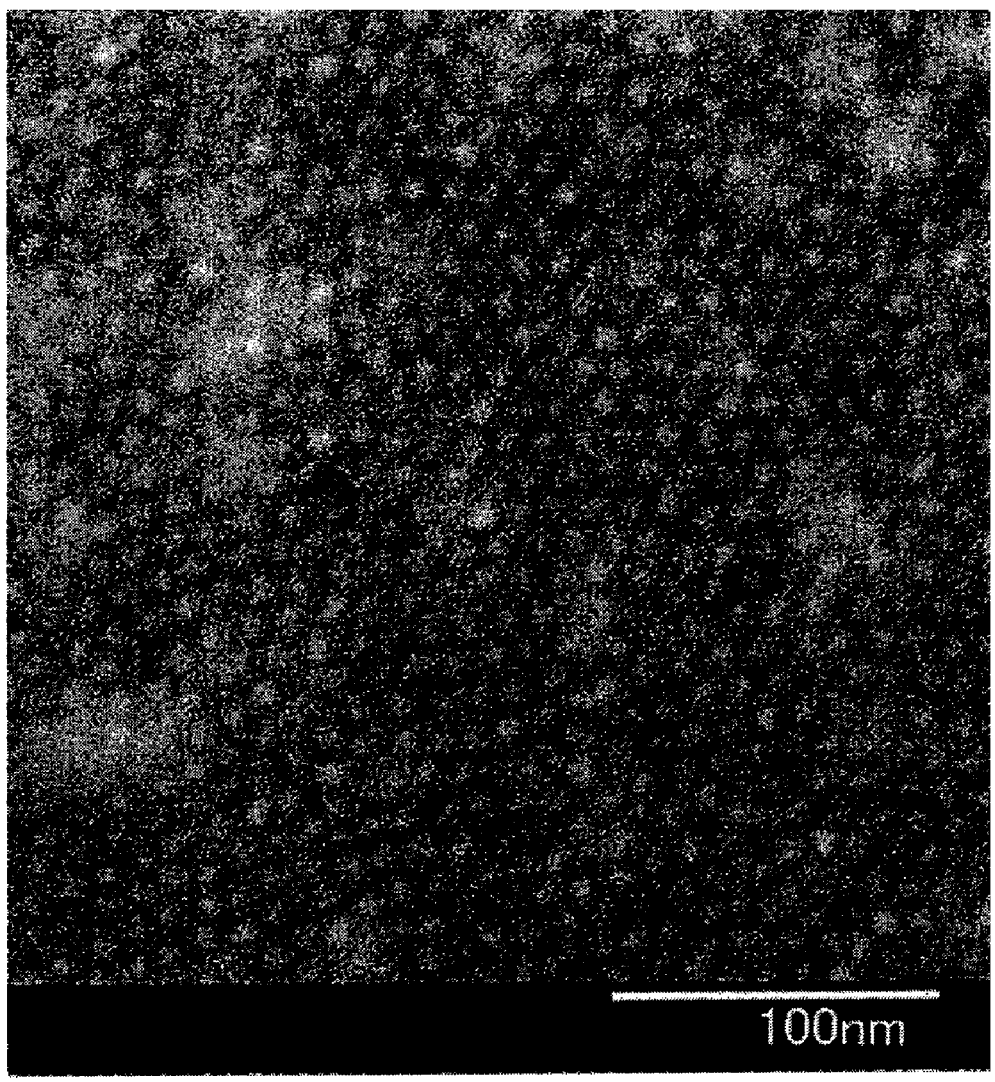
FIG. 67 shows a photograph illustrating the appearance of a two-dimensional array of ferritin obtained in Comparative Example 28.
Figure 68:
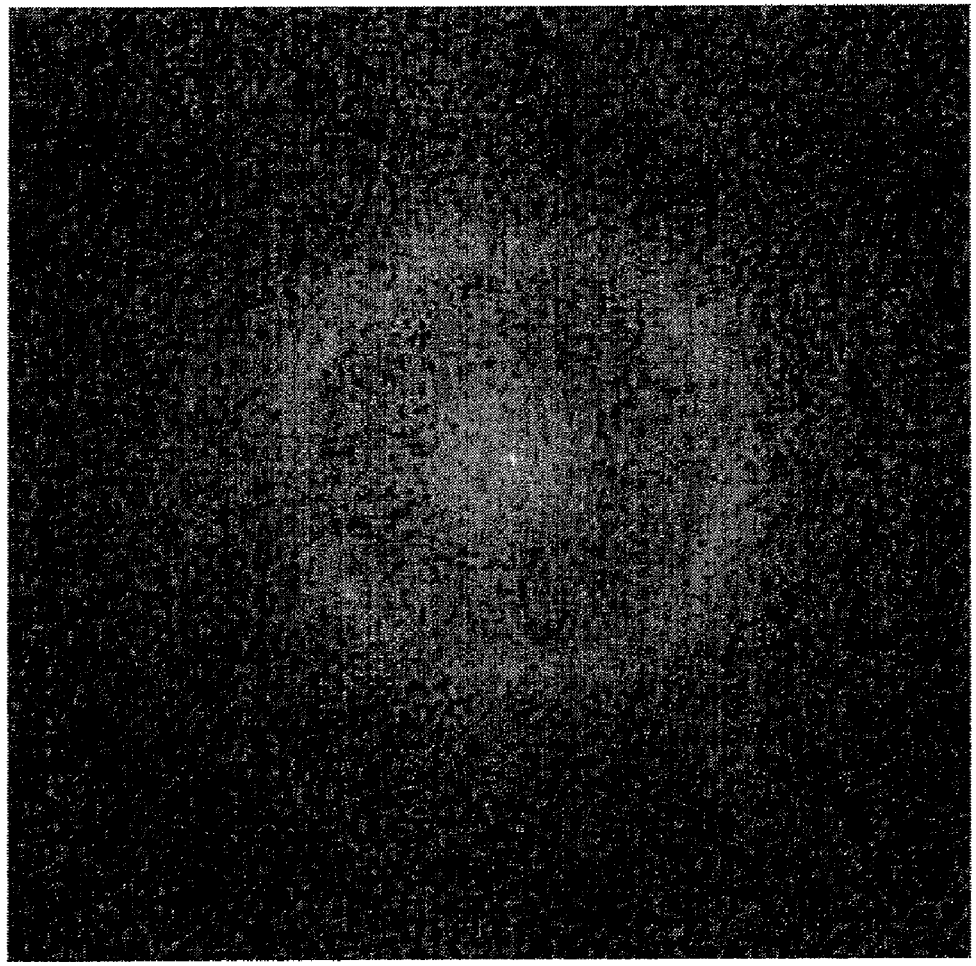
FIG. 68 shows a photograph of Fourier transformation image illustrating the appearance of a two-dimensional array of ferritin obtained in Comparative Example 28.

A photograph illustrating the appearance of a two-dimensional array of ferritin obtained using 0.5 mg/ml shuffle-Fer0 (In), and 20 mM ammonium acetate is shown in FIG. 67, and a Fourier transformation image thereof is shown in FIG. 68.

It could be verified that the ferritin Shuffle-Fer0 having an amino acid sequence with substitution by twelve different amino acid residues from N1-LF in conventional example on its outer peripheral surface formed "inferior two-dimensional array".

Comparative Example 29

Figure 69:
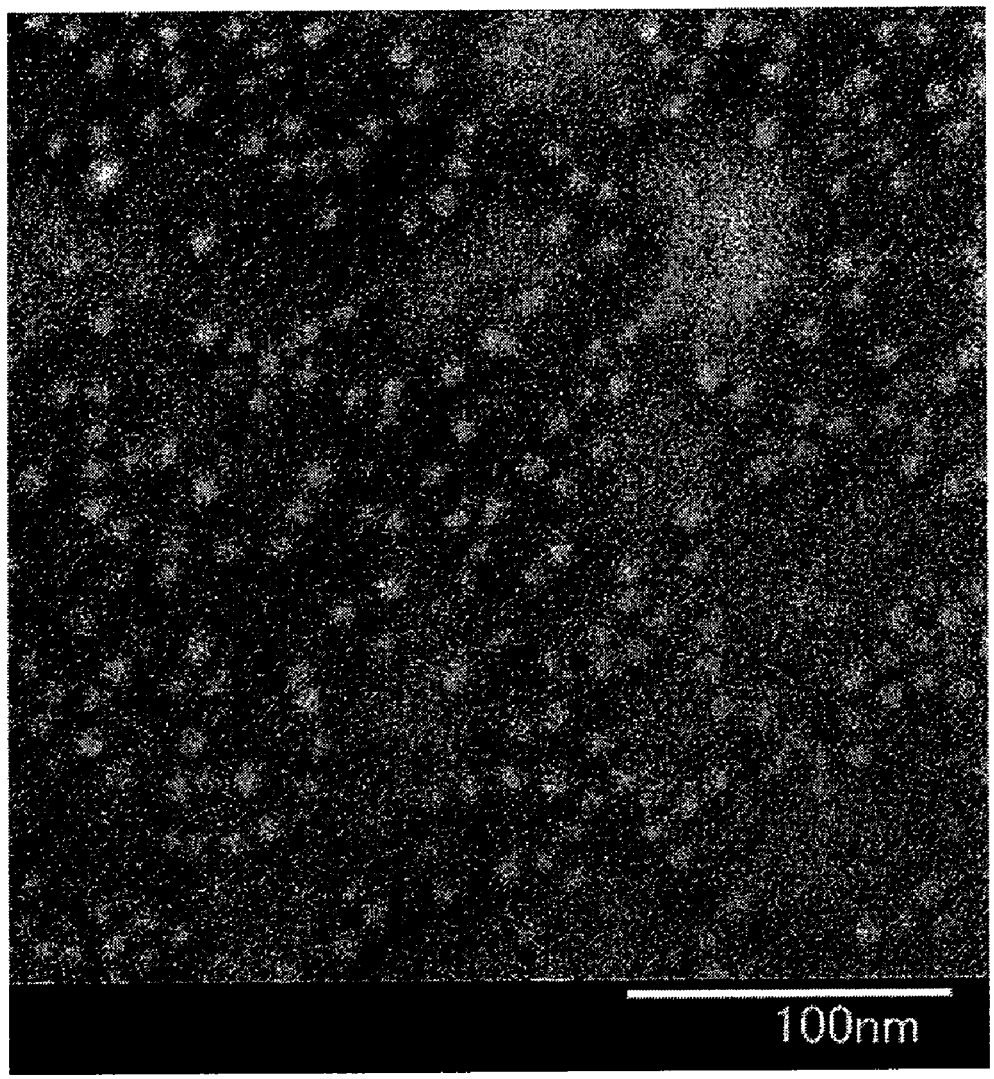
FIG. 69 shows a photograph illustrating the appearance of a two-dimensional array of ferritin obtained in Comparative Example 29.
Figure 70:
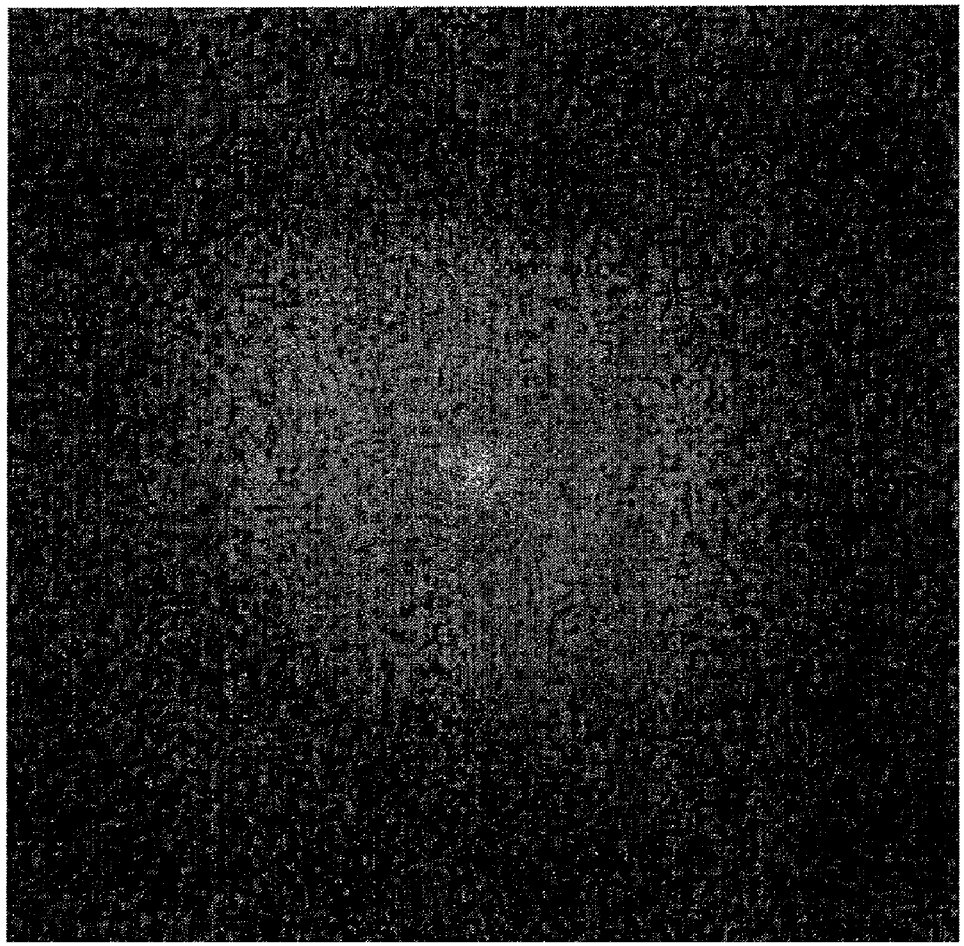
FIG. 70 shows a photograph of Fourier transformation image illustrating the appearance of a two-dimensional array of ferritin obtained in Comparative Example 29.

A photograph illustrating the appearance of attachment of ferritin obtained using 0.5 mg/ml 1st-half-Fer0 (In) and 12.5 mM PIPES-NaOH (pH 7.0) is shown in FIG. 69, and a Fourier transformation image thereof is shown in FIG. 70.

Comparative Example 30

Figure 71:
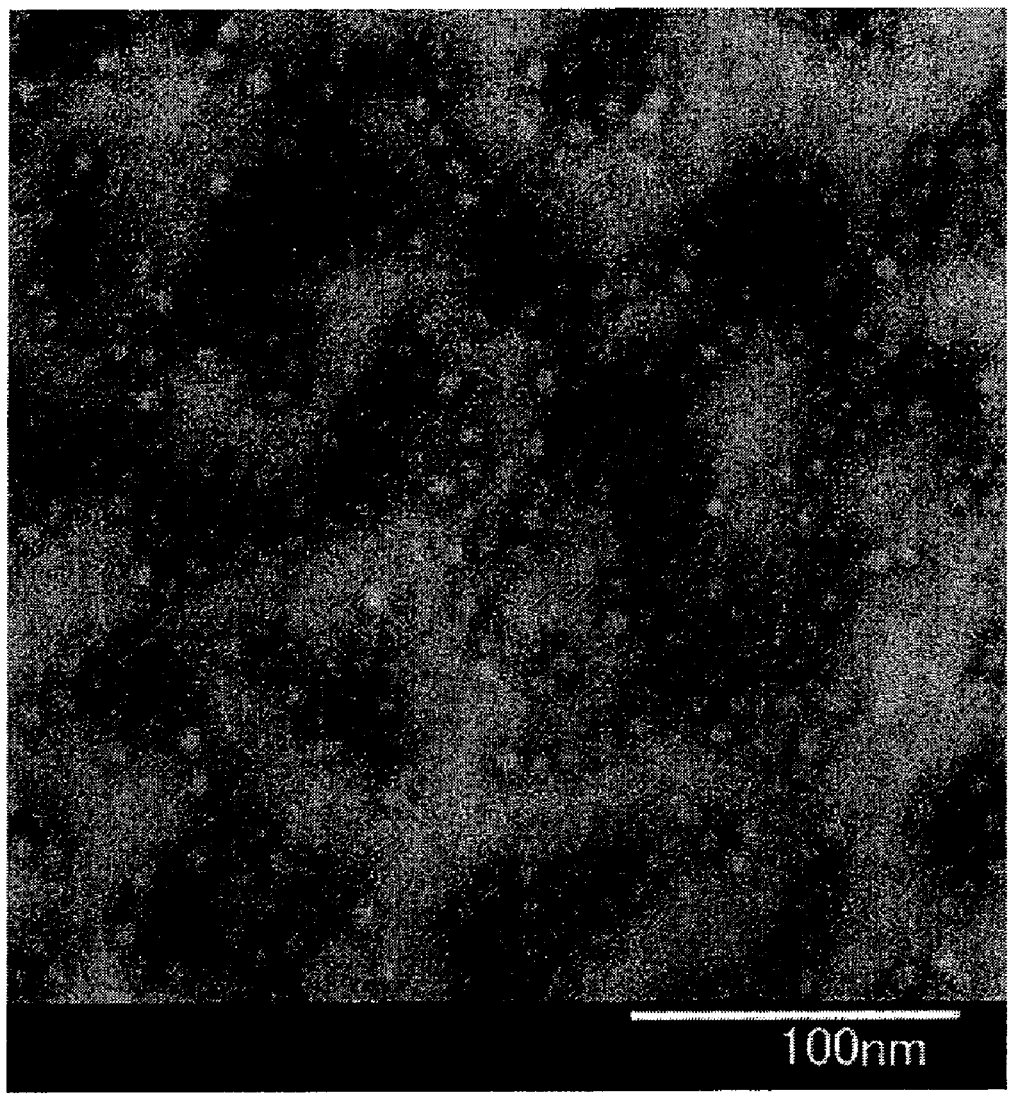
FIG. 71 shows a photograph illustrating the appearance of a two-dimensional array of ferritin obtained in Comparative Example 30.
Figure 72:
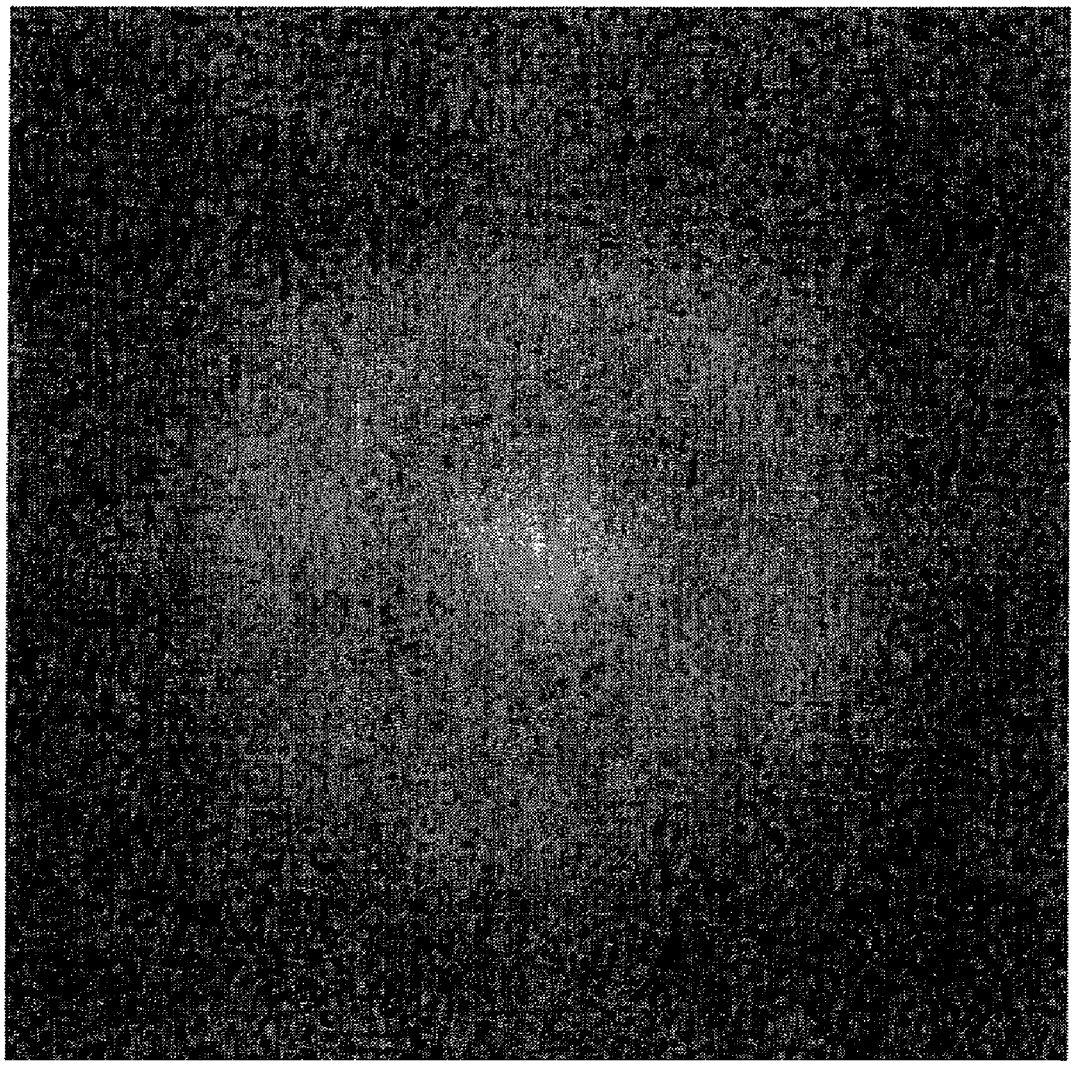
FIG. 72 shows a photograph of Fourier transformation image illustrating the appearance of a two-dimensional array of ferritin obtained in Comparative Example 30.

A photograph illustrating the appearance of attachment of ferritin obtained using 0.5 mg/ml 1st-half-Fer0 (In) and 13 mM ammonium sulfate is shown in FIG. 71, and a Fourier transformation image thereof is shown in FIG. 72.

Comparative Example 31

Figure 73:
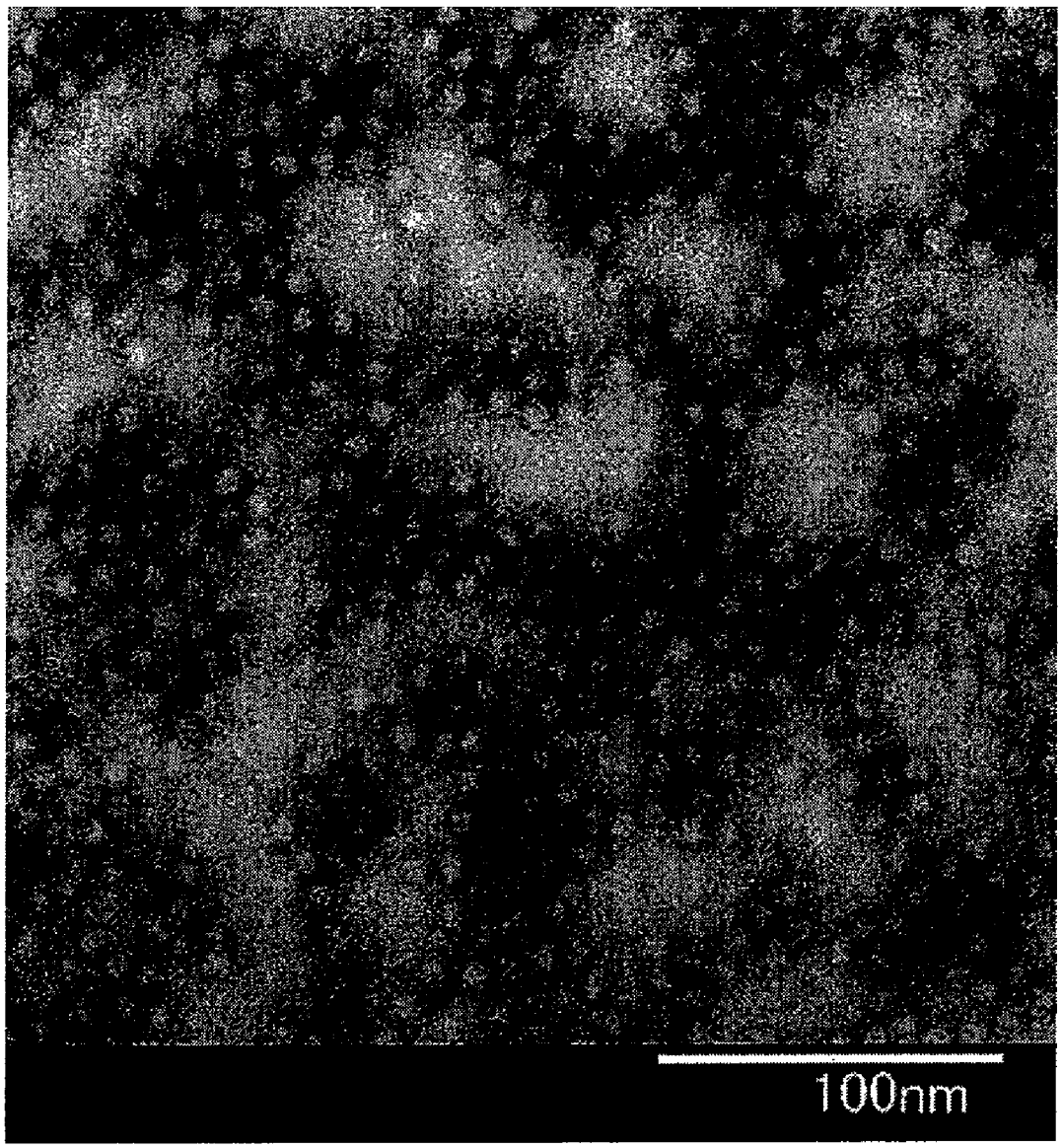
FIG. 73 shows a photograph illustrating the appearance of a two-dimensional array of ferritin obtained in Comparative Example 31.
Figure 74:
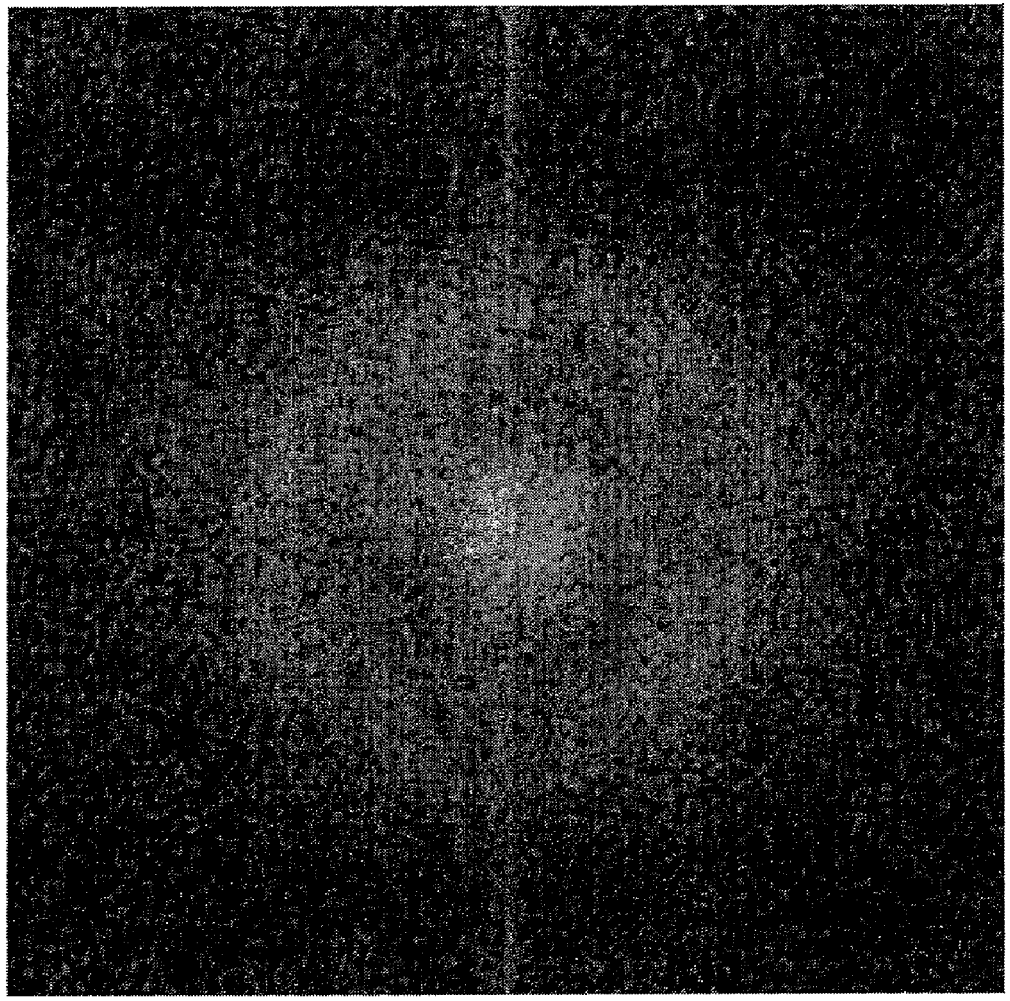
FIG. 74 shows a photograph of Fourier transformation image illustrating the appearance of a two-dimensional array of ferritin obtained in Comparative Example 31.

A photograph illustrating the appearance of attachment of ferritin obtained using 0.5 mg/ml 1st-half-Fer0 (In) and 20 mM ammonium acetate is shown in FIG. 73, and a Fourier transformation image thereof is shown in FIG. 74.

Comparative Example 32

Figure 75:
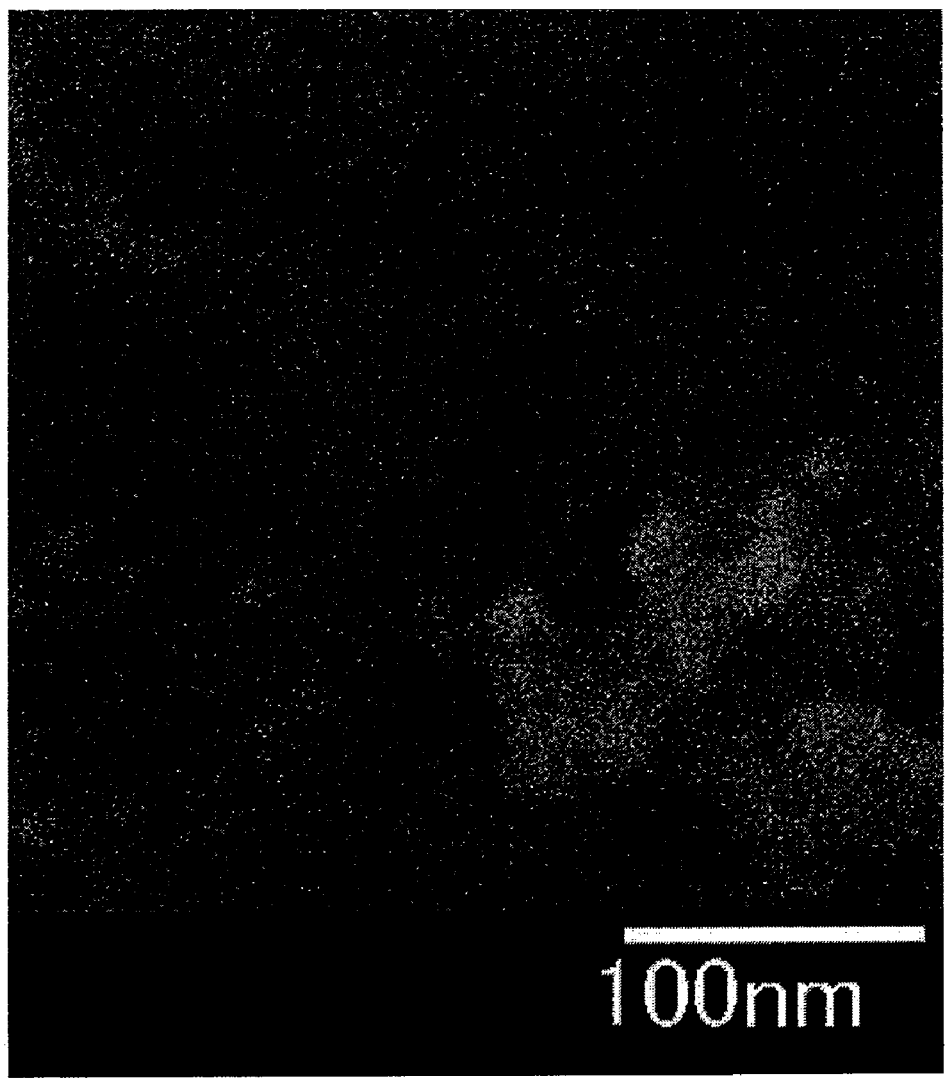
FIG. 75 shows a photograph illustrating the appearance of a two-dimensional array of ferritin obtained in Comparative Example 32.
Figure 76:
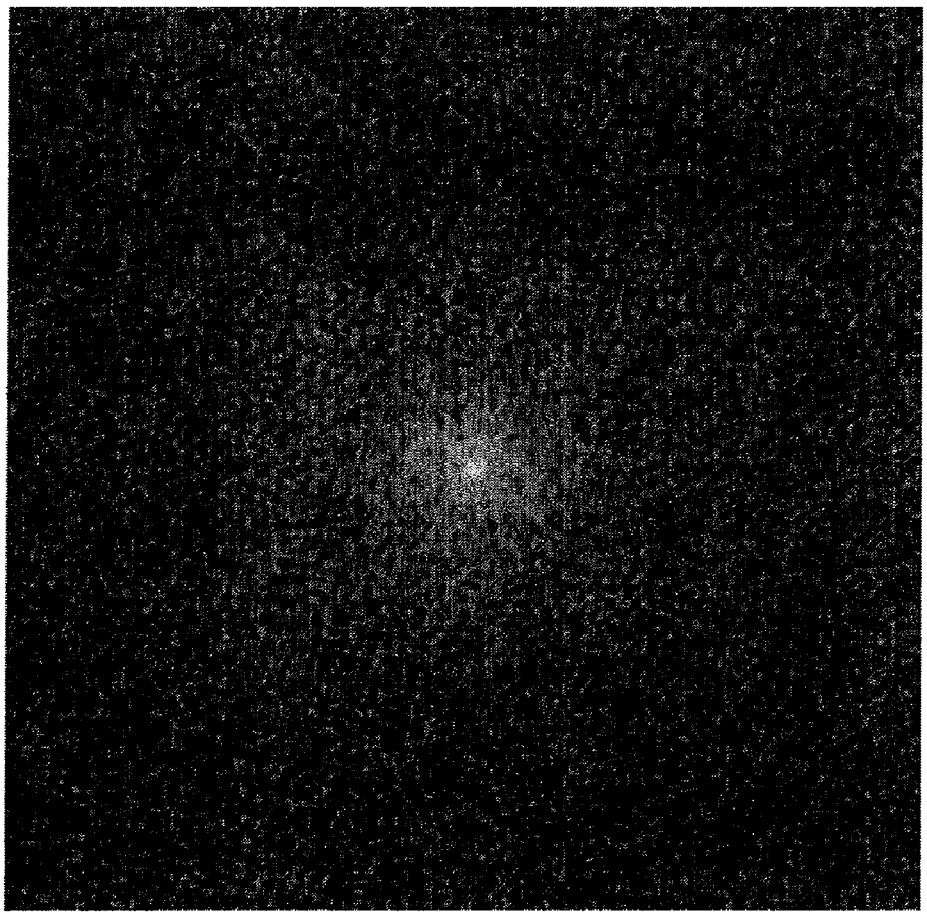
FIG. 76 shows a photograph of Fourier transformation image illustrating the appearance of a two-dimensional array of ferritin obtained in Comparative Example 32.

A photograph illustrating the appearance of attachment of ferritin obtained using 0.5 mg/ml 2nd-half-Fer0 (In) and 12.5 mM PIPES-NaOH (pH 7.0) is shown in FIG. 75, and a Fourier transformation image thereof is shown in FIG. 76.

Comparative Example 33

Figure 77:
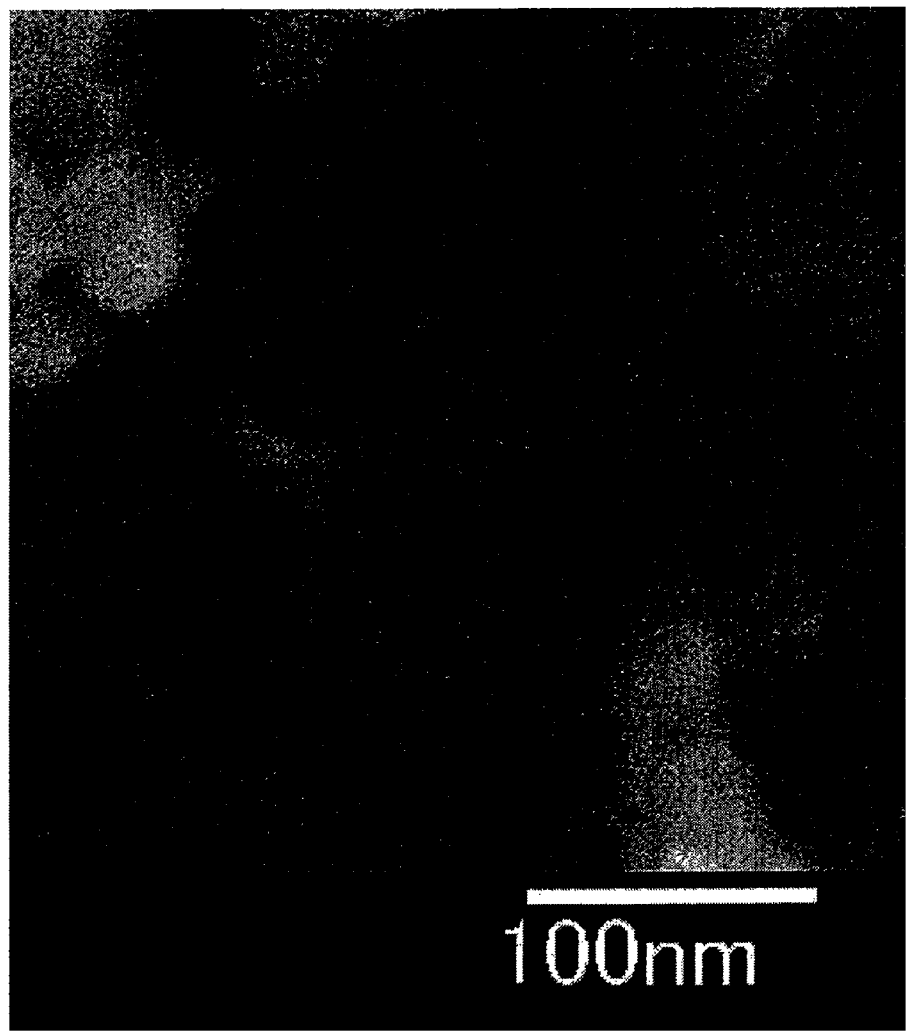
FIG. 77 shows a photograph illustrating the appearance of a two-dimensional array of ferritin obtained in Comparative Example 33.
Figure 78:
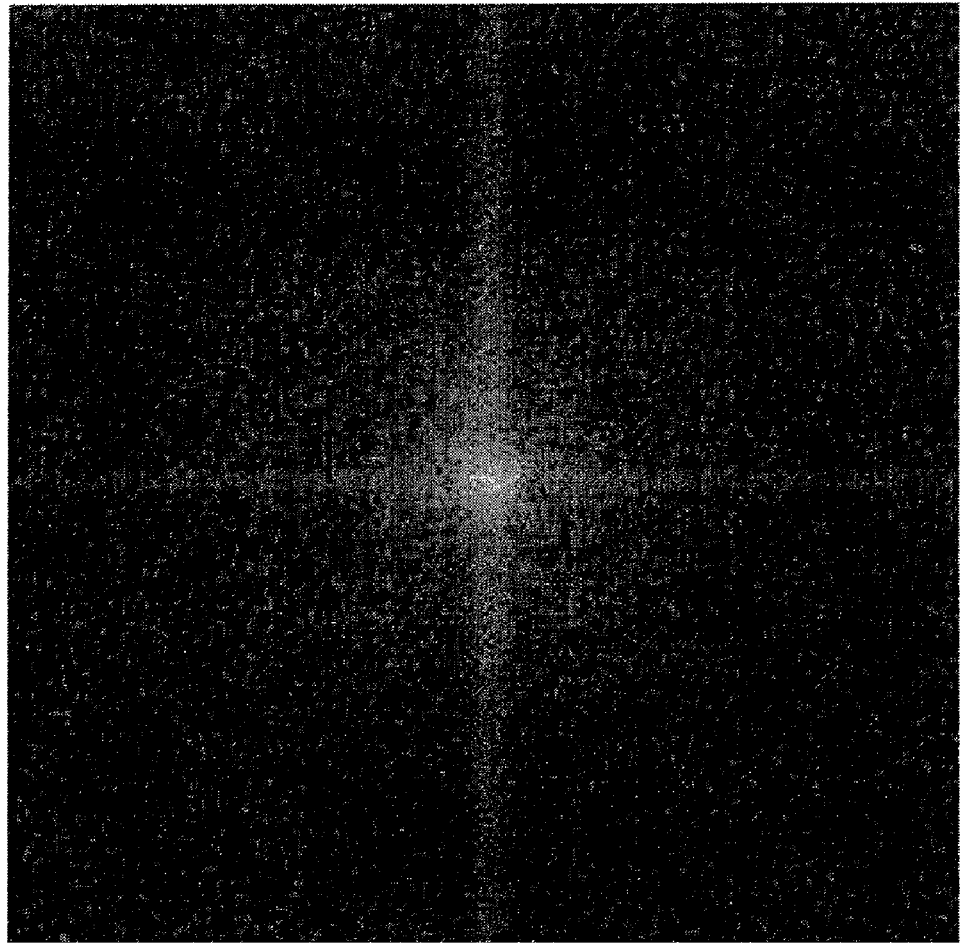
FIG. 78 shows a photograph of Fourier transformation image illustrating the appearance of a two-dimensional array of ferritin obtained in Comparative Example 33.

A photograph illustrating the appearance of attachment of ferritin obtained using 0.5 mg/ml 2nd-half-Fer0 (In) and 13 mM ammonium sulfate is shown in FIG. 77, and a Fourier transformation image thereof is shown in FIG. 78.

Comparative Example 34

Figure 79:
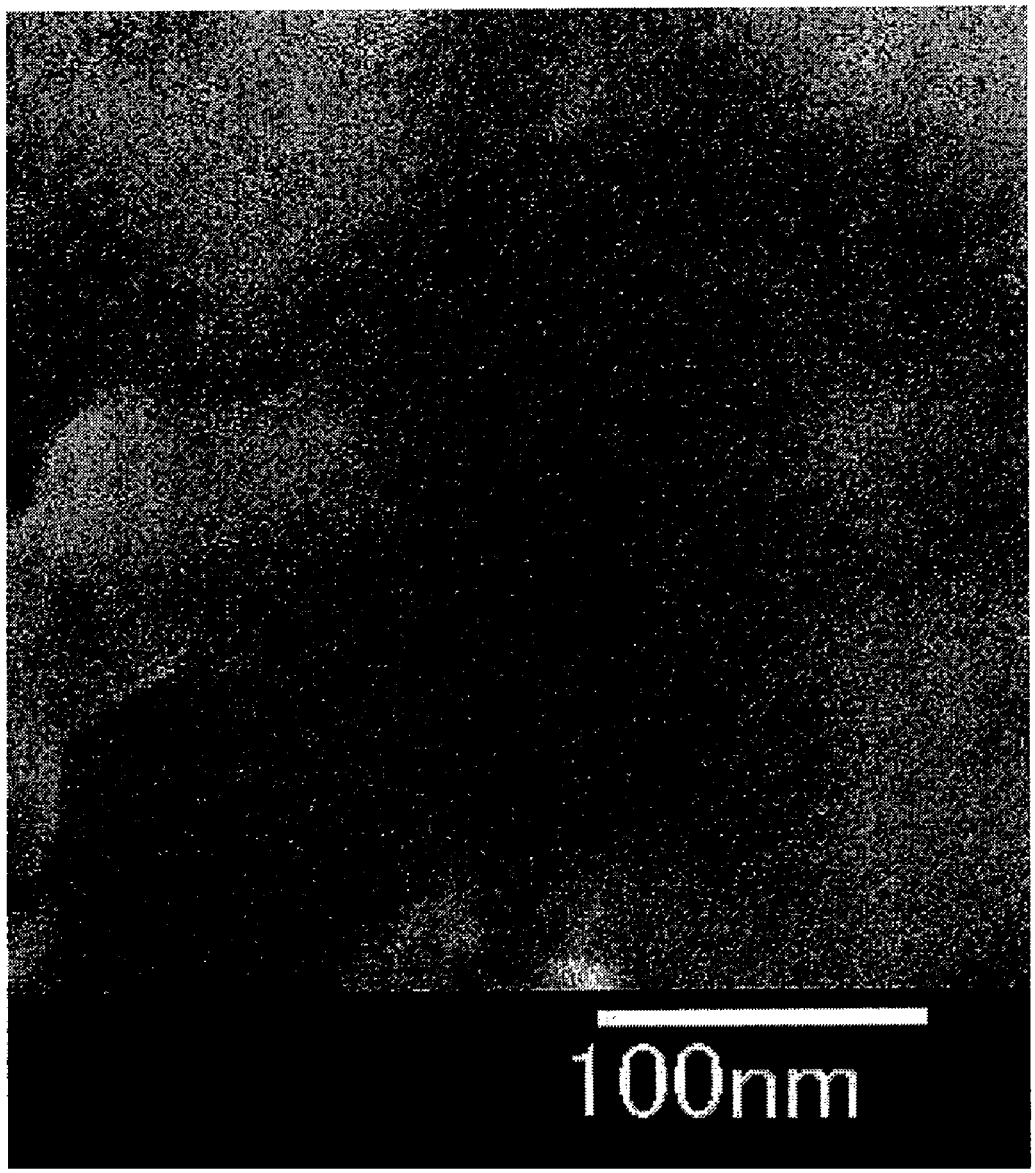
FIG. 79 shows a photograph illustrating the appearance of a two-dimensional array of ferritin obtained in Comparative Example 34.
Figure 80:
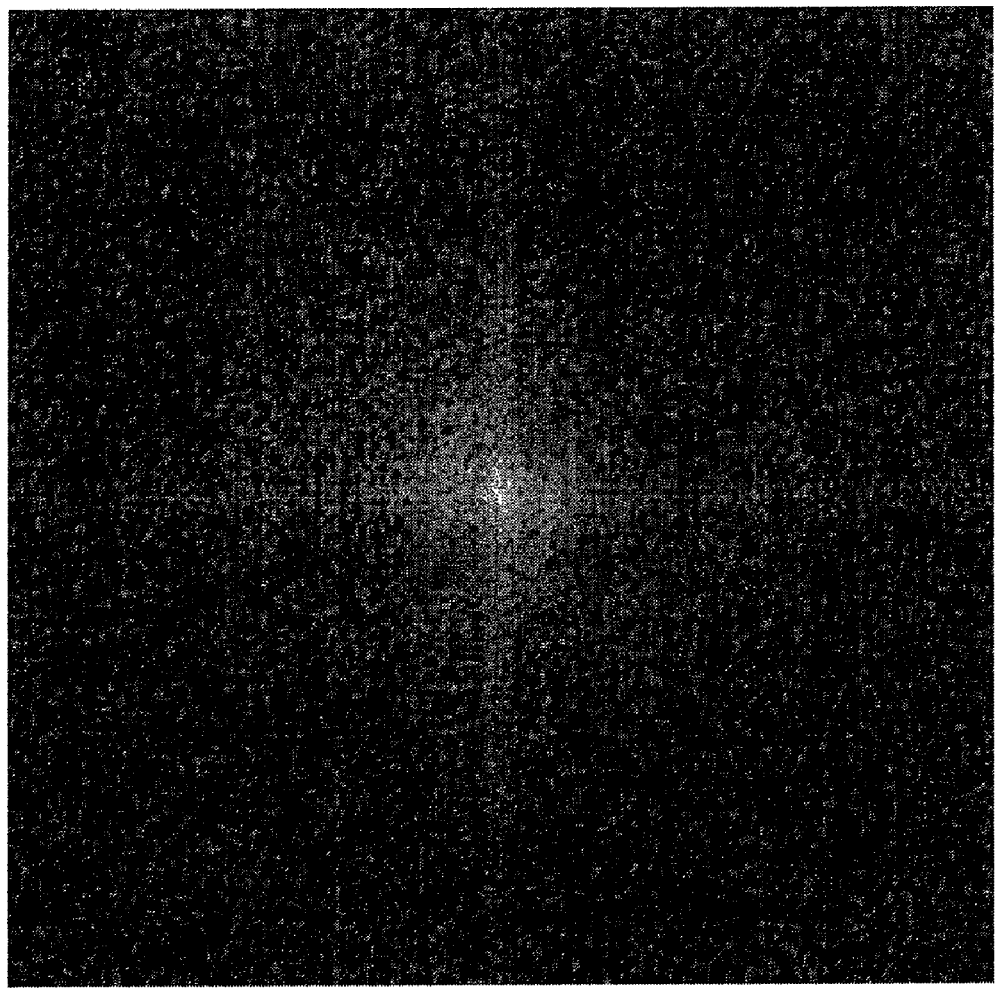
FIG. 80 shows a photograph of Fourier transformation image illustrating the appearance of a two-dimensional array of ferritin obtained in Comparative Example 34.

A photograph illustrating the appearance of attachment of ferritin obtained using 0.5 mg/ml 2nd-half-Fer0 (In) and 20 mM ammonium acetate is shown in FIG. 79, and a Fourier transformation image thereof is shown in FIG. 80.

It could be verified that the ferritin 1st-half-Fer0 and 2nd-half-Fer0 having an amino acid sequence with deletion of amino acid residues from N1-LF (having twelve amino acid residues) in conventional example, i.e., the ferritin having a shorter amino acid sequence (having six amino acid residues) on its outer peripheral surface "did not form a two-dimensional array".

Comparative Example 35

Figure 81:
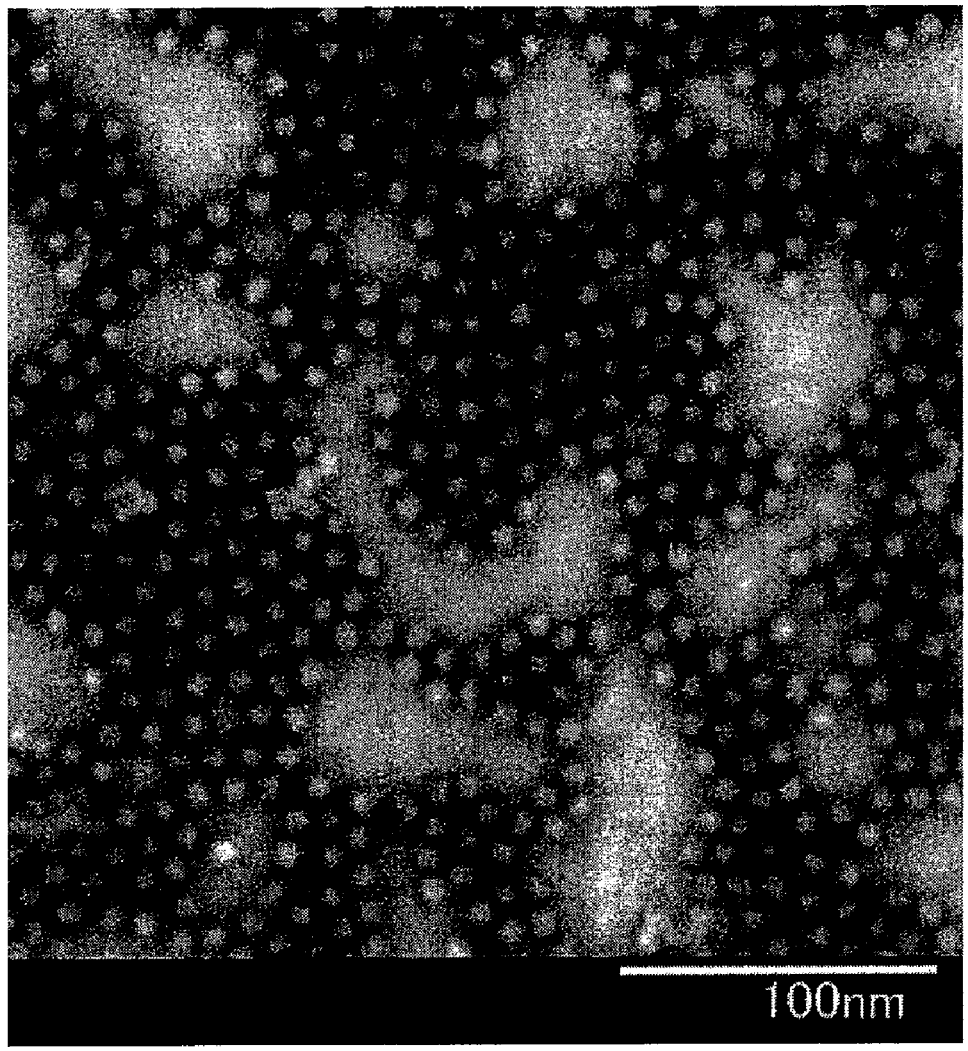
FIG. 81 shows a photograph illustrating the appearance of a two-dimensional array of ferritin obtained in Comparative Example 35.
Figure 82:
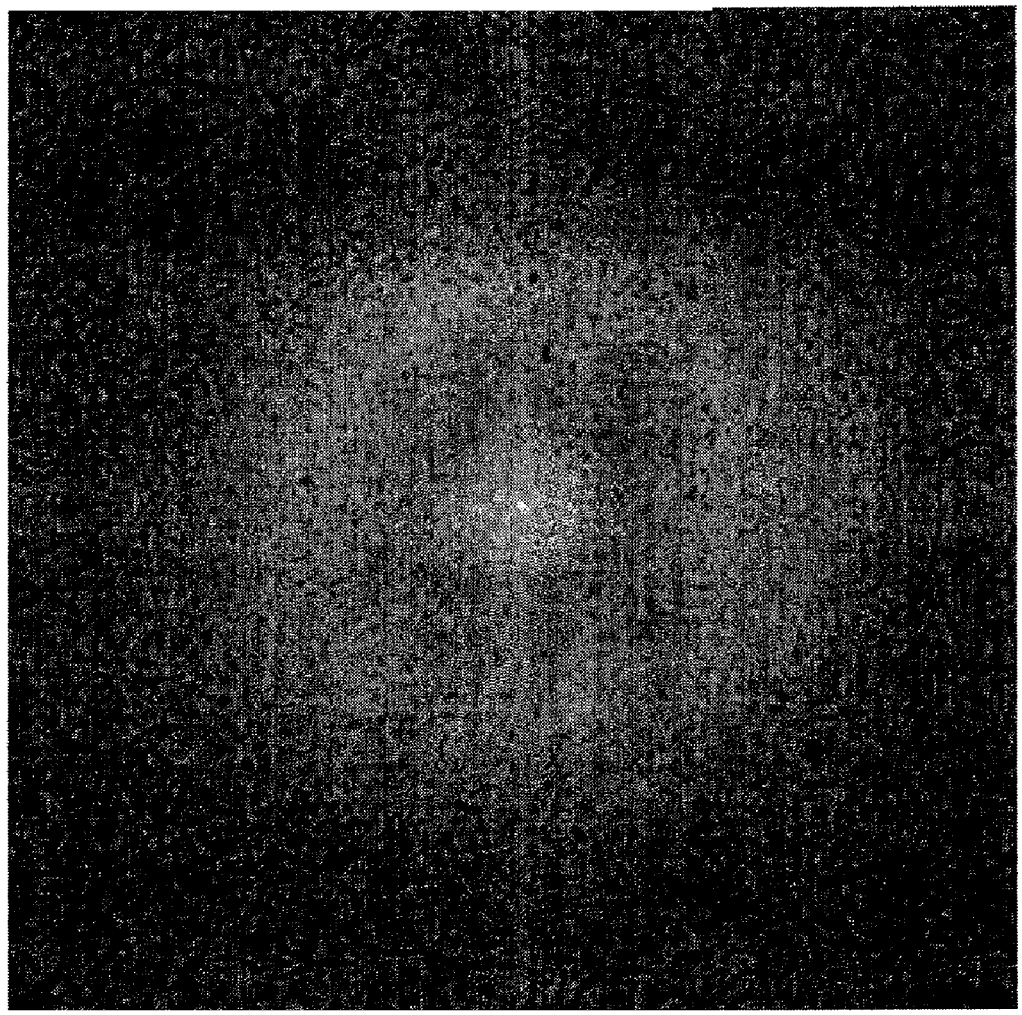
FIG. 82 shows a photograph of Fourier transformation image illustrating the appearance of a two-dimensional array of ferritin obtained in Comparative Example 35.

A photograph illustrating the appearance of attachment of ferritin obtained using 0.5 mg/ml 5AA-Fer0 (In) and 12.5 mM PIPES-NaOH (pH 7.0) is shown in FIG. 81, and a Fourier transformation image thereof is shown in FIG. 82.

Comparative Example 36

Figure 83:
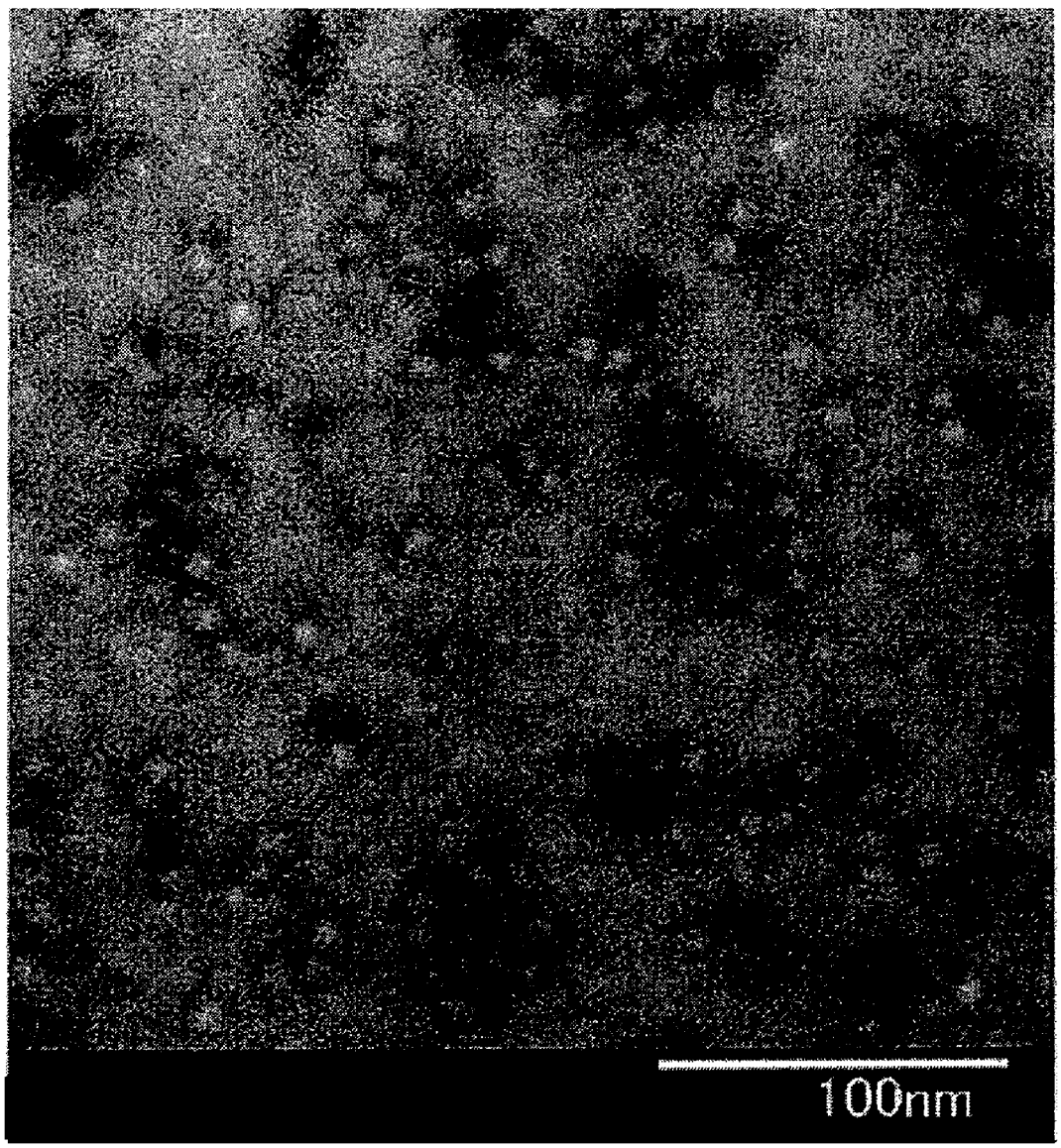
FIG. 83 shows a photograph illustrating the appearance of a two-dimensional array of ferritin obtained in Comparative Example 36.
Figure 84:
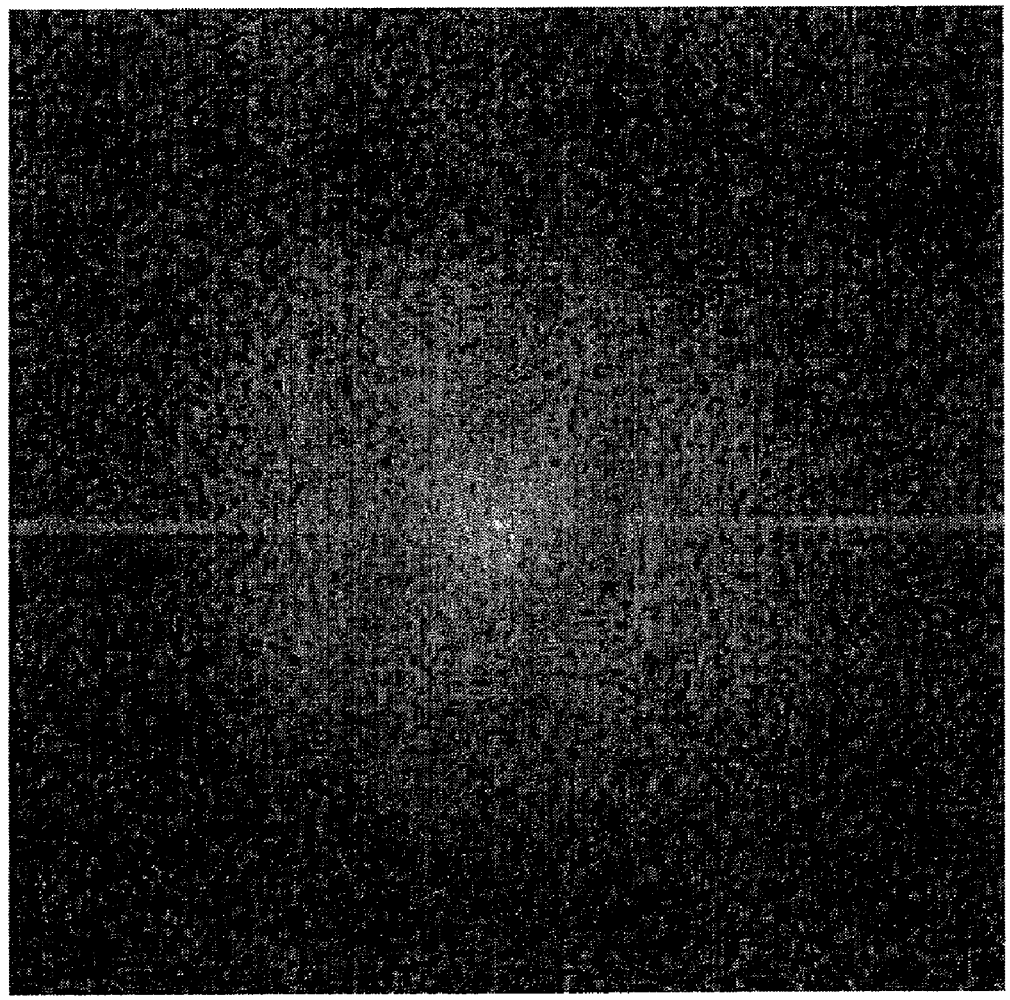
FIG. 84 shows a photograph of Fourier transformation image illustrating the appearance of a two-dimensional array of ferritin obtained in Comparative Example 36.

A photograph illustrating the appearance of attachment of ferritin obtained using 0.5 mg/ml 5AA-Fer0 (In) and 13 mM ammonium sulfate is shown in FIG. 83, and a Fourier transformation image thereof is shown in FIG. 84.

Comparative Example 37

Figure 85:
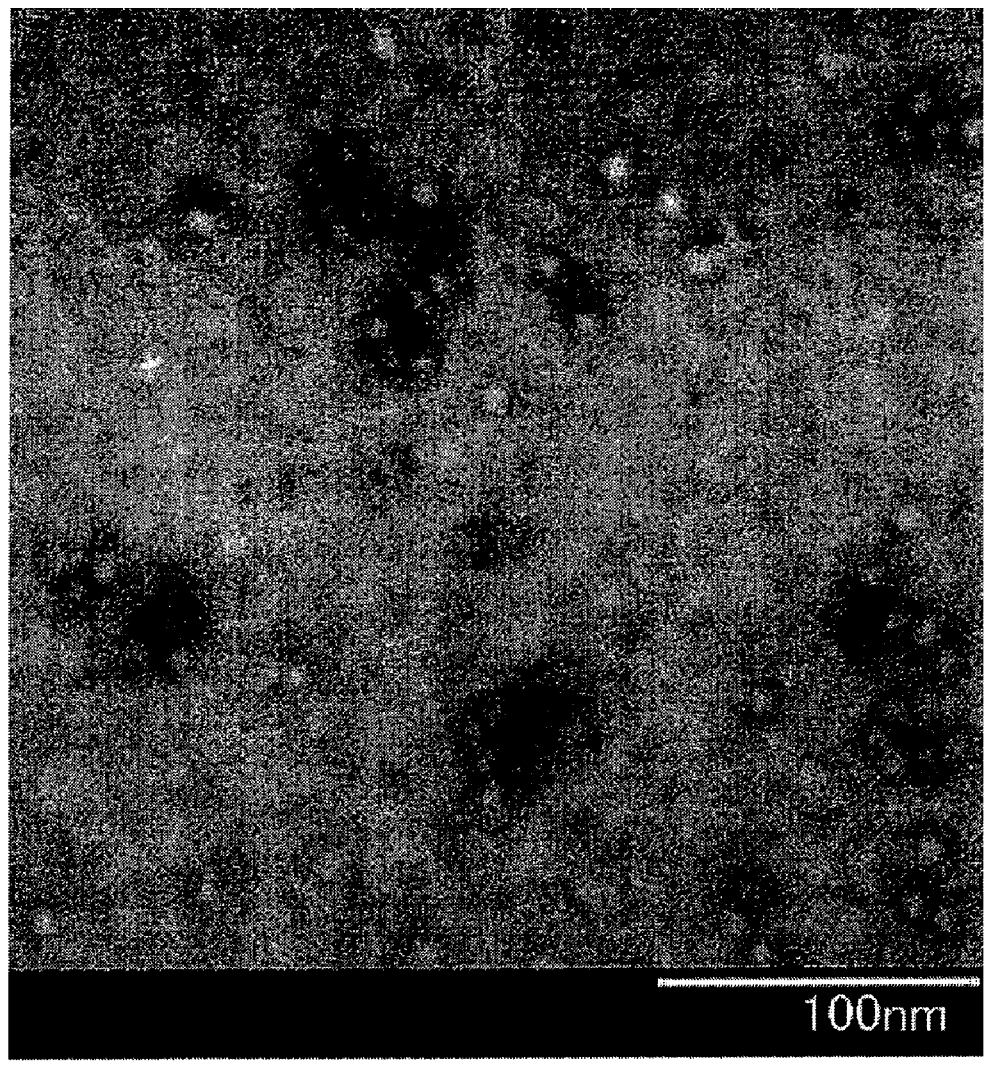
FIG. 85 shows a photograph illustrating the appearance of a two-dimensional array of ferritin obtained in Comparative Example 37.
Figure 86:
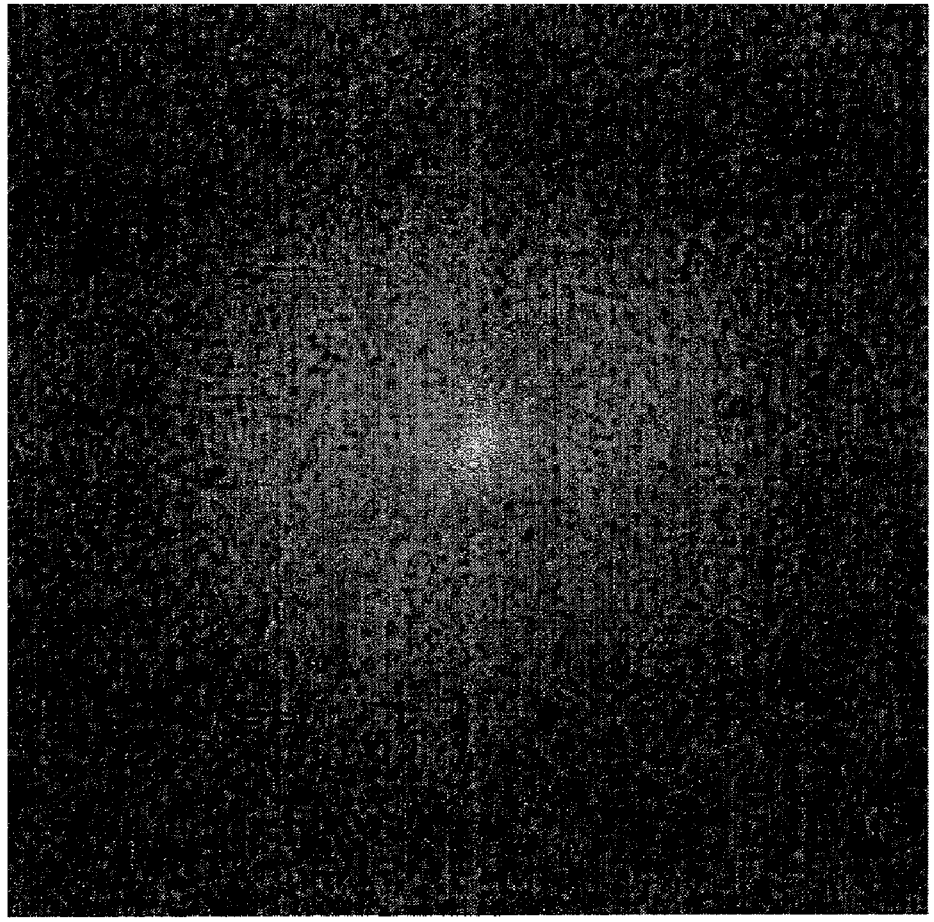
FIG. 86 shows a photograph of Fourier transformation image illustrating the appearance of a two-dimensional array of ferritin obtained in Comparative Example 37.
Figure 87:
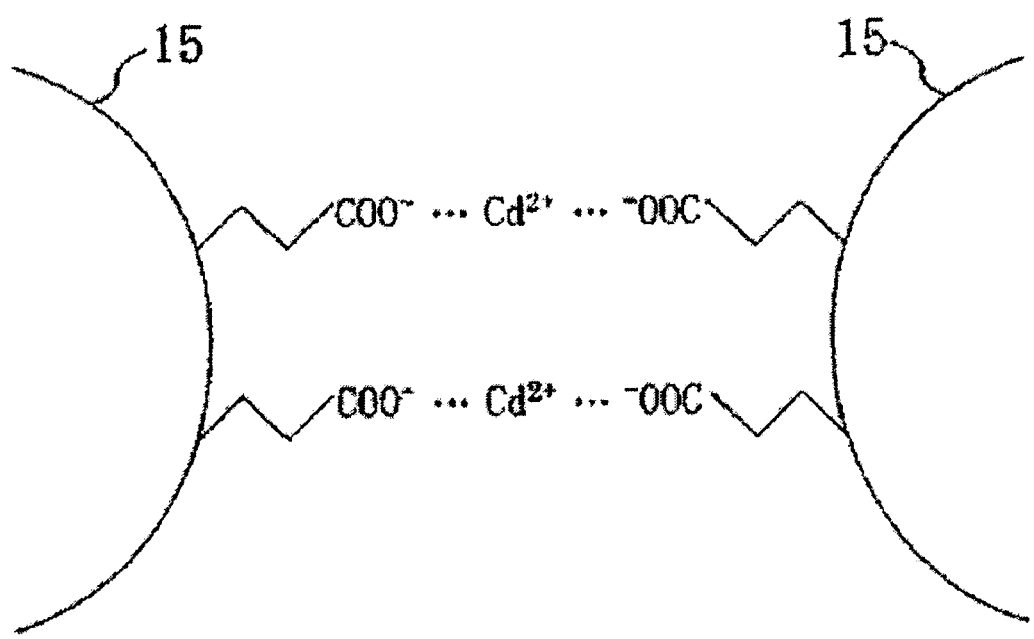
FIG. 87 shows a schematic view illustrating a state in which crosslinking between two adjacent particles of ferritin is effected via a bivalent metal ion (cadmium ion in FIG. 87) which had been shown in FIG. 8 in Pamphlet of International Publication No. 03/040025.
Figure 88:
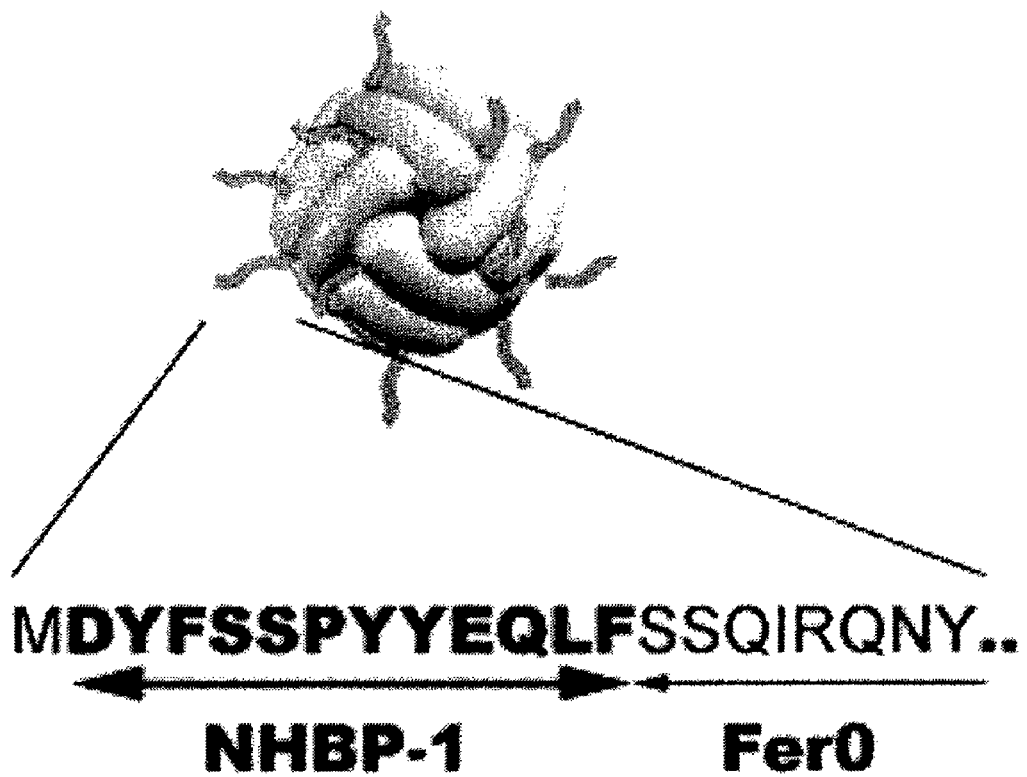
FIG. 88 shows a schematic view illustrating modified ferritin (N1-LF) which had been described in Langmuir, Vol. 23, pp. 1615-1618, (2007), SEQ ID 5 AND SEQ ID 6 with methionine.

A photograph illustrating the appearance of attachment of ferritin obtained using 0.5 mg/ml 5AA-Fer0 (In) and 20 mM ammonium acetate is shown in FIG. 85, and a Fourier transformation image thereof is shown in FIG. 86.

It could be verified that the ferritin 5AA-Fer0 having an amino acid sequence with deletion of seven amino acid residues from N1-LF (having twelve amino acid residues) in conventional example, i.e., the ferritin having a shorter amino acid sequence (having five amino acid residues) on its outer peripheral surface "did not form a two-dimensional array".

The correlation between formation of the two-dimensional array, and the number of modified amino acid residues (the number of modification from N1-LF) is summarized in Table 3 below.

TABLE 3

| Peptide name | Number of modified amino acid residues | Formation of two-dimensional array |
|---|---|---|
| Y6S4DE | 5 amino acid residues substitution | "favorable two-dimensional array" or "inferior two-dimensional array" |
| D2N | 1 amino acid residue substitution | "favorable two-dimensional array" |
| E10Q | 1 amino acid residue substitution | "favorable two-dimensional array" or "inferior two-dimensional array" |
| E10S | 1 amino acid residue substitution | "favorable two-dimensional array" |
| P7S | 1 amino acid residue substitution | "favorable two-dimensional array" |
| Y8F-Y9F | 2 amino acid residues substitution | "inferior two-dimensional array" |
| S5T-S6T | 2 amino acid residues substitution | "inferior two-dimensional array" |
| ΔHY | 5 amino acid residues substitution | "two-dimensional array not formed" |
| ΔAR | 5 amino acid residues substitution | "inferior two-dimensional array" |
| Shuffle | 12 amino acid residues substitution | "inferior two-dimensional array" |
| 1st half | 6 amino acid residues deletion | "two-dimensional array not formed" |
| 2nd half | 6 amino acid residues deletion | "two-dimensional array not formed" |
| 5AA | 7 amino acid residues deletion | "two-dimensional array not formed" |

The ferritin used in the present invention does not require a bivalent metal ion in forming a two-dimensional array. Therefore, adverse influences typified by appearance of unexpected interface state on the quantum dot provided by two-dimensionally arraying a metal on a substrate can be suppressed.

The peptide set out in SEQ ID NO: 1 presented on the outer surface of ferritin used in the present invention has a novel sequence in which five amino acid residues among 12 amino acid residues are different as compared with the amino acid sequence of the peptide in conventional example set out in SEQ ID NO: 5, and can form a "favorable two-dimensional array" or an "inferior two-dimensional array" on a substrate.

From the foregoing description, it can be construed that the ferritin used in the present invention can be two-dimensionally arrayed on a substrate without exerting adverse influences typified by appearance of unexpected interface state, and that it presents a novel peptide on the outer surface thereof, the peptide having a sequence distinct from those in conventional examples.

The present invention can be utilized in a variety of devices, semiconductor apparatuses and the like, which make use of nanoparticles arranged on a substrate.

What is claimed is:

1. A method of two-dimensionally arraying ferritin on a substrate, comprising:
   (a) developing a solution and the ferritin on the substrate, wherein, the solution comprises:
      a solvent consisting of water, and
      at least one from the group consisting of PIPES, ammonium sulfate, and ammonium acetate,
   wherein the N-terminal of the ferritin is SEQ ID NO: 1 and the surface of the substrate is hydrophilic and;
   (b) removing the solvent from the solution developed on the substrate.

2. The method according to claim 1 wherein the surface of the substrate is covered by $SiO_2$.

3. The method according to claim 1 wherein the concentration of PIPES in the solution is not lower than 5 mM and not higher than 50 mM.

4. The method according to claim 1 wherein the concentration of ammonium sulfate in the solution is not lower than 6.5 mM and not higher than 52 mM.

5. The method according to claim 1 wherein the concentration of ammonium acetate in the solution is not lower than 2 mM and not higher than 100 mM.

* * * * *